United States Patent
Gubau i Forné et al.

(10) Patent No.: US 12,061,618 B2
(45) Date of Patent: *Aug. 13, 2024

(54) MANAGING DATA FOR REGULATED ENVIRONMENTS

(71) Applicant: Bigfinite Inc., San Francisco, CA (US)

(72) Inventors: Josep Gubau i Forné, San Francisco, CA (US); Antonio Manzano Doñabeitia, Barcelona (ES); Pere Merino Tarafa, Barcelona (ES)

(73) Assignee: Bigfinite Inc., San Francisco, CA (US)

( * ) Notice: Subject to any disclaimer, the term of this patent is extended or adjusted under 35 U.S.C. 154(b) by 335 days.

This patent is subject to a terminal disclaimer.

(21) Appl. No.: 17/152,681

(22) Filed: Jan. 19, 2021

(65) Prior Publication Data

US 2021/0141786 A1 May 13, 2021

Related U.S. Application Data

(63) Continuation of application No. 15/018,828, filed on Feb. 8, 2016, now Pat. No. 10,901,962.

(60) Provisional application No. 62/129,485, filed on Mar. 6, 2015, provisional application No. 62/113,217, filed on Feb. 6, 2015.

(51) Int. Cl.
| | |
|---|---|
| G06F 16/245 | (2019.01) |
| G06F 16/215 | (2019.01) |
| G06F 16/248 | (2019.01) |
| G06Q 10/0639 | (2023.01) |
| G06Q 30/018 | (2023.01) |
| G16H 20/10 | (2018.01) |
| G16H 70/40 | (2018.01) |

(52) U.S. Cl.
CPC .......... *G06F 16/248* (2019.01); *G06F 16/215* (2019.01); *G06F 16/245* (2019.01); *G06Q 10/06395* (2013.01); *G06Q 30/018* (2013.01); *G16H 20/10* (2018.01); *G16H 70/40* (2018.01)

(58) Field of Classification Search
CPC ..... G06F 16/215; G06F 16/245; G06F 16/248
See application file for complete search history.

(56) References Cited

U.S. PATENT DOCUMENTS

| | | | | |
|---|---|---|---|---|
| 5,574,898 | A * | 11/1996 | Leblang | G06F 11/3476 |
| 6,865,577 | B1 * | 3/2005 | Sereda | G06F 16/2255 |
| | | | | 707/699 |
| 7,574,429 | B1 * | 8/2009 | Zaifman | G06F 16/174 |
| 2005/0281276 | A1 | 12/2005 | West et al. | |
| 2008/0125887 | A1 | 5/2008 | Case | |
| 2008/0189498 | A1 * | 8/2008 | Brown | G06F 11/2097 |
| | | | | 711/162 |
| 2009/0132540 | A1 | 3/2009 | Hjelm et al. | |
| 2009/0312897 | A1 | 12/2009 | Jamrosz et al. | |

(Continued)

OTHER PUBLICATIONS

Authorized officer Blaine R. Copenheaver, International Search Report and Written Opinion in Application No. PCT/US2016/017034, mailed Apr. 14, 2016, 10 pages.

*Primary Examiner* — James E Richardson
(74) *Attorney, Agent, or Firm* — Fish & Richardson P.C.

(57) ABSTRACT

Methods, systems, and apparatus, including computer programs encoded on computer storage media, for managing data for regulated environments. One of the methods includes collecting data from a plurality of sources; analyzing the data; and providing one or more outputs based on the analysis.

18 Claims, 35 Drawing Sheets

(56) References Cited

U.S. PATENT DOCUMENTS

| | | |
|---|---|---|
| 2010/0299335 A1 | 11/2010 | Gopalakrishnan et al. |
| 2012/0209575 A1 | 8/2012 | Barbat et al. |
| 2012/0215554 A1 | 8/2012 | Yurkovich |
| 2012/0296692 A1 | 11/2012 | O'Malley et al. |
| 2013/0211555 A1 | 8/2013 | Lawson et al. |
| 2014/0058775 A1 | 2/2014 | Siig et al. |
| 2014/0337388 A1 | 11/2014 | Hacker |
| 2016/0179849 A1* | 6/2016 | Dubois ................ G06F 16/211 707/803 |
| 2016/0267150 A1 | 9/2016 | Forne et al. |
| 2016/0328719 A1 | 11/2016 | Ananchaperumal et al. |
| 2016/0346705 A1 | 12/2016 | Togawa et al. |
| 2018/0350006 A1* | 12/2018 | Agrawal ................ G06F 7/026 |

* cited by examiner

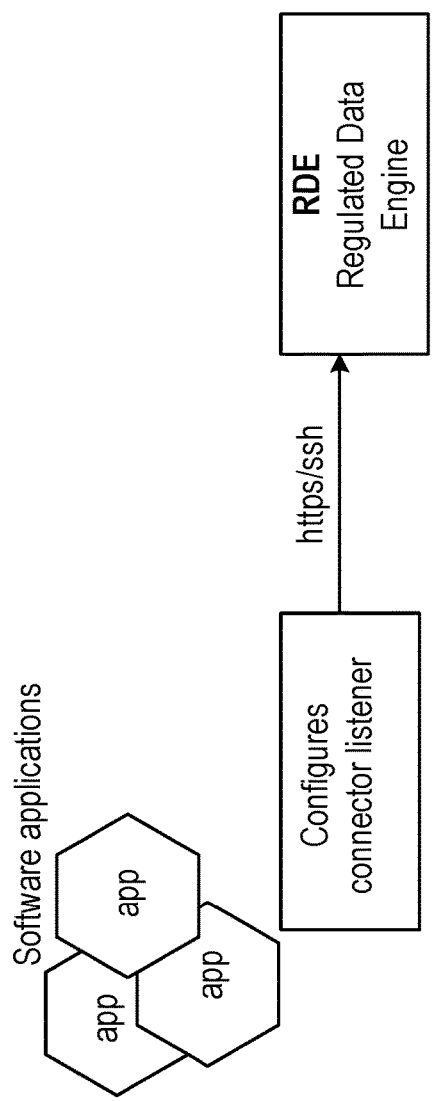
FIG. 14
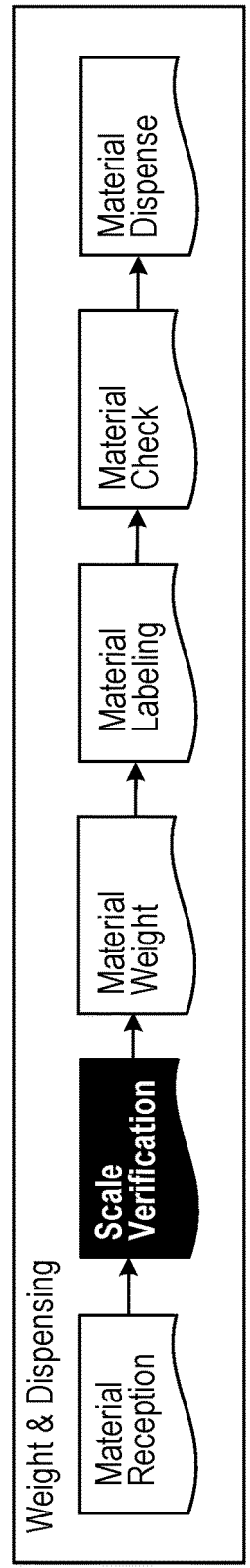
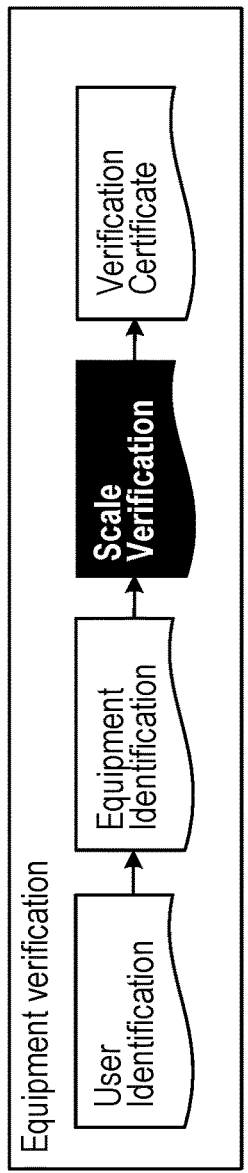
FIG. 15

List of Process Definition

| Process | Related processes | Views |
|---|---|---|
| Product Reception | View Guide & BOM | Manufacturing |
| View Guide & BOM | Product Reception | Manufacturing |
| Wheight | View Guide & BOM | Manufacturing |
| Labelling | Labelling - Wheight | Manufacturing |
| Dispensing | Dispensing | Manufacturing |
| Mix | Mix | Manufacturing |
| Compress | | Manufacturing |

View data on real time

Values for Wheight

| Element | Value | UOM |
|---|---|---|
| Product X | 156.5 | kg |
| Pallet 4134 | 245.6 | kg |
| Tare X | 25.8 | kg |
| Scale | MT-3514 | unity |
| User | John Smith | unity |

Manufacturing View
List of processes
Element association

FIG. 24 http://www.bigfinite.com

Manufacturing View

List of processes

Element association

List of Process Definition

- Maintenance lines
- Packaging view
- Manufacturing view
- ⊞ Product Reception
  - ⊞ View Guide & BOM
    - ☑ Wheight
    - ☐ Labelling
  - ☐ Dispensing
  - ☐ Mix
  - ☐ Compress
- Water control

Search element Row Material

| Solid Product | Raw Material | Pallet Weigher | |
|---|---|---|---|
| Clean Room A | Corridor | User A | |
| Scale MT T-4134 | Clean Room | | Bags |
| Manometer M-441 | Termometer T-4134 | Hygrometer H-4134 | |

INPUT
Solid Product
Raw Material
Pallet Weigher
Clean Room A
Corridor

WHILE
Scale MT 4134
Clean Room
Manometer M-44
Termometer
Hygrometer

OUTPUT
Bags counter
Pallet Weigher
Clean Room D
Corridor
Manometer M-443

FIG. 25

Override Record

| Data source | Temperature sensor 131552 |
| --- | --- |
| Object Type | Device |
| Magnitude | Temperature |
| From | 12/Dec/2014 16:24:34 |
| To | 12/Dec/2014 16:30:34 |

User Login
- User name / account
- Available PGP accounts: joseph.gurmet@bigfinite.com ▶
- PGP Password
- Reason of change

[Accept] [Cancel]

| Current Values ▲ | New Value | Time stamp ◆ | Select |
| --- | --- | --- | --- |
| 25.6 | | 12/Dec/2014 16:24:41 | ○ |
| 25.7 | | 12/Dec/2014 16:24:42 | ○ |
| 25.4 | | 12/Dec/2014 16:24:43 | ○ |
| 25.4 | 25.4 | 12/Dec/2014 16:24:44 | ○ |
| 25.3 | | 12/Dec/2014 16:24:45 | ○ |
| -25.4 | | 12/Dec/2014 16:24:46 | ● |
| -25.5 | 25.5 | 12/Dec/2014 16:24:47 | ● |
| 25.6 | | 12/Dec/2014 16:24:48 | ○ |
| 25.7 | | 12/Dec/2014 16:24:49 | ○ |
| 25.8 | | 12/Dec/2014 16:24:50 | ○ |
| 25.3 | | 12/Dec/2014 16:24:51 | ○ |

MANAGING DATA FOR REGULATED ENVIRONMENTS

CROSS-REFERENCE TO RELATED APPLICATIONS

This is a continuation application of U.S. application Ser. No. 15/018,828, for Managing Data for Regulated Environments, which was filed on Feb. 8, 2016, now U.S. Pat. No. 10,901,962, which claims the benefit under 35 U.S.C. § 119(e) of the filing date of U.S. Patent Application No. 62/113,217, for Managing Data for Regulated Environments, which was filed on Feb. 6, 2015. This application also claims the benefit under 35 U.S.C. § 119(e) of the filing date of U.S. Patent Application No. 62/129,485, for Establishing Associations Between Electronic Records Based on Their Natural Attributes, which was filed on Mar. 6, 2015. The foregoing applications are incorporated here by reference.

BACKGROUND

This specification relates to managing data. In particular, managing data for regulated environments.

Particular industries, for example, the pharmaceutical industry, need to manage transversal information derived from supply-chain activity in a manner that covers all the stages that may require saving data in a repository for regulatory purposes.

SUMMARY

In general, one innovative aspect of the subject matter described in this specification can be embodied in methods for managing regulated data that include the actions of collecting data from a plurality of sources; analyzing the data; and providing one or more outputs based on the analysis. Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

In general, one innovative aspect of the subject matter described in this specification can be embodied in systems for managing regulated data including one or more computers configured to perform operations including: receiving data from each of a plurality of devices; analyzing the received data; and providing one or more outputs to one or more computers based on the analysis.

In general, one innovative aspect of the subject matter described in this specification can be embodied in methods that include the actions of obtaining a collection of data, the collection of data including raw data and envelope data; and processing the collection of data according to particular comparison criteria to identify natural associations in the collection of data. Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 14 is a block diagram illustrating an example of configured connections.

FIG. 15 is a block diagram illustrating an example of different views sharing the same process.

FIG. 21 is an example user interface showing device maintenance activity.

FIG. 22 is an example user interface showing data acquisition from device maintenance activity.

FIG. 24 is an example user interface showing a list of processes included in views and associated objects with values acquired in real time.

FIG. 25 is an example user interface showing an example process definition with objects associated in INPUT, WHILE and OUTPUT phases.

FIG. 27 is an example user interface showing overriding data activity.

FIG. 31 is an example user interface showing device status monitoring.

Like reference numbers and designations in the various drawings indicate like elements.

DETAILED DESCRIPTION

1. Introduction

Figure 1:
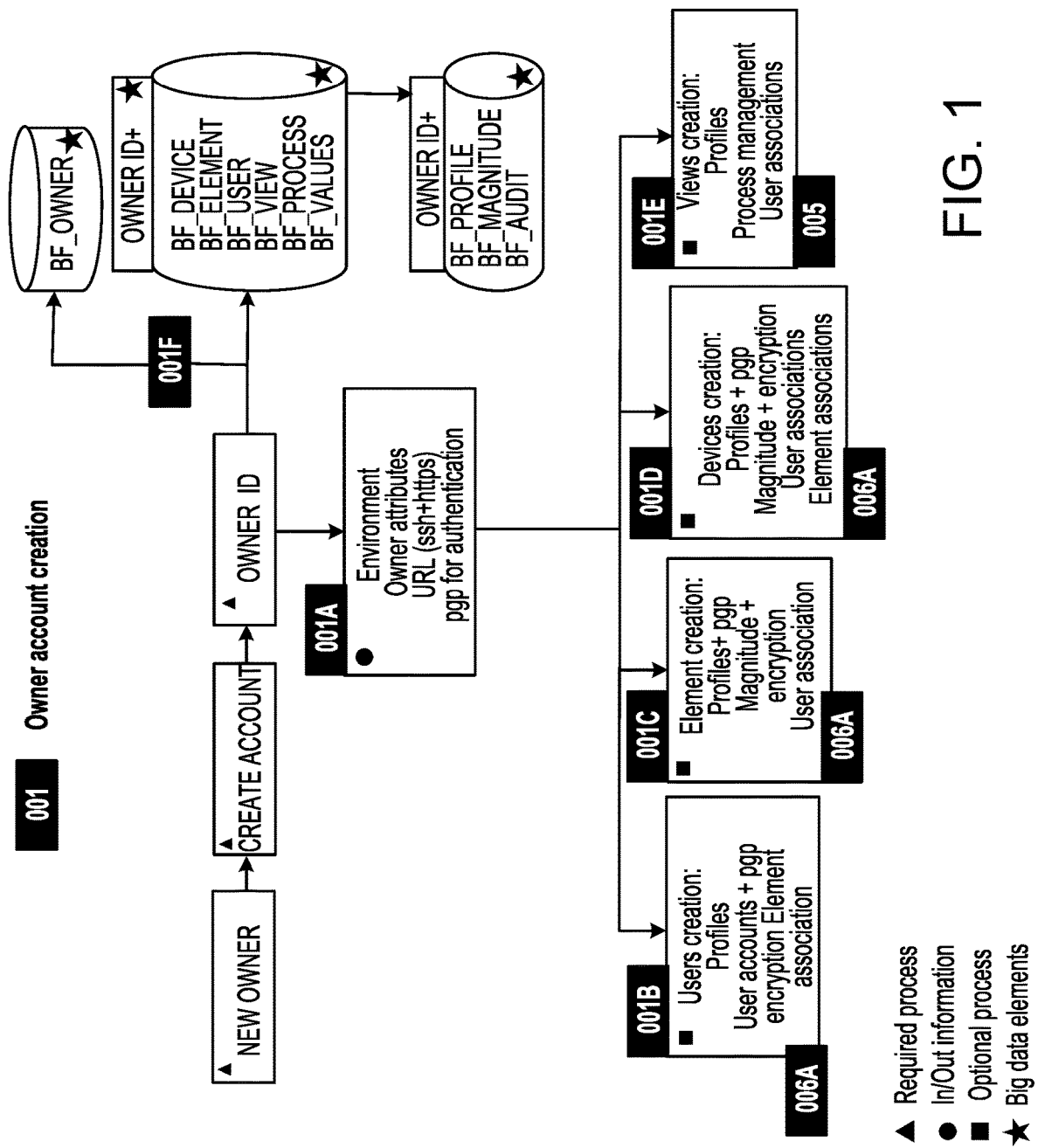
FIG. 1 is block diagram illustrating an example of account creation.

The subject matter described in this specification arises from a need in the pharmaceutical industry to manage transversal information derived from supply-chain activity, covering all the stages that require saving data in a regulatory repository. From an informational point of view, this specification provides a global solution for a number of industries including pharmaceutical industries based on an innovative framework that encompasses: Internet of things (IoT), Big Data, and Cloud Computing. When industries work with innovation, performance, reliability and traceability, huge amount of data, and low cost, they need to delegate resources to big data solutions. The main guidelines that have been defined in the specification to provide a valid solution to the different casuistries are based on the following characteristics:

Data must be recorded by the solution ensuring 21 CFR Part 11 compliance. [21 CFR Part 11 is a FDA code where is described how to proceed with electronic records for regulated environments. US FDA, "Pharmaceutical cGMPs for the 21st Century: A Risk-based approach. Final report". September 2004.

The management of the information must be simple.

The obtained knowledge, achieved in an easy way.

Provide a set of standard tools allowing to shift the user's value.

Cover any need related with traceability, monitoring, modeling and research to get knowledge from raw data stored in a regulated environment.

Mass storage based on big data and cloud architecture.

Delegating power data processing to the system ensuring the security and privacy (based on Private Cloud, encryption, data obfuscation . . . )

Ability to transform information to knowledge through industry standards.

Getting cross-process information through using human queries (like Google search)

Provide information management tools to Reporting, Business Intelligence and interdepartmental disciplines.

Support for compliance with Annex 15 of the GMP. Monitoring and decision making exception: OOS (Out of Specifications) and OOT (Out of Trending). [Annex 15 of the GMP describes the validation and qualification processes for equipment on the rules Governing Medicinal Products in the European Union. Annex 15 can be found at [[http://]]ec.europa.eu/health/files/gmp/2014-02_pc_draft_gmp_annex.pdf, which states that "Representational State Transfer (REST) is a software architectural style that defines a set of constraints to be used for creating Web services. Web services that conform to the REST architectural style, called RESTful Web services (RWS), provide interoperability between computer systems on the Internet."

Support for the implementation of the 3 ICH: Q8, Q9 and Q10. [ICH is the acronym of International Conference on Harmonization (of Technical Requirements for Registration of Pharmaceuticals for Human Use). This conference delivered different guides. The mentioned guides in this document can be accessed from these references: "ICH Q8, Pharmaceutical Development. November 2005," "ICH Q9, Risk Management. November 2005" and "ICH Q10, Pharmaceutical Quality Systems, Step 3. May 2007." The preceding references are incorporated here by reference.

Software licensing based on considering this product as a SAAS or PPU Tool. SAAS is the acronym of Software as a Service. More information available at [[http://]]en.wikipedia.org/wiki/Software_as_a_service, which states that "software as a service . . . is a software licensing and delivery model in which software is licensed on a subscription basis and is centrally hosted. It is sometimes referred to as "on-demand software," and was formerly referred to as "software plus services" by Microsoft. SaaS is typically accessed by users using a thin client, e.g. via a web browser." PPU is the acronym of Pay Per Use.

The elements described in this specification also describe a software application. The features described in this specification aim to be the reference standard to capture the primary information for processing into high-level knowledge in, for example, the biotech and pharmaceutical industry. The overview at high level of the general features provided by this features described in this specification are listed below:

The platform is based on cloud and is a web based application.

Integrates any suitable kind of information coming from different data sources in just one repository.

The platform ensures the authenticity of the data source, enveloping each unit of received information with a set of attributes that add the regulatory requirements.

The system provides a standard way to save and to record the primary data.

The common repository is based on big data technologies

The uploaded information can be monitoring on real time from the platform.

The application allows to analyze results correlating variables and given the needed information to perform multivariate analysis as predictions as well.

Users can provide their own associations over the data sources, although the system establishes default relationship among records.

The system incorporates mechanisms to characterize heterogeneous processes in a homogeneous way through dimensionless vectors.

Users can add rules of activities in the system when data is incoming in the repository. Depending on the logic associated to each data source, different actions are triggered.

A set of different data sources and associations could be grouped under a view restricted by time ranges.

To reference this platform throughout this specification, it will be referred to as a Regulated Data Engine and it will be abbreviated as RDE.

The RDE is a solution based on cloud, big data and Internet of Things that integrates all process information and actor's activities, for example, for biotech and pharma manufacturing products. The uploaded information comes from the different elements that could provide relevant data to the system. In the traditional informational approaches, systems are focused in isolated targets: software to manage resources, LIMS (Laboratory Information Management System) for quality control in laboratory, Scheduling software, ERP (Enterprise Resource Planning), MES (Manufacturing Execution System), WMS (Warehouse Management System), monitoring and OEE (Overall Equipment Efficiency), etc. These tools are very specific and frequently work in an isolated way with dedicated interfaces between systems. The RDE allows to work in the same scenario, with the current applications already installed, but integrating the information in a clever way.

The RDE does not focus its activity in the batch, or in the product nor in the final user. It works with all product and process information using big data to get knowledge. The access to each kind of information is configurable depending on the user profile.

2. General Aspects Overview

The RDE is a big data, IoT and cloud-based application that can be used to integrate any data generated in the supply-chain and interact naturally with other existing records in the system. All processes designed to obtain and manage data are designed and implemented to meet the regulatory requirements of the pharmaceutical and biotech industry. Additionally, users can add their own association's criteria to induce new relationships based on manufacturing standards (ISA 88 and 95) and process management. The concept of supply-chain in this document is not delimited exclusively to the traditional manufacturing process for drugs. The meaning of supply-chain in this document is a wide overview about all process that are joining in the medicine production. Hence, R+D tasks, scale-up, clinical trials, medical prescriptions, medicine's distribution, patient dispensing or treatments follow-ups activities are intended to be covered under this terminology. ISA is the acronym of the Instrumentation, Systems and Automation Society. This organization has published different standard proposals and the referenced in this document are: "ANSI/ISA-88.01-1995 Batch Control Part I: Models and Terminology" and "ISA 95.00.03 Enterprise-Control System Integration, Part 3: Models of Manufacturing Operations Management," which is incorporated here by reference.

The RDE uses technology based on big data to provide powerful techniques for computing and searching stored information. The RDE introduces basic tools that allow the publication of primary data from site's equipment, devices with connection ability, web applications and other electronic systems working under secure conditions. All information is treated under a strict regulatory perspective, making raw and primary data into signed records with an origin certificate.

The RDE allows real time monitoring while both critical and not relevant information is being recorded in the system. All data can be accessed for immediate human generated queries by pre-defined reports and online built queries.

Thus, the RDE offers to the biotech and pharma industry the particular tools to manage information and to transform it into knowledge. Some examples about these kind of tools are described in the following:

PAT (Process Analytical Technologies) implementation monitoring and recording raw data in real time.

Mechanism to study deviations, claims and other non-quality investigation activities in an efficient way.

PQR (Product Quality Review) preparation in a procedural way to get information based on fast operations Batch release in real time getting at the same time the batch report associated to the batch production.

Linking batch data throughout the entire process, getting thereby the batch's e-pedigree. In this sense, the RDE offers a solution to integrate data from research and development (R+D) until the distribution and the final dispensing to the patient.

Supports real time data acquisition to cover the continuous batch production. The monitoring process evaluates the OOS (Out of Specifications) and OOT (Out of Trendings) to make the right decisions in each moment.

Provides critical information coming from different processes, from R+D to the product distribution in an integrated and unified way.

Cost reduction in the information management.

Pharmaceutical and Biotech companies are currently facing the same challenges as other sectors have found:

Prevent vital information loss

Integrate different data sources for knowledge

Manage the large number of records produced in the site

Standardize processes and reduce costs associated with managing information

Find tools to implement these tasks with rapid implementation

Integrate different data sources currently not connect assuming a low cost

Be competitive using the main resource of the company: information.

In addition the pharma industry (including food and cosmetics) must fulfill special requirements regarding the treatment of information:

Ensuring regulatory compliance when obtaining the data and the operation and knowledge acquisition Operations traceability Keep the integrity of acquired data as well as the used channel, from the data source to its storage.

Standards of regulatory compliance management system access to both users and devices (e.g., 21 CFR Compliance)

Quality assurance monitoring and reporting systems

Both the system and the procedure should be subject to validation.

3. Brief Overview

This section describes the different workflows that show, in a summarized way, how the information is managed in the RDE.

Figure 2:
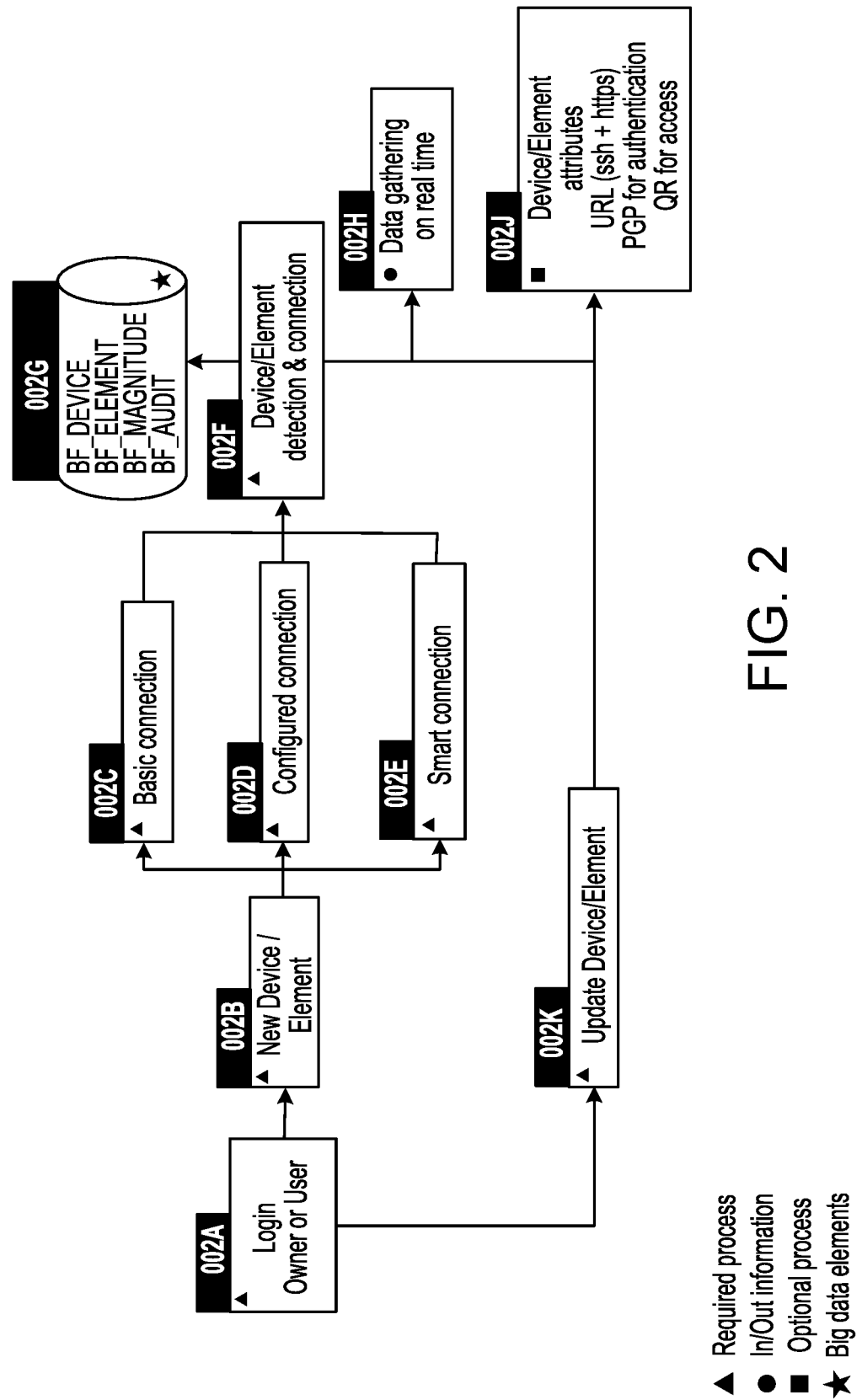
FIG. 2 is a block diagram illustrating an example of device and element association.
Figure 3:
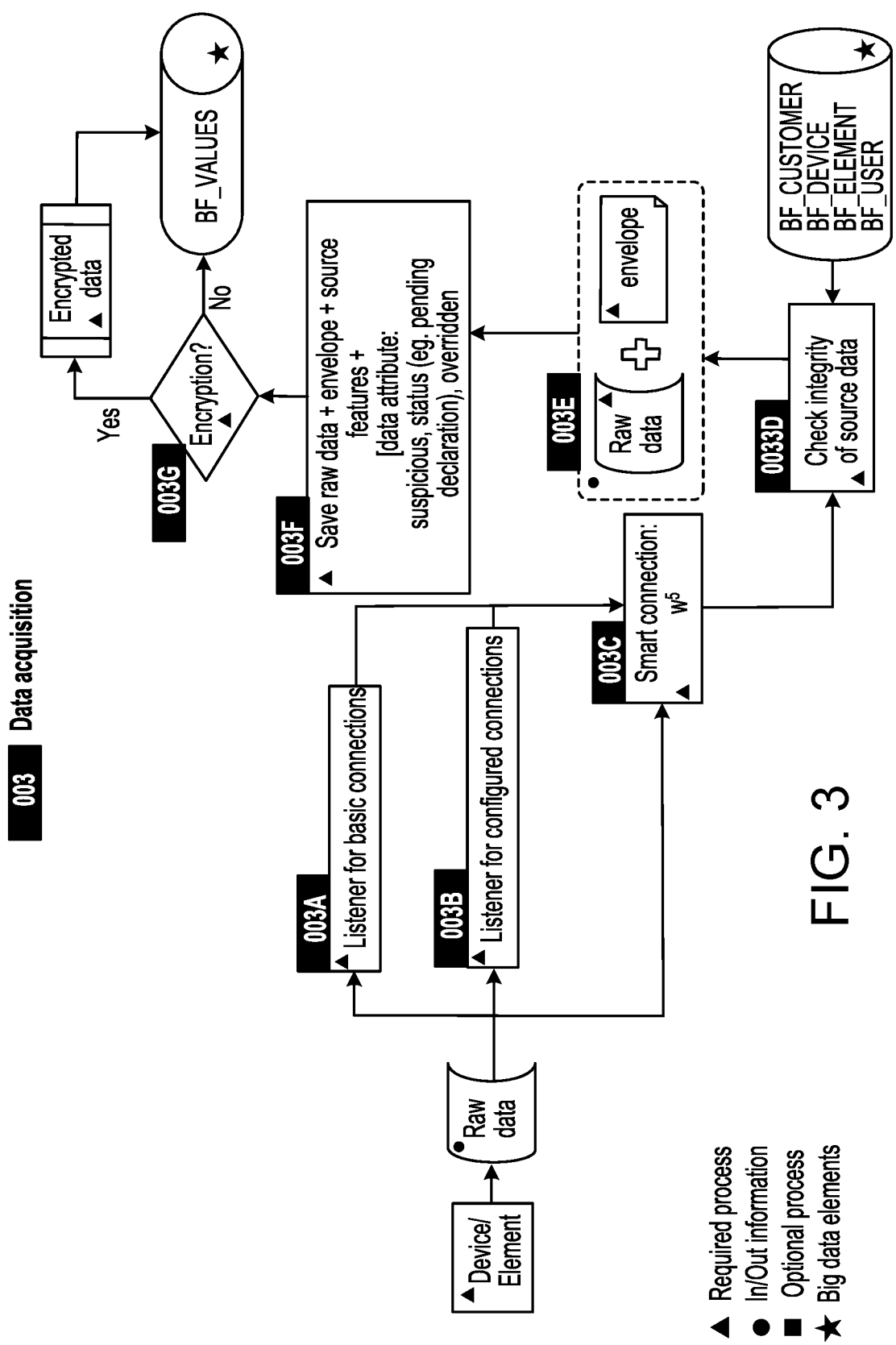
FIG. 3 is a block diagram illustrating an example of data acquisition.

The workflows, e.g., as described with respect to FIGS. 1-3, can be considered together as part of a main process to associate devices to the RDE. The initial process that guides the users to associate devices within the system follows the schema shown in FIG. 1.

The rest of workflows describe the set of operations needed to manage raw data from different perspectives: authentication for value access (write/read) under a regulatory point of view, data management to upload raw data, and processes to create relational links between data to provide knowledge.

FIG. 1—Owner Account Creation

The owner concept is a main driver that allows to create a global environment from a proprietary point of view. An owner must be understood as the proprietor of the set of elements that will feed the site model. A multinational pharma company or a small biotech, for instance, should be associated to this concept.

Once the owner has been created (this process is associated to an account in the system), the RDE assigns a unique identification (named beID as abbreviation of the RDE ID) and creates all the infrastructure (tables and records) associated to this owner.

Behind an owner there is a human being (usually with administrator rights) that configures its environment. As he/she is a person, the authentication can be managed through Pretty Good Privacy (PGP) encryption, delegating the password location outside the RDE. Nevertheless, the system is the owner of the authentication policy (both for owner and for associated users and elements as well). Therefore the 21 CFR part 11 layer is applied inside the RDE and projected to elements that require to be managed under regulation.

FIG. 2—Device and Element Association

A user/owner with access rights must declare devices and elements in the system to allow to send data to the RDE. There are 3 types of devices that can be identified in the system: raw equipment (e.g., a scale, pH-meter and any device with simple digital output), configurable devices (modern measurement devices with applets, High Pressure Liquid Chromatography (HPLC) equipment, etc.) and smart devices (smartphones, Arduino cards, Google Glasses). The elements include concepts like software applications or OPC UA Servers. OPC UA is the acronym of OLE for process control Unified Architecture. It is an industrial communication protocol for interoperability developed by the OPC Foundation. For each case it is necessary to configure the connection type to establish communication with the RDE.

Once the device/element has been created, the RDE assigns to it a unique ID. User can add attributes to this equipment/element to provide more intelligence to the device. This action is not required at this moment, but advisable. When properties are provided to the device, it is necessary to assign the type of data (measure, magnitude or meaning of information that will be sent). If not defined at the beginning, attributes can be added or updated afterwards.

FIG. 3—Data Acquisition

The data gathering process is centralized in the RDE server that listens for https/ssh calls. The incoming calls are based on REST services which use JavaScript Object Notation (JSON) elements to pass complex objects. REST is the acronym for Representational State Transfer. It represents a specific software architecture. More detail is described in the reference: en.wikipedia.org/wiki/Representational_state_transfer, which states that "Representational State Transfer (REST) is a software architectural style that defines a set of constraints to be used for creating Web services. Web services that conform to the REST architectural style, called RESTful Web services (RWS), provide interoperability between computer systems on the Internet." Received data can be simple (single values) or complex (objects nested in the value) and follows a standard template. The structure of this message covers the upload information across all the supply chain process in a new and innovative way.

Each received data is wrapped with an envelope provided by the system. Worth noting the mechanism on how data is wrapped in a standard way with special attributes that provide a regulated meaning to each recorded value.

Figure 4:
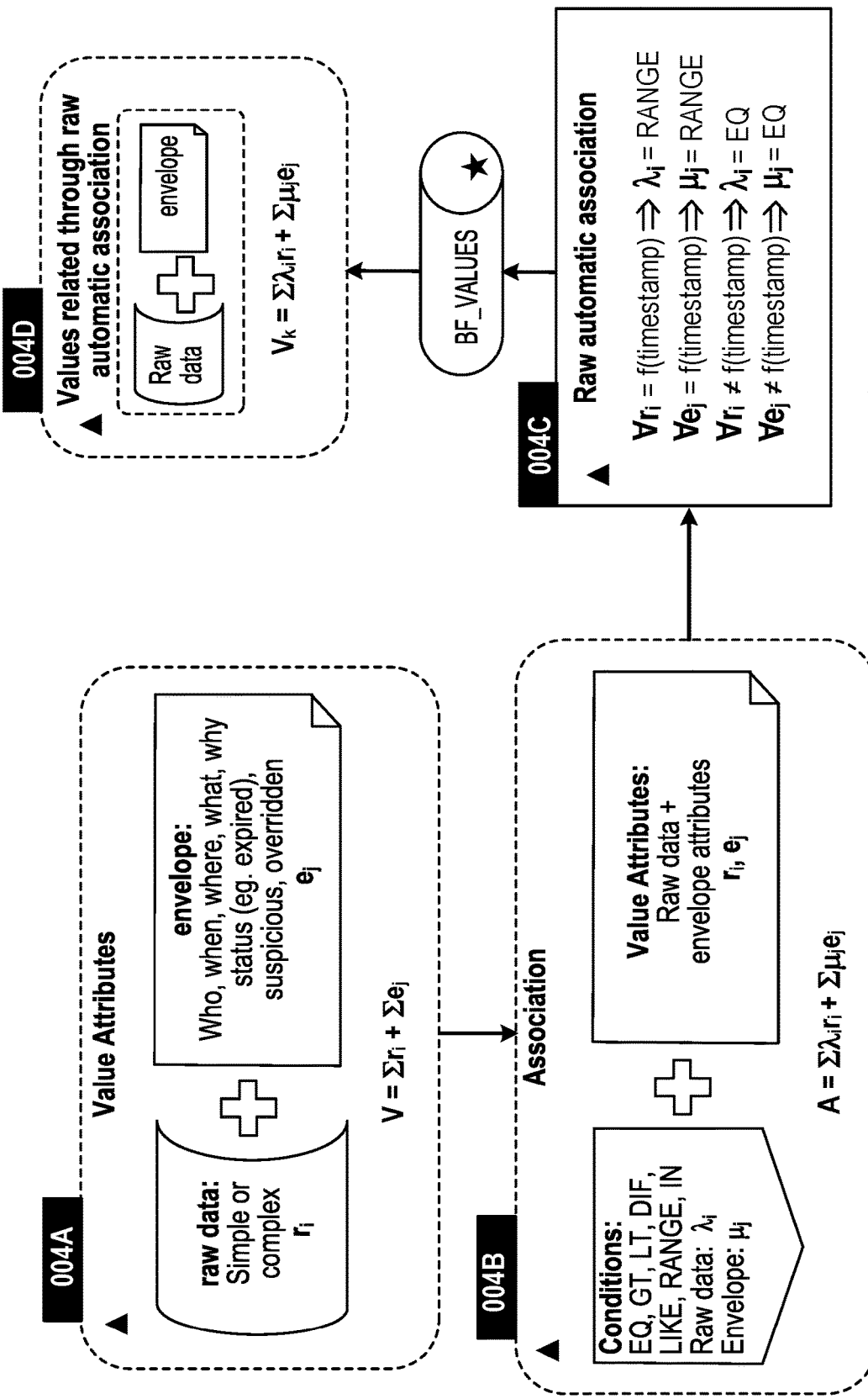
FIG. 4 is a block diagram illustrating an example of data association.

FIG. 4—Automatic Data Relation. Natural Association

When raw data reaches the system, an envelope with relevant information is added individually to each record. When users need to acquire knowledge from the information stored around data, the RDE provides a natural way to relate records each other stored in big data. The criteria used to relate information is formalized in the presented algorithms. The natural data association is based in the envelope that the system provides to each individual record.

Figure 5:
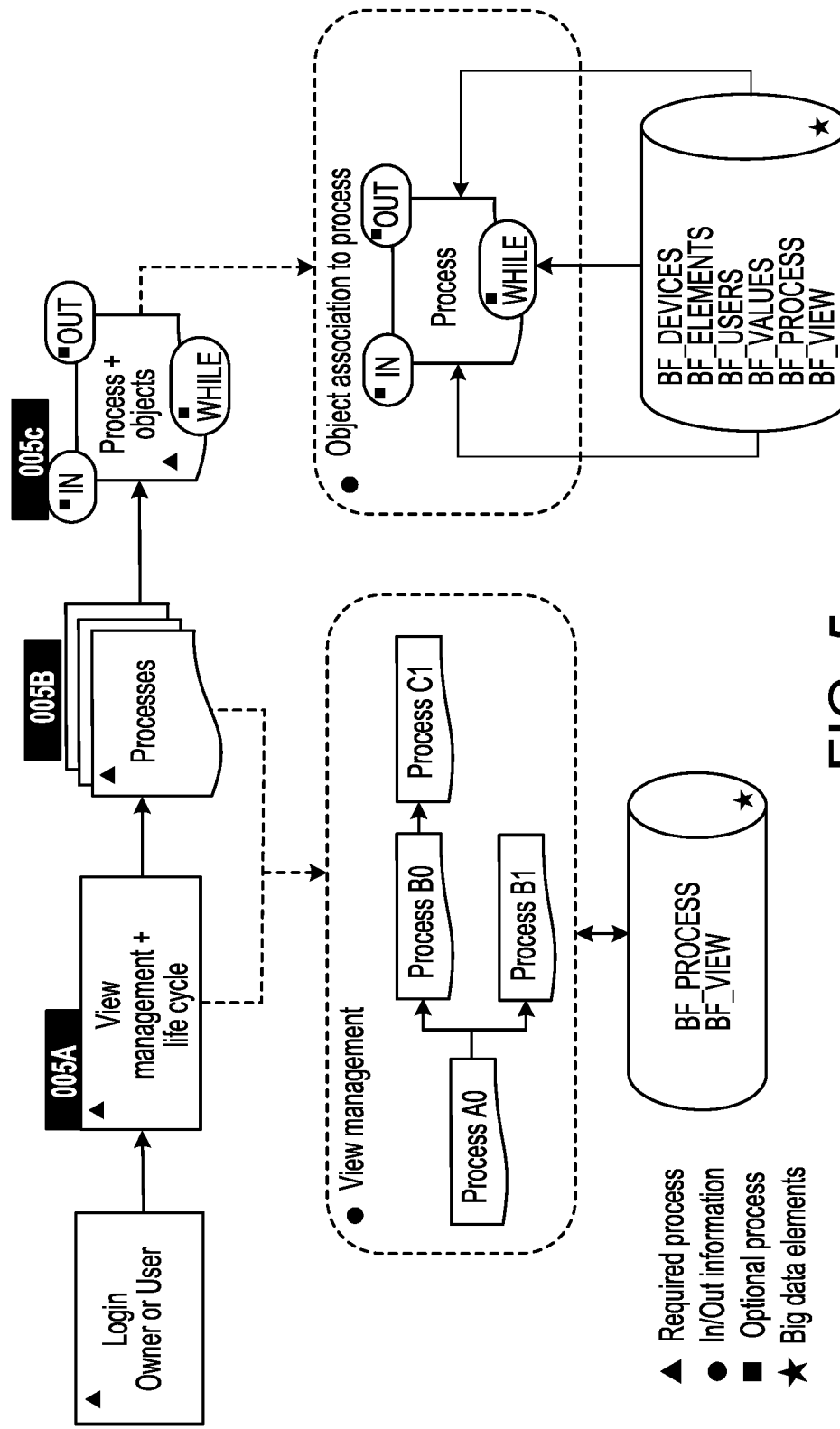
FIG. 5 is a block diagram illustrating an example of views, processes, and objects association.

FIG. 5—View Process Management

The system provides a natural method of association of primary data (e.g., as described with respect to FIG. 4—Automatic data relation). However, users can create their own relationships of information through several channels. The view of process generation is a possible way. A process view is a sequence of operations designed by the user where the phases to be executed are represented. Each individual process has three stages in addition to allowing to atomize the sequence of execution. As differential point, notice that the process is not considered from the perspective of classical black-box and it becomes a transparent-box including the WHILE stage. This step allows to ensure that this scheme is a facilitator for the implementation of ICH Q8, specifically the development of monitoring techniques related to the process (PAT concept). This is also a way of implementing the requirements of Annex 15 of the GMP.

Figure 6:
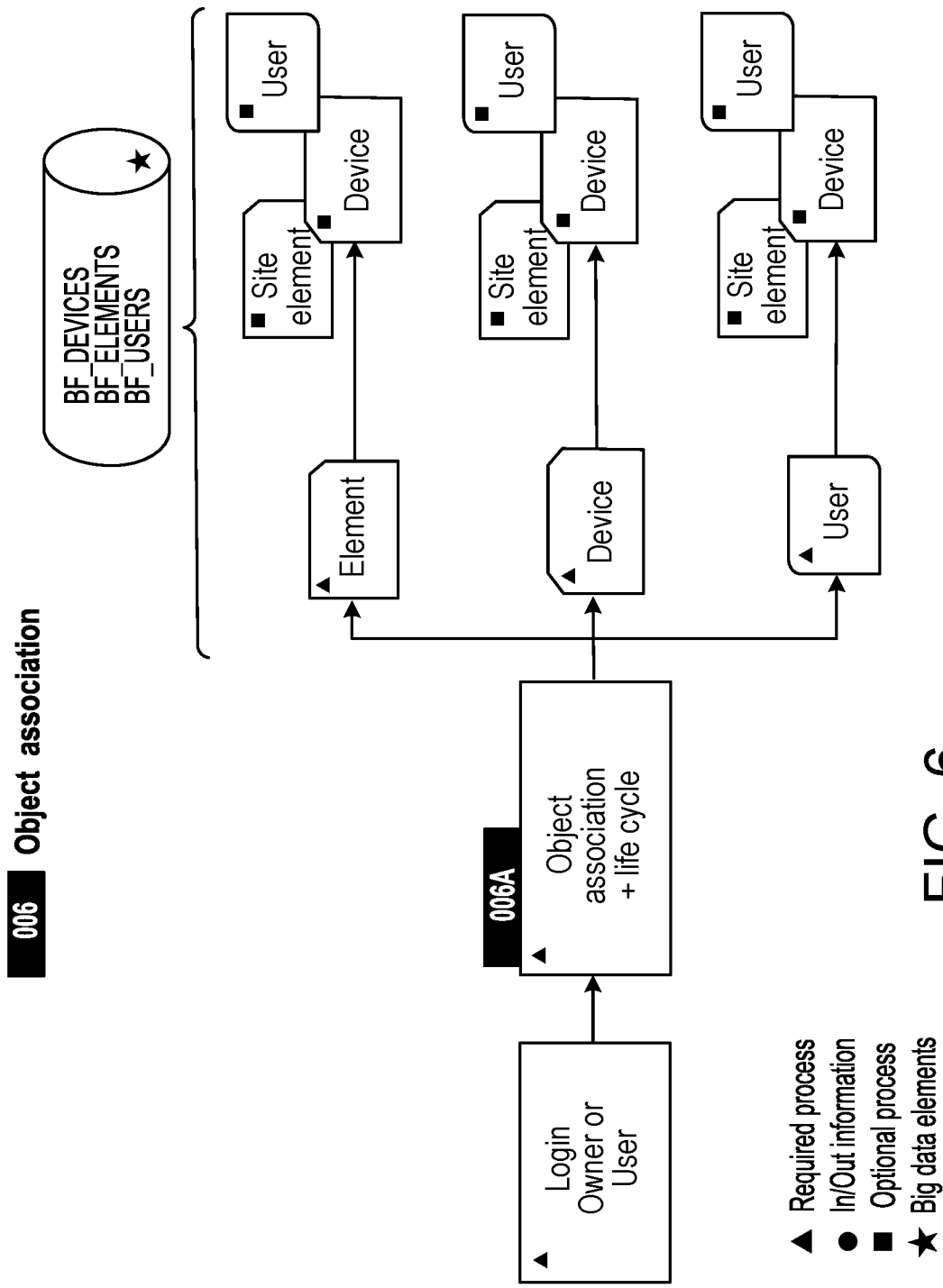
FIG. 6 is a block diagram illustrating an example of objects association.

FIG. 6—Object Association

This is the second way that the user has to create relationships outside the definition of system data. Through the association of objects (site elements, devices and users) links, between the different elements of the system completely independent of the data being recorded in real time, can be defined. Through hyperlinks, the data sources may be associated with objects, creating for instance relationships for hierarchies, functional, containments, procedurals, etc. It is important to highlight the fact that the origin of the data is not violated at any time. It is the hyperlink to the content that is used to establish relationships between different knowledge elements to consider.

One patient, a medicine's prescription, raw materials, a warehouse, a white room, a scale or an operator could be objects that can be categorized within these relationships. The link between elements will result in a relational system that depends on the particular interests of each user.

Figure 7:
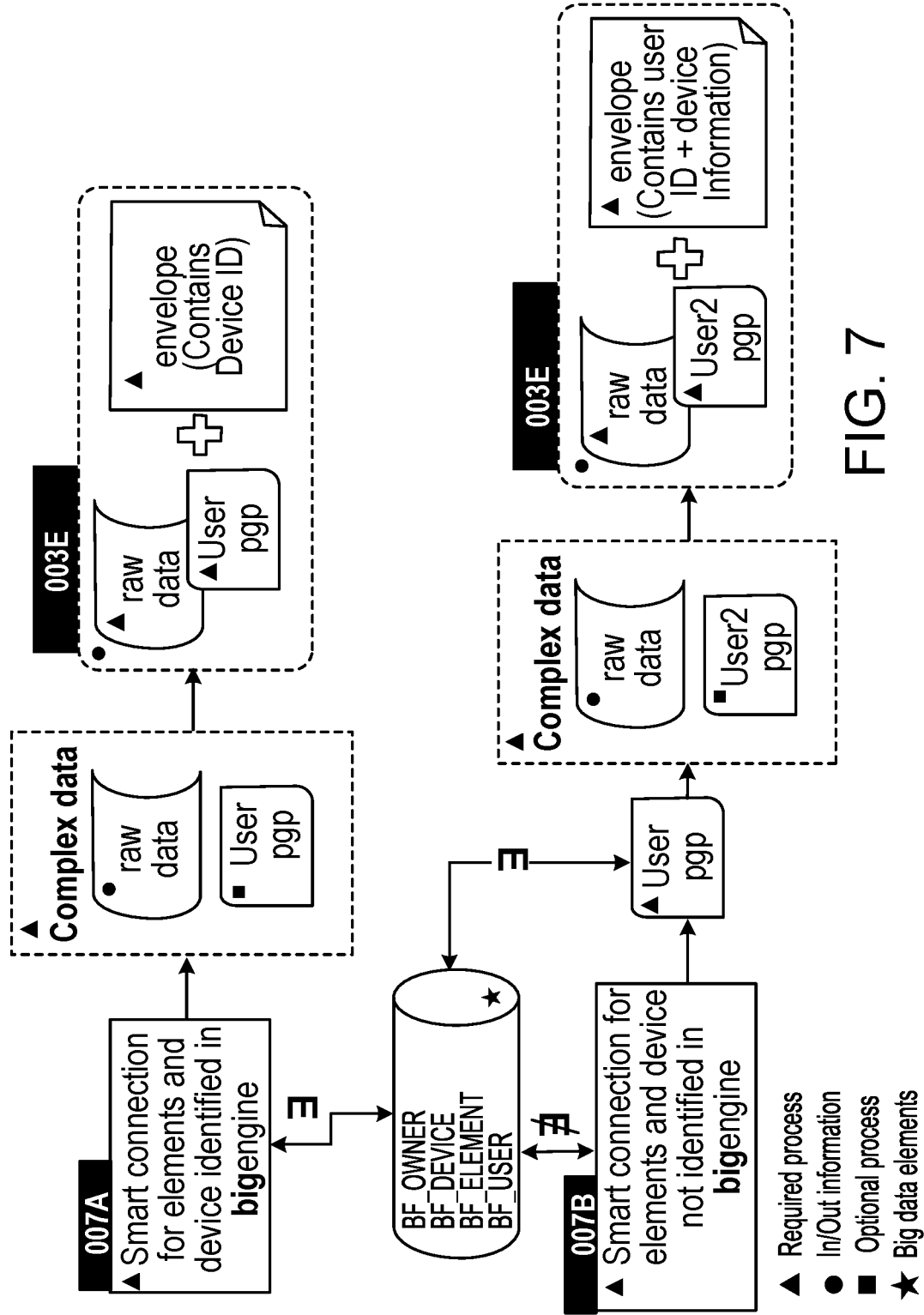
FIG. 7 is a block diagram illustrating an example of data emission.

FIG. 7—Data Emission with Required Authentication

A mainstay in the treatment of the data, from a regulatory point of view, is to ensure the authenticity of the origin of the data. The RDE is built to ensure this feature of the records when they reach the system and the actions that may occur on them. It is considered that all the data received by the system can have only two types of sources: human (users)

and not humans (devices and information systems). This workflow describes the mechanism provided within the RDE to ensure the authenticity of the data according to the two mentioned ways.

Figure 8:
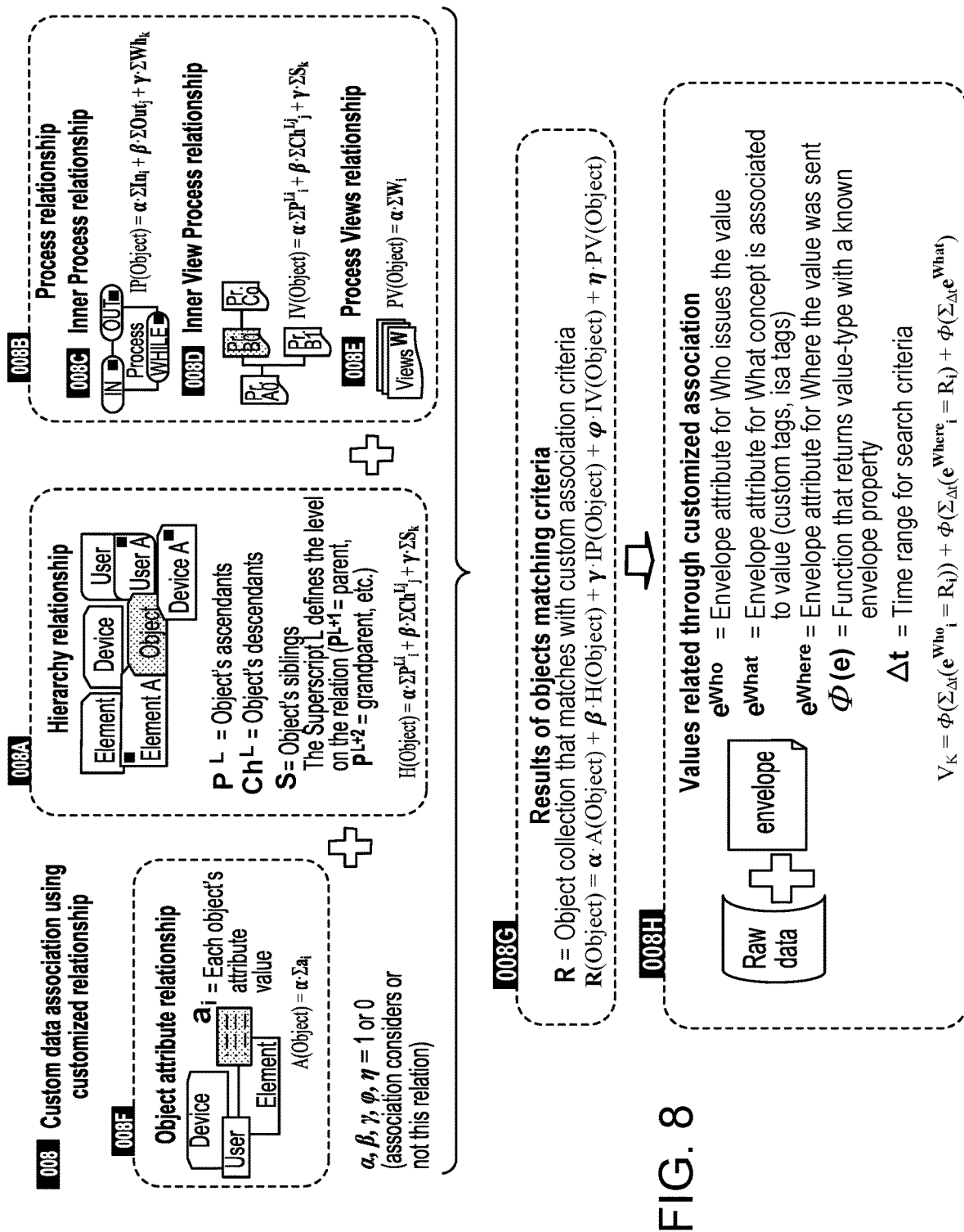
FIG. 8 is a block diagram illustrating an example of data association using customized relationships.

FIG. 8—Custom Data Relation

FIG. 4 (Automatic data relation) describes the natural system proposed by the RDE to associate the information based on the attributes related individually with each figure. Within this figure it defines the algorithms used by the system to match the information according to the different possibilities provided to the users. Through the relational engine users can exploit information using the criteria established in the association of custom models (processes and object associations).

FIG. 9—Scenarios

The data published in the platform by an owner is defined for exclusive access by the elements that belong to this owner (user, site elements and devices). Nevertheless it can be defined a special publishing's degree for data allowing its accessibility from others environments outside of the private sphere of each owner. Thus the administration, regulatory entities, owners or partners may have partial access to the environment, by logging in to data that has been defined as public for a given environment. These settings are defined in the system as scenarios and public views are set for each owner in order to make visible only data that has been configured for this purpose.

FIG. 10—Agents

The application programming interface (API) provided by the RDE allows to have the information in real-time for tasks such as monitoring processes. Additionally, to provide information for decision making outside the system, the system has a set of alerts and triggering actions for establishing controls in real time. This element is an immediate mechanism for managing situations of alerts depending on individual values received on-line through the system. Alarms can be set by absolute values or trends; they can also be compared with individual values (e.g., numbers) or complex expressions (e.g., drug administration).

4. Detailed Description of the Illustrative Implementations

Each figure contains different elements that are described in detail in this section. To facilitate the understanding of the descriptions some examples have been included. This examples should not limit the scope of the implementation and they should be considered as direct use cases that could be implemented using the RDE system. Additional use cases and implementation opportunities are also described.

4.1. Owner Account Creation

The content of this section is described with reference to FIG. 1.

The owner creation is the first step to generate the environment of connection between the different objects that require to integrate their information into the platform. The considered sub-processes in this figure are the following:

001A. Once the owner name has been verified (it is unique in the RDE), an environment is created and associated to this owner. This user for the client is assigned as administrator by default for his environment. All needed tables to maintain the information content are created in a private way. They are for exclusive access of this owner and all of them are prefixed with the owner's name, ensuring the uniqueness.

An owner is the proprietary of a system account. There are a set of properties that can be assigned allowing to define properly the account (personal information, economic data, payment format and additional information required to define it). There are some special features that should be interesting to remark:

To activate an owner and to make effective its associated environment it is required to get a PGP key that will be managed in a regulated way following the rules of the 21 CFR part 11 and GMP as described in the Regulatory Layer section.

The owner's name and its properties are stored outside of its private environment to ensure the persistence of the information such as the uniqueness of its identification. The table BF_OWNER is used to manage the information of the owner concept.

Once the owner is activated (all data has been properly filled and the user linked to the owner has a public PGP key stored in the RDE), he can start doing transactions into the environment using ssh and https protocols.

All transactions always will be performed through the public API available in the system and only when the user has been properly identified.

An example representation of an object of type owner is transcribed as shown below:

---
Definition 1: owner definition owner:
{
  beID, Name, Description, email, Social and Commercial
  information, activity, customized tag[ ], geolocation
  Security:
  {
    Public PGP key, Public key for CRC, expiration time
  for password
  }
}

---

001B. Ina collaborative work environment where different people are involved it is necessary to create definitions and profiles for users (they are different individuals than the owner). Thus the user owner will able to create other users with data already related to their private environment. The identificative user's data and its status will be modifiable always by an administrator. This administrator can provide an administration profile to other users as well. A user can access the system through the published API as long the user has a public PGP key and it is valid in the RDE. The assignment of this key to the user is made in the same way that the one described for owner: following the guidelines defined in the 21 CFR part 11 as on the GMP as well (see Regulatory Layer section).

There are a set of important properties associated to the user object:

The system allows to assign configurable permissions to each user by assigning profiles.

Users have a special attribute named public. This property gives the opportunity to make visible data which is associated to this user on scenarios designed for this purpose (referenced in the FIG. 9 where Scenarios are presented).

The property encryption determines whether associated data to a given user properly defined in the system has to be encrypted inside RDE. When primary data is received through the API and the call includes a user with this attribute (with or without electronic signature), the raw data is encrypted inside the table BF_VALUES (referenced in 003G within FIG. 3 below).

The property forScenario assigns a specific access for users that can only work with scenarios. Users that have this property assigned as forScenario=yes, cannot access to any other feature of the RDE platform except for those scenarios where this user has been declared.

The table used to manage the user's information is BF_USER.

Once the user is activated (all its data has been properly populated and the user has a public PGP key stored in RDE), he can start doing transactions on the environment using ssh and https protocols.

All transactions always will be performed through the public API available in the system and only when the user has been properly identified.

Some examples of users on the system could be site's operators, researchers, production manager, doctors, patients, pharmacist, distributors, administrations, etc.

The representation of a user is transcribed in the following way:

---
Definition 2: User definition
---
User:
{
  beID, Name, Description, email, personal information, picture, customized tag[ ], public, forScenario, status
  Security:
  {
    pgp, Id Profile, effective date, encryption, expiration,
  }
}
---

001C. An element is an abstract object or a real one related with the medicine's management which is not a user or a device. The elements can send information to the RDE (real element with connectivity) or they can constitute grouping concepts for functional or hierarchical collections. Real elements with connectivity could be considered for instance software applications, OPC servers, a database trigger, a file or a document based on cloud (e.g., Google Docs). Some examples about real elements without connectivity could be manufacturing areas, workcells, silos, storage locations, a paper notebook in the laboratory, the prescriptions notebook of a doctor (with numbered pages), a recipe, a stability trend, etc.

All elements that represent collections of other objects that are sharing properties (functional, hierarchical, containments of whatever relationship that describe the reality) can be considered as abstract elements. Thus, the Device concept (understood in the most generic way) that has a set of attributes that could be inherited by all the devices related with the original concept, is also considered as an abstract object. In a similar way, a clinical trial could be an element that collects the different actors involved in its execution. A medical prescription also could be classified as an abstract element. There are a set of important properties associated to the elements:

Elements have a special attribute named public. This property gives the opportunity to make visible data which is associated to this object on scenarios designed for this purpose (referenced in FIG. 9).

The property encryption determines whether the associated data to a given user properly defined in the system has to be encrypted inside the RDE. When primary data is received through the API and the call includes a user with this attribute (with or without electronic signature), the raw data is encrypted inside the table BF_VALUES (referenced in 003G within the FIG. 3).

The table used to manage the user's information is BF_ELEMENT.

Those elements that have mechanisms to include PGP keys (e.g., different software applications located in the same server could use its own keys) will store its public key in the RDE. This public key will be used to verify the authenticity of the received data in a direct way. This feature is managed through the element's pgp property.

The elements have also the availability to be defined as critics (for some task) through the property criticity. All elements defined with this attribute require electronic signature when they update information in the RDE (reference in section Regulatory Layer).

The system allows to assign configurable permissions to each element by assigning profiles. Hence users have access to the data issued by elements only if they are sharing the same profile that the element has.

The activation of an element is made by assigning the value Enabled on its property status and ensuring that it complies with the effective date (or it is null). If the object is not enabled, the data already received by the system can be saved, but all this data will be qualified as incoming from a non-activated object.

All elements that are sending information to RDE must have an assigned magnitude. It gives physic sense to their values (value-type concept). Thus an element could have associated more than one data source. This design provides a solution to the possibility that, for instance, a software application identified as element, could issue values for each type of specific measure related to the application. For this reason, each magnitude has a separated configuration for the data acquisition (set of properties identified by DataAcquisition). In this complex attribute it is saved the information associated to the data source that links the origin of the data with the object. Some examples about magnitudes of elements could be:

The element Raw Material can be measured in a weight magnitude and to be defined with the kg unit of measure.

The element Dose could be measured through pills/day.

The representation of a user is transcribed in the following way:

---
Definition 3: Element definition
---
Element:
{
  beID, Name, Description, ISA95/88 tag, customized tags, picture, geolocation, public, movable, encryption, status, criticity
  Security:
  {
    pgp, ID Profile, ID user approval, expiration, effective date, encryption
  }
  magnitude:
  {
    ID, Name, Description, UOM, public, customized tags, status
    DataAcquisition:
    {
      beID, Source reference, Data access type (file, ws, serial port, USB port, sheet, DB, ...), call sentence, customized tag, status
    }

| Definition 3: Element definition |
|---|
| Security:<br>{<br>    ID Profile<br>}<br>}<br>} |

001D. The Device concept under the RDE's context applies to any physical device capable of emitting digital information when it is captured through standard mechanisms. Depending on the architecture, the devices have different types of connectivity (see FIG. 3—Data acquisition), being specific modules required to drive the primary non-standard data (e.g., data sent through the serial port via OPC UA, universal serial bus (USB), global system for mobile communications (GSM), etc.). There are a number of remarkable properties associated with the object device:

- The devices have a special attribute called public. This property grants the ability to make visible the data that is associated with this object in scenarios designed for this purpose (see FIG. 9).
- The property encryption determines whether associated data on the equipment must be encrypted within the RDE. When primary data is received through APIs called from a device as source of the data, with the attribute encryption, the information is encrypted in the table BF_VALUES (see element 003G in FIG. 3, below).
- Devices that have the mechanisms to incorporate PGP (e.g., smartphones, RF (Radio Frequency) terminals, hardware based on Arduino, etc.) will have a public key to verify the authenticity of the origin of the information received in a secured way. The property is managed by the pgp attribute of this object.
- The system allows to assign configurable permissions to each object by assigning profiles. This will limit the user access to individual devices depending on the profile used to act on them.
- The activation of a device is done by assigning the value Enabled to their property status and ensuring that it complies with the effective date (or it is null). If the object is not enabled, the data already received by the system can be saved, but all this data will be qualified as incoming from a non-activated object.
- A device that sends information to RDE must have a physical interpretation that gives a magnitude to the values. Thus a device may be associated with more than one source of information (e.g., a device to measure heights and diameters of bottles, a sensor that emits temperature, pressure and humidity, etc.). This design responds to the possibility that a device can issue different values where each of them are associated to a specific magnitude or unit of measure. For this reason each magnitude is related with a possible configuration of data acquisition (group of properties identified by DataAcquisition). This property stores complex information associated with the data source that links the origin of the information with the device. Features such as the IP and the port in the https/ssh call, the browser from which the call was made, the operating system, Mac Address or International Mobile Equipment Identity (IMEI) for a smartphone are some examples of the identification of the primary data origin.

The table is used to manage this information is BF_DEVICE.

The representation of the object element is transcribed as follows:

| Definition 4: Device definition |
|---|
| Device:<br>{<br>    beID, Name, Serial Number, Description, Trademark, Manufacturer, Distributor, ISA 95/88 tag, customized tag, picture, geolocation, encryption, public, movable, status<br>    Security:<br>    {<br>        pgp, ID Profile, ID user approval, expiration, effective date, encryption<br>    }<br>    magnitude:<br>    {<br>        ID, Name, Description, UOM, public, customized tags, status<br>        DataAcquisition:<br>        {<br>            beID, Source reference, Data access type (file, ws, serial port, USB port, sheet, DB, ...), call sentence, customized tag, status<br>        }<br>        Security:<br>        {<br>            ID Profile<br>        }<br>    }<br>} |

001E. In an owner's environment it can be associated the concept of process views. It would not be a usual practice to declare process views during the owner creation, although the API allows to associate the existing views to an owner. The detail about how the process views are generated and their processes are discussed below with respect to FIG. 5.

001F. Once the owner account has been created, different objects can be linked to its environment. This action can also be done later (in fact, this is the natural way). For each associated object, the RDE checks that the uploaded device, the user and the element or view is unique in the system. Each object is identified as unique by its name. This check is performed against the content of the tables BF_PROFILE, BF_USER, BF_DEVICE, BF_ELEMENT and BF_VIEW. When objects are associated to an owner, an internal identification (named beID) is assigned and related to a hyperlink used to access the object.

001B, 001C i 001D. Users, devices and elements can be linked each other through hierarchical structures. These customized relations provide additional rules to establish associations between values and data sources. The specific way about how objects can be associated are described in the FIG. 6.

4.2. Device and Element Identification

Figure 12:
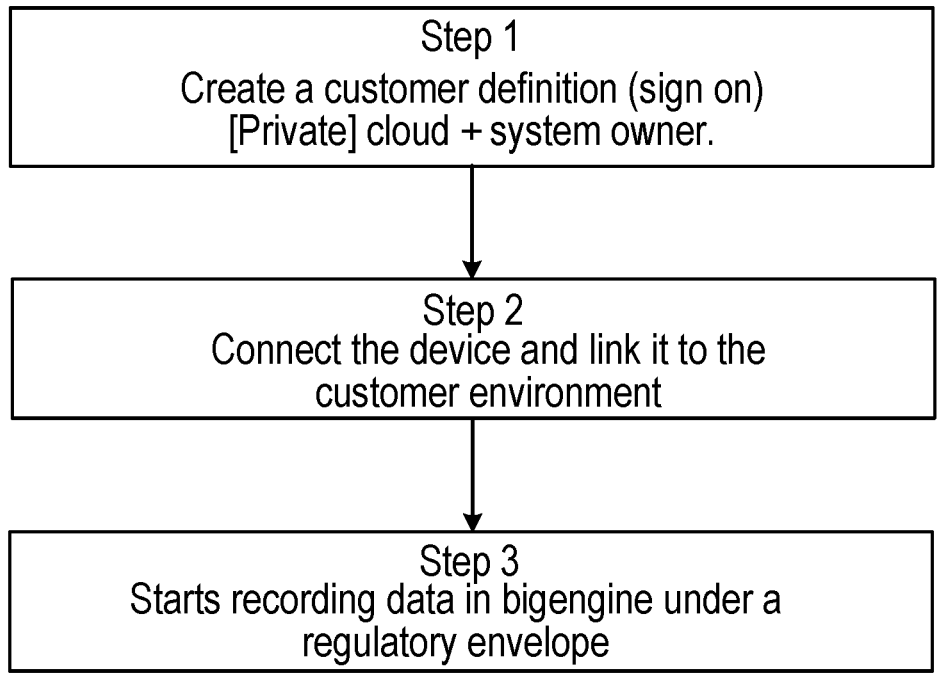
FIG. 12 is a flow diagram of an example method for device connection.

The content of this section is referenced to FIGS. 2 and 12.

This process constitutes the second step to connect a device to the system and upload its generated data. The detailed procedure followed by the system is described as follows.

002A. Users with a valid account in the system must login. Owner and/or users associated to this owner are considered as valid when their status is active. Each personal account is associated to a pgp key that is checked when the users login in to the RDE. The internal procedure followed by the system to ensure the authenticity of the users is described in the Regulatory Layer section.

002B. Authenticated users with the right permissions (the owner has the administrator profile by default) can associate devices or elements to the owner's environment. The specific APIs CreateNewDevice and CreateNewElement enable to execute this action. This APIs must be called providing the parameter that defines the type of connection used by the device or element. There are three types of expected connections:

Basic. This connection type is applied to devices that only have the ability to outcome digital data in a rough way as, for example, equipment that send values through serial or USB port, GSM, plain files, etc. To convert primary data in https/ssh calls and send it to the RDE it is necessary to provide a middleware that works as conversor (additional detail below with respect to element 003A of FIG. 3). This type of connection is characterized by equipment that are not able to execute https/ssh calls, delegating thus this feature on the middleware.

Configured. Devices and elements that are able to do https/ssh calls but cannot perform these actions directly, they need to be configured. This configuration requires to identify and configure how data will be listened. The engine that will be installed in the element works as a tunnel, reading values in the input of a channel and writing them to a https/ssh call (additional detail below with respect to element 003B of FIG. 3). An OPC Server, a data base that could implement triggers, a software application that could be configured to send data or to install a listener that reads by a known channel and send the information to the RDE are some examples of this type of connection.

Smart. When a device is able to host a small application and run it, this connection could be classified as smart. Devices like smart phones, web servers or tablets could be potential devices to be associated to RDE under this definition (additional detail below with respect to element 003C of FIG. 3).

Once the user has defined the connection type to be assigned to the new device, the required configuration needs to be applied for each case.

Figure 13:
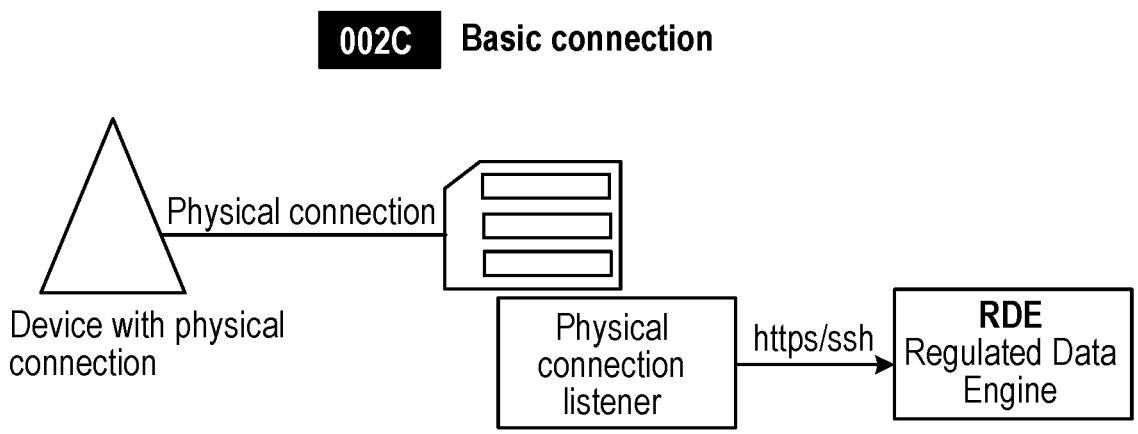
FIG. 13 is a block diagram illustrating physical connections.

002C. The basic connection (FIG. 13) requires a middleware implementation that could be downloaded from the RDE.

The middleware must be installed in a system that allows to run a Java thread. This system must centralize the physical connection with the device that needs to send its information. Usually the port and the physical parameters associated to this port must be defined to establish this connection. These parameters are included in the device identification in the middleware, as other properties that the user could include to provide a more accurate definition. Once the device has been properly defined within the basic connection, the equipment's output could be displayed to check the consistency of data that will be sent to the RDE. When the configuration is accepted, the physical connector listener will send the raw data acquired from the physical connection to the RDE using the standard API calls. The data source transmitted in the messages is a set of the following connection attributes:

Physical connection properties (physical local port—like com, USB, parallel —, connection properties—like parity, bauds, speed —, characteristics of the message treatment—like split rules for the incoming data—and other properties associated to the device that could be sent to the physical connection.

Network and system properties for the element that assists the messaging between the device and the RDE. The mac address, the IP and port, and the current user logged in the system are part of the system identification that provide the channel and execute the API calls.

002D. A configured connection (FIG. 14) works as a listener associated to an application, transforming electronic information originated in the software and sending it to the RDE automatically.

The middleware must be installed in a system that allows to run a Java thread and can be downloaded from the RDE environment, being valid only for the owner environment from where it has been requested. The listener is configured defining the root of the data that will be sent. A file or a portion of it, a table from a DB, a web service that is sending data or a Google Document are examples of data sources that could be configured through this middleware. This configuration is associated to the device/element and stored in the RDE. When the API is called to send the primary information gathered by the listener, the information associated to the software that generates the data is sent too. In a similar way that the source identification is sent through a basic connection, the data source transmitted in the messages is a set of the following connection attributes:

Software or electronic object properties (logical location—like a full path—, software properties—like the name, provider and version —, characteristics of the data processing—like trigger, scan frequency—and other properties associated to the software element that could be sent to the configured connection. Some examples about this kind of elements are a camera, a pen drive, a data base, files created by applications, Google documents or web services.

Network and system properties for the element that assists the messaging between the configured software and the RDE. The mac address, the IP (IPv4 and IPv6) and port, and the current user logged in the system are part of the system identification that provides the channel and executes the API calls.

002E. The smart connection is the natural way to send information between systems and the RDE. In fact basic connections and configured connections ultimately call this smart connection (through the middleware). The link among objects and the RDE is produced doing standard API calls using https or ssh calls, ensuring in this way the encryption of the data sent through the network. A set of public API could provide the mechanism for accessing to this information. This type of connection is used by third parties and applications that are able to do https and ssh calls. Therefore, devices that can generate these calls have only to be associated to the RDE for the owner environment that needs to work and automatically the system will check its authentication origin.

One device could belong to more than one owner environment (e.g., tablets used as notebooks in pharmacies or smartphones working in a distribution partner). In this case, the device should be associated to each owner to be identified properly in the desired environment.

To associate a device with a smart connection in the RDE it is necessary to access the web environment linked to the current owner and do a click in the new smart connection from the new device. This action will generate a request from the device to the RDE with the required information associated:

Physical hardware identification. This could be the IMI for smart phones, a mac address or an associated serial number.

Custom information. Additionally to the physical hardware information, a logged user can add the information needed to provide the required singularity to the equipment.

002F, 002G. The devices created in the system are verified against the information existing in the owner's environment where they have been generated. The check of the object's uniqueness is made against the data existing in data engine (002G). Users are properly notified if devices already exist. Once the devices and elements have been verified and associated to the owner's environment the objects are ready to send information. The sending of the data from the objects can be done through API calls (e.g., smart connections) or through the configured middleware (basic and configured connections). From this moment, data is sent calling the InsertValue method and is inserted in the data engine (BF_VALUES table), matching the data's origin for each individual value. Data is saved with a state which depends on the object's situation that generate them (additional detail below with respect to element 003F of FIG. 3). Thus the connection is verified and the data issued by the devices is available.

002H. Once the devices have been properly saved in the owner's environment, the data sent by these devices can be saved in the RDE by calling the InsertValue method. The data coming from well identified equipment always is saved in BF_VALUES, including an envelope that wraps the values. This envelope provides the additional attributes when the data is saved in the system (additional detail below with respect to element 003F of FIG. 3).

Thus the data received from an equipment that has been disabled, is saved in the system but with a flag that identifies the origin as not enabled. From a conceptual point of view, all the incoming information must be recorded, adding to the values all the parameters that help to classify the state of the data source. Hence, the values issued by equipment can be queried in real time.

002J. The incorporation of data transmitters in the RDE requires only the identification of the device and a verified connection. All transmitters additionally have a unique identifier assigned by RDE. This identifier, called beID (RDE ID), is assigned by the system once made the required uniqueness checks. When the connection is verified by the user (e.g., by monitoring the received data in real time—see 002H—), it is convenient to provide to the device all the necessary information to properly characterize its function. This customization is also appropriate to search and to establish relationships between different elements of the owner environment.

The action of associating additional attributes to the element or device can be realized at the same time that the object is linked to the owner environment or even a posteriori (through the action of the corresponding update to 002K). It is advisable however, to establish a minimum number of properties that allow properly recognize the device at the time of assigning the device at the beginning of the linking with the owner.

The attributes that allow characterizing elements and devices are described through Definition 3 and 4 (Element and Device definitions respectively). It is important to remark some non-obvious attributes:

ISA 95/ISA 88 tags: They are standard labels that are already catalogued. The users can associate these tags to objects and incorporate the set to the system. Some examples of these labels could be Enterprise, Site, Area, Process Cell, Unit Process, Production Line, Storage Zone, Unit, Work Cell Storage Unit, Equipment Module Control Module Bill of Resources, Bill of Materials, Product, Reactors, Weighers, Recipe, Formula, etc. The concept of Process and Process Segments do not correspond to assignable tags because the Process concept already exists in the RDE model.

Customized tags: These labels are defined by the user. As tags are defined, the system stores them in a specific way that allows to suggest them in subsequent assignments. Examples of tags that can be customized could be ambient sensors, white area sensor, clinical trial results, etc.

Encryption: Determines whether the data received from this object are stored under the encryption algorithm in BF_VALUES. The encryption of the data ensures that the information is masked under the structure of big data and can only be decrypted by requests to the system (as the rest of method calls are) with the appropriated encryption key (this is the differential point with an unencrypted call). More information about encryption is provided with respect to element 003G of FIG. 3.

Public: Determines whether the data originated in this object can be published on scenarios. The data is incorporated into the RDE and must always be associated with users, devices or elements properly identified in the system. By default, the data can only be viewed by users associated with the owner environment and not externally. However, a source of information can be configured in order to share data with users that have not access to the entire owner environment but do for limited frameworks of information. These scenarios can only display data defined as public and from each scenario it can be set which data will be visible and its range of display (e.g., for dates). For each scenario, additionally, users must be associated with access to the data (see the detail below in the Scenarios section).

Status: An object has an associated state that determines the state of the data that is updated in the system. Since the state is a property variable in time, the data takes the value of the object state that originates it at the moment it is included in the RDE.

PGP: It's the PGP public key associated with the pair generated by the object.

002K. The actions described in the previous section (002J) are executed at the time of the identification of the device/element of the owner. The same actions are available through the API once the owner has been created.

4.3. Data Acquisition

The content of this section is described with respect to FIG. 3.

FIG. 3 describes, as a key element of the data acquisition, the message structure used to send the raw data's information, as well as the envelope's structure that the RDE uses to provide intelligent information to the recorded value.

003A, 003B. The data acquisition process is centralized through the action of sending https/ssh calls to the RDE. Both basic and configured connections (threads 002C and 002D of FIG. 2) drive the activity of the middleware associated to the physical connections towards the structured messages dispatching with the data source native information as well as its value.

003C. This process sets the standard method for the raw data sending to the RDE. It's based in a JSON message with a specific structure that is named beJSON ("be" as used herein is an acronym of the RDE), whose structure follows the following template:

Definition 5: JSON structure to send primary data as standard. This structure is named beJSON

```
{"Data": {
    "Value":[{"Primary":        V,
              "Result":          [V],
              "UOM":             V,
              "<X>":             [V]
             }],
    "Who":{
        "PrimaryOrigin":         V,
        "Target":                V,
        "DevicePublicId":        V,
        "DeviceInternalId":      V,
        "DeviceHash":            V,
        "ElementPublicID":       V,
        "ElementInternalID":     V,
        "ElementHash":           V,
        "UserPublicID":          V,
        "UserInternalID":        V,
        "UserHash":              V,
    },
    "When":{
        "RealTime":              V,
        "ForcedTime":            V,
    },
    "Where":{
        "Location":              V,
        "Longitude":             V,
        "Latitude":              V,
        "Altitude":              V,
        "Accuracy":              V,
        "Speed":                 V,
        "Slope":                 V,
        "IPLocationCountry":     V,
        "IPLocationRegion":      V,
        "IPLocationCity":        V,
        "IPLocationISP":         V,
    },
    "What":{
        "Action":                V,
        "ValueType":             V,
        "Magnitude":             V,
        "CustomTags":            [V],
    },
    "Why":{
        "Meaning":               V,
        "ReasonOfChange":        V,
    }
}}
```

Where the description of each tag is shown below:

TABLE 1

Field definition for the beJSON used as standard to send data

| Tag | Req. | Array | Description |
|---|---|---|---|
| Data.Value | ✓ | ✓ | Value or set of values that must be inserted into BF_VALUES. If a message is received without this tag in its beJSON structure it will not be considered valid and therefore will not become part of the system. |
| Data.Value.Primary | | ✓ | It's the data's native value. If the value is a binary file, its B64 representation would be in this tag. If it would be a string received through a weight in a COM port, it would contain all the received bytes. |
| Data.Value.Result | | ✓ | Contains the processed information contained in Data.Value.Primary. In the most general case, this value matches Data.Value.Primary and therefore it is not required. However it may be needed a processing of the primary data to get an outcome. Thus, for an image, the associated result could be the associated text to an OCR process, or in the case of a weight, the result would be the numerical value of the weight. |
| Data.Value.UOM | | | Corresponds to the data's measurement unit. It may be the case that the contents of the field Data.Value.Primary presents also the unit, but may be required to include it in a dedicated field. |
| Data.Value.X | | ✓ | Additional attributes may be required to add more information to the value. The message includes the ability to add customized characteristics for each value. |
| Data.Who | | ✓ | This tag includes all the information related to the physical and/or logical origin of the primary data as well as the source that can had transformed the primary value to obtain its outcome and its measurement unit. |
| Data.Who.PrimaryOrigin | | ✓ | All data has a primary origin and its identification should be assigned to this value. This is a required field so that, if the message is received without this value, RDE will extract from the http/ssh request header the associated source information with at least the IP and port from where the data comes. |
| Data.Who.Target | | ✓ | The information set emitted by the objects towards the environment where all the data is integrated should be reported in the message. This target matches with the owner's environment identification where the records are collected. |
| Data.Who.DevicePublicID | | | If the data emitting device has a unique public identification, this should be specified in this field. The smartphone IMEI or a device serial, if specified by the manufacturer, is an example of this. This value is checked against the existing BF_DEVICE records. |
| Data.Who.DeviceInternalID | | | Internal identification (under the owner's environment context) of the device that emits the data. In the case of smartphones the name that the user has defined can be assigned. For devices where an identification name can be manually defined, this valued cloud be assigned to this field. |

TABLE 1-continued

Field definition for the beJSON used as standard to send data

| Tag | Req. | Array | Description |
| --- | --- | --- | --- |
| Data.Who.DeviceHash | | | Hash associated to the device authentication. For RDE it is an encrypted string related to the device pgp key. |
| Data.Who.ElementPublicID | | | In equivalence with the devices, it corresponds with the element's unique public identification that generates the data. The MES app name and its assigned license could be an example. Another example could be the used browser and its version. |
| Data.Who.ElementInternalID | | | Similar to the device's private identification definition, this field describes the data's originated element as being defined as customized. |
| Data.Who.ElementHash | | | Hash associated to the element authentication. For RDE it is an encrypted string related to the element pgp key. |
| Data.Who.UserPublicID | | | Identifies the user accountable of sending or generating of the data. An email, a bigfinite account or a SSN are candidate values to designate a user. |
| Data.Who.UserInternalID | | | By analogy with the other internal identifications, this value corresponds with a custom name that could match with the user's last name and first name. |
| Data.Who.UserHash | | | Hash associated to the user signature. For RDE it is an encrypted string related to the user pgp key. |
| Data.When | ✓ | | This tag is associated to the timestamp about data was created. |
| Data.When.RealTime | ✓ | | The true timestamp value associated to current value. It is based on coordinated universal time (UTC). As this tag is required, if it is not present in the message, RDE assigns the current timestamp when message is received. |
| Data.When.ForcedTime | | | This field mission is to set the timestamp for data that has been generated in a time previous to the current one. Used, for instance, for initial data loads or for sending past records that were generated in a previous instant where Internet access was not available. |
| Data.Where | ✓ | | Stores the location where the data is produced. |
| Data.Where.Location | ✓ | | General location detected at the message's reception. As a required field, if no information of this field is received, RDE will assign the location contained in the message received via ssh or https protocol. |
| Data.Where.Latitude | | | Latitude associated to the location where data was created. Just for devices that could publish this information. |
| Data.Where.Longitude | | | Longitude associated to the location where data was created. Just for devices that could publish this information. |
| Data.Where.Altitude | | | Altitude associated to the location where data was created. Just for devices that could publish this information. |
| Data.Where.Accuracy | | | Accuracy related with the measurement. Just for devices that could publish this information. |
| Data.Where.Speed | | | Speed of the source data when it was created. Just for devices that could publish this information. |
| Data.Where.Slope | | | Slope of the source data when it was created. Just for devices that could publish this information. |
| Data.Where.IPLocationCountry | | | Associated country to the IP from message is coming. If this value is null, RDE assigns it automatically taking it from the received message. |
| Data.Where.IPLocationRegion | | | Associated region to the IP from message is coming. If this value is null, RDE assigns it automatically taking it from the received message. |
| Data.Where.IPLocationCity | | | Associated city to the IP from message is coming. If this value is null, RDE assigns it automatically taking it from the received message. |
| Data.Where.IPLocationISP | | | Associated company to the IP from message is coming. If this value is null, RDE assigns it automatically taking it from the received message. |
| Data.What | | ✓ | This section of the message gives the reasons about the object of this data. |
| Data.What.Action | | ✓ | Describes the activity associated to this message when value is received. It can take values like insert, update or delete. The used API identifies by itself the type of action to apply in the change (API are called in a different way depending on expected action of insert, update or delete). |
| Data.What.ValueType | | | This is a main field that gives significance to the value. In fact, the value identification is formed by the beID (user, element or device) plus this concept. Thus each value has a valid origin based on this string concatenation: beID + concept. It is not required. That means that if this field is not informed, all values coming from the same source data will be grouped under the same classification. The same device when is issuing different types of values (e.g., a probe that sends temperature, humidity and pressure), could differentiate each value type in a conceptual way by means a specific definition for each type. |

TABLE 1-continued

Field definition for the beJSON used as standard to send data

| Tag | Req. | Array | Description |
|---|---|---|---|
| Data.What.Magnitude | | | Specifies the magnitude with which the data is measured. The most common concepts are the physical magnitudes (such as weight, volume, temperature, pressure, humidity, . . . ). There are other magnitudes not directly related to traditional measures, such as might be "print quality" "symptomatic response to treatment," etc. On the other hand, note that one device could emit reads of different magnitudes. This field allows to differentiate between the various data emitted by the same source. |
| Data.What.CustomTags | | ✓ | Defines the tags that provide additional search value to the data (exclusively to this data). Different custom tags can be associated to users, elements, devices and magnitudes. These custom tags should not be the ones individually associated to the data, because they will be accessible when performing searches through the relationships between sources and values. Examples of custom tags can be, for a camera, "Pallet", "Container" "Box". For a prescription's associated value: "cholesterol," "ClinicalTrial." |
| Data.Why | | | This is the only section not required. It contains the necessary information to justify the existence of the value being updated and is associated with a user's volitional action. |
| Data.Why.Meaning | | | Meaning of the action associated with this value's notification. For example, when changing a value the meaning would be "I'm changing a value." Complying with the legal regulatory requirement.. |
| Data.Why.ReasonOfChange | | | With any electronic signature associated with a critical process it is necessary to describe the reason that causes the change. For example: "I was mistaken when filling this value into the form." |

An example of valid messages issued by a weight (through the middleware that manages the physical connection) could be:

Definition 6: Example of a beJSON with raw data related with a weight coming from a scale

```
{"Data": {
    "Value":[{"Primary":"SS + 4.5 gr",
             "Result":4.5,
             "UOM":"gr",
    }],
```

Definition 6: Example of a beJSON with raw data related with a weight coming from a scale

```
    "Who":{
        "PrimaryOrigin":"192.168.4.31:6773",
        "UserPublicID":"john.smith@bigfinite.com",
        "UserInternal ID":"EUROPE\JOHN_SMITH",
        "DeviceInternalId":"Scale ST-0341",
        "DevicePublicId":"145198741034-B",
    },
    "When":{
        "RealTime":"2014-07-16T19:20:30.45+01:00",
        "ForcedTime":"2014-07-16T19:20:30.45+01:00"},
    },
    "Where":{
        "Longitude":35.6,
        "Latitude":41.5,
        "Altitude":25.6,
        "Accuracy":1
        "Slope": 0.0
        "IPLocationCountry":"USA",
        "IPLocationRegion":"CA",
        "IPLocationCity":"SFCO",
        "IPLocationISP":"Jazz Telecom S.a."
    },
    "What":{
        "Action":       "Insert",
        "ValueType":    "Precission Weigth",
        "Magnitude":    "Weigth",
        "CustomTags":   ["accuracy", "granataria"],
    }
}}
```

In the case of a medical prescription, the corresponding message would look like the following example:

Definition 7: Example of a beJSON with raw data related with a clinical trial prescription

```
{"Data": {
    "value":[{"Primary": "Colestiramina. Brand: Questran |
Dose: 3/day | Indication: Decreases the amount of fat
absorbed from food.
        Lovastatina. Brand: Mevacor | Dose: 1
at night | Indication: Prevents the liver from making
cholesterol.",
        "DoctorName":"Maria Sullivan",
        "DoctorId":"413413",
        "PatientId":"341333-1",
        "PrescriptionReference":"12-PG35"
        "Medicines":[{"Name":"Colestiramina",
"Brand":"Questran", "Dose":"3/day", "Indication":"Decreases
the amount of fat absorbed from food"},
            {"Name":"Lovastatina",
"Brand":"Mevacor", "Dose":"1 at night", "Indication":"Prevents
the liver from making cholesterol."}]
    }],
    "Who": {
        "DevicePublicId":"iPhone_MariaSullivan",
        "DeviceInternalId":"IMEI15132470983741033",
        "UserPublicID":"maria.sullivan@bigfinite.com",
        "UserInternalID":"MARIA SULLIVAN",
        "ElementInternalId":"Safari 5.4",
        "DeviceHash":"HAFDLK134FA",
        "UserHash":"HADFOIUAFFFA",
    },
    "When": {
        "RealTime":"2014-07-16T19:20:30.45+01:00",
        "ForcedTime":"2014-07-16T19:20:30.45+01:00",
    },
    "Where":{
        "Longitude":35.6,
        "Latitude":41.5,
        "Altitude":25.6,
        "Accuracy":1
        "Slope": 45.6
        "IPLocationCountry":"USA"
```

-continued

Definition 7: Example of a beJSON with
raw data related with a clinical trial prescription

```
        "IPLocationRegion":"CA"
        "IPLocationCity":"SFCO"
        "IPLocationISP":"Jazz Telecom S.a."
      },
      "What":{
        "Action":     "Insert",
        "ValueType":  "Medical Prescription",
        "Magnitude":  "Illness",
        "CustomTags": ["cholesterol", "ClinicalTrial"],
      },
      "Why":{
        "Meaning":"Followup in the third month of treatment"
      }
}}
```

003D. The information that determines the origin of the incorporated data in the incoming messages to the system is verified against the existing information in the database in big data. The records that must be valid in order for a message to be accepted are the contents in the Data.Who.PrimaryOrigin and Data.Who.Target tags.

003E, 003F. The data that reaches RDE through a beJSON sent by a https/ssh call executed on the corresponding REST function (for instance the associated function to the records insert is InsertValue). All valid messages that reach the RDE are treated by adding an envelope with additional information to complete the content of the message. Thus, the RDE can complete information on the message's tags that don't come informed (for instance, information related with Data.Where and Data.When). Also the envelope is completed with the following fields:

- beID: To each message a unique identifier is associated in the system which will allow tracing and reference the content within the owner environment as well as outside of it, in case the data may be published in different scenarios (see the detail in section 009—Scenarios).
- status: Characterizes the data with a status that results from the associated context to the record's source. The different status may be: valid (assumed if a value in not assigned), not valid, expired pgp, pending of effective date, pending to define source, aberrant.
- suspicious: When there is a significant change in any of the values that characterize the data's source, the status of "suspicious=yes" is associated to the data. Situations that can determine a value as suspicious may be a non-notified IP or port change, a location's change in the data's source (when the object has not been declared as Movable) or a timestamp in a format different of the ones usually received from the source. When a data is characterized as suspicious, the users with associated elements or devices that generate this value are informed via e-mail. If no associated users are available, the owner's account of the environment's owner is notified.
- overridden: This field has content or is present in the envelope only if the data has been modified. This field contains the link to the value's overwriting detail (new value overwrites the current, with the change's responsible, timestamp, reason for the change and the new value). For more detail see reference in the Regulatory Layer section.
- crc: A signature is assigned to the message to ensure that the content cannot be modified, by checking the bytes of this message to a number that represents them in a coded form.

Thus, the original message that comes with the data is completed with an envelope that provides additional information while supplementing that information that may have come empty. The structure of an original message, once processed by the RDE, is described by the following structure:

Definition 8:
beJSON structure with the envelope
wrapping the raw data

```
{"Data":{
    "Envelope":{
        "beID":       V,
        "status":     V,
        "suspicious": V,
        "overridden": V,
        "crc":        V
    },
    "Value":  [{ }],
    "Who":    { },
    "When":   { },
    "Where":  { },
    "What":   { },
    "Why":    { }
}}
```

003G. The encryption property determines whether the data associated with an element should be encrypted within the RDE. When primary data is received through the APIs that have an element as a data origin with encryption attribute, the information is encrypted into the BF_VALUES table. Notice that encryption means that data is stored obfuscated, it does not make reference to the encryption process while data is sent among data source and RDE (the used channel is secured using https or ssh).

4.4. Automatic Data Relation. Natural Association.

The content of this section is described with respect to FIG. 4.

The values incorporated to the RDE, for example, via REST calls (mainly through the API InsertValue) are asynchronous and are saved independently between them. When users need to relate information through search, RDE provides a natural type of association, as described below.

004A. All values stored in the RDE have associated attributes that have been assigned in origin or once they reached the system, after checking the integrity of the data source (see FIG. 3). It is first necessary to define the nomenclature that will be used to describe the natural association process.

Raw data is defined (identified by the vector r) as the set of information that presents the Data.Value segment of the message (see detail above with respect to element 003C of FIG. 3).

Envelope data is defined (identified by vector $e_j$) as the set of values that provide additional information to the primary data. This information is associated through segments Data.Envelope, Data.Who, Data.When, Data.Where, Data.What i Data.Why (see detail above with respect to elements 003C, 003E and 003F of FIG. 3).

In the base of vectors $r_i$ and $e_j$, a data cannot be considered exclusively as its value, but this value plus the added information through its envelope. For this reason, a value defined by the data source (device or element) plus value-type, has the following expression:

$$V = \Sigma r_i + \Sigma e_j$$

004B. When performing searches on the values of the RDE by natural association default comparison criteria are used. In general, the comparison criteria may be the following: EQ (equals), GT (greater than), LT (less than), DIF (different than), LIKE (like), RANGE (in a given range of values), IN (contained in), CONT (contains) and Ø (not applicable). The comparison criteria may be different by the raw data ($\lambda$) and by the envelope data ($\mu$), as well as different between individual own values in the raw data ($\lambda_i$) and of the envelope data ($\mu_j$). The natural association to determine the relational criterion of a value is formalized with this nomenclature:

$$A = \Sigma \lambda_i r_i + \Sigma \mu_j e_j$$

where the individual comparison criteria for raw data ($\lambda_i$) and for the individual envelope data ($\mu_j$) take one of the mentioned comparison criteria:

$$\{\lambda_i, \mu_j\} \in \{EQ, GT, LT, DIF, LIKE, RANGE, ANY, IN, CONT, \emptyset\}$$

004C. The automatic associations that the system performs when running searches for values (of raw or envelope data associated to $r_i$ or $e_j$) are based on the following allocations to comparison criteria:

For values of raw data or envelope, data that are of timestamp type, the comparison criterion will be by date range ($\lambda_i$=RANGE or $\mu_j$=RANGE respectively).

For any other raw data or envelope data searched value type, the criterion will be compared for equality ($\lambda_i$=EQ or $\mu_j$=EQ respectively).

004D. Once defined the search values ($r_i$ or $e_j$) and the specified the date range on which the sample should focus, the system applies the following criteria to find the system values that comply with the indicated criteria:

$$V_k = \Sigma \lambda_i r_i + \Sigma \mu_j e_j$$

where $V_k$ is the set of values that match with some of the criteria described by $r_i$ and $e_j$, with the comparison criteria $\lambda_i$ and $\mu_j$.

Getting Results Related by the Natural Association

The definition of the comparison criteria (established by the requester or by means the default assignments) determines how the natural association will be applied across the different values that must be considered in the association. For those comparison criteria that need specific values to be applied, such as RANGE (requires the limits between which values will be compared), it is necessary to assign their references. The set of the references and the comparison criterion, constitute the contour conditions of applicability for the requested natural association. Naming C as the contour conditions where the natural association is defined, the list of values that belongs to this association can be expressed by the following sentence:

$$V_k = A_C = E_C \lambda_i r_i + \Sigma_C \mu_j e_j$$

where the suffix C defines the set of contour conditions that delimit the context where values are associated.

The vector $V_k$ establishes the list of values that are related between themselves through the comparison criterion that the requester (or the default assignment) has defined. Regarding the data sources and their generated values, i.e., the origin of each value (V), they can be formalized in this way:

$$V_k = f(S)$$

Where S is the source representation. This expression reflects that values generated by any source have a direct and functional dependency with their origin. For any system closed under the defined constrictions as defined for the RDE, it must exist the inverse of the function f(S) that leads to the following equality:

$$S = f^{-1}(V_k) = g(V_k)$$

Or equivalently, for any individual value, it is possible to find its source. Then, it is feasible to infer that for any beNA, there is a list of sources related between them by means the contour of conditions in this way:

$$S_n = g_n(V_k) = g(A_C)$$

Thus, it is defined the association of entities ($S_n$) that constitute the source of values in a given system that are related between them by means the natural association.

4.5. Processes' Views Management

The content of this section is described with respect to FIG. 5.

The asynchrony in the data's reception allows to establish automatic relationships only like the ones defined above in the discussion with respect to FIG. 4. The system can be used to establish customized relationships between elements, so that additional links to the natural associations that the system provides can be generated. One example of customized relationships is creating processes views, being able to be managed from the RDE's web application by users logged in to the system.

005A. A view is the processes' sequencing according to a specific arrangement. Different views may contain the same processes. For example, in a pharmaceutical manufacturing environment, two independent operations (e.g., the independent views of Weight & Dispensing and the phases of Equipment Verification) may contain the same process as shown below with respect to FIG. 15.

005B, 005C. A process is a step in the execution of a task. The BF_PROCESS table stores the processes created in the owner environment. A processes' view contains the processes' sequential association, allowing many parents, children and siblings for each process.

The differential point that the RDE brings to the processes' design is based on that a process in no longer considered as a black box to become a transparent box. Thus we can say that the RDE is a facilitator for the implementation of PAT in a pharmaceutical manufacturing environment. The idea that this differential value provides is based on establishing, for each process, the sub-steps IN, WHILE and OUTPUT.

Figure 16:
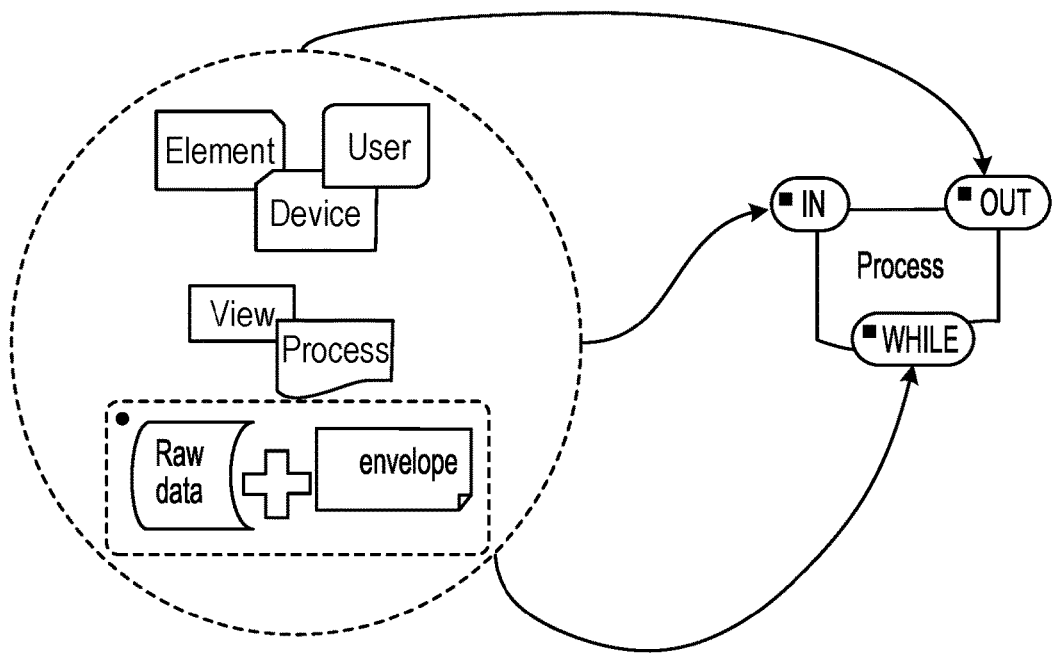
FIG. 16 is a block diagram illustrating an example of linking different objects in a process.

On each sub-step (IN, WHILE or OUTPUT) the elements, devices, users, and other process values or views, that are required to achieve a model that represents the reality of each activity, can be assigned. Thus creating links between the objects and the logical sequences of processes that will be later related in searches. The FIG. 16 shows the different relational possibilities of objects and processes.

The PAT implementation is driven by the fact that the associated objects to the process sub-step WHILE, and the values captured in the RDE through these objects, can be monitored in real time while they are stored in a data repository which is compliant with the regulatory requirements mandated in pharmaceutical environments. By extension, this information may notify the designed model to the DoS (Design of Space), providing real-time feedback to its own design's evaluation.

During the R+D+i phase of new drugs, the DoE (Design of Experiments) provides a systematic procedure that ensures the rigor and the quality of the work. The statistical theory underlying DOE generally starts with the concept of process models. Under this point of view, the process conception supplied by the RDE is a powerful tool to manage the raw data obtained through the planned experiments. These data can be analyzed to yield valid and objective conclusions using the RDE as the standard repository to store the primary information as results as well.

The process object's representation can be transcribed as follows:

---
Definition 9: Process structure
as object in RDE
---

```
Process:
{
    beID, Name, Description, ISA 95/88 tag, customized tag,
geolocation, status, required, crc
    Security:
    {
        ID Profile, ID user approval, expiration, effective
date
    }
    Input:
    {
        Elements:   [Element]
        Devices:    [Device]
        Users:      [User]
    }
    While:
    {
        Elements:   [Element]
        Devices:    [Device]
        Users:      [User]
    }
    Output:
    {
        Elements:   [Element]
        Devices:    [Device]
        Users:      [User]
    }
}
```
---

A view, that organizes the set of processes in a sequential way, has the following representation:

---
Definition 10: View structure as object in RDE
---

```
ViewProcess:
{
    beID, Name, Description, ISA 95/88 tag, customized tag,
geolocation, status, crc
    Security:
    {
        ID Profile, ID user approval, expiration, effective
date
    }
    Processes:
    {
        [Process:[Processes]]
    }
}
```
---

It's worth mentioning that the structure is recursive to allow multiple root processes with any kind of parent-child relationship.

4.5.1. Definition of the Algorithm

The processes' views are a fundamental tool for sequentially articulating the interaction between elements, devices and users. The overview of the interaction of the components involved can be summarized as follows:

A view contains a temporal and logical sequence of processes.

Objects could be associated to any of the three phases on the process execution: INPUT, WHILE and OUTPUT.

Objects can be repeated either in a process or in several processes of the view. In fact, it is common that the output elements of a process are the input elements of the following process.

The objects' association in the different steps of a view can be performed in the specified three different ways. For all the cases described henceforth, the action to determine whether a specific association must be applied, is indicated through the use of the coefficients $\alpha$, $\beta$, $\gamma$. This terminology indicates whether the association that precedes must be considered. For this reason their values are 1 (if the association applies) or 0 (otherwise). The applicability of the association depends on the criteria used by the actor who executes the algorithm in order to find relationships among the elements that may be related in some way with the required criteria.

The three-way association that are considered by the algorithm are described below.

4.5.2. Associations Through the INPUT, WHILE and OUTPUT Phases of a Process

This is the intrinsic association of the process's data sources. It is based on the elements' search that share the association's criteria defined by the user in the process's private environment. Therefore the scope of the associated objects are limited to the elements and devices linked to the INPUT, WHILE and OUTPUT of a given process's phase. Such as it is considered that an array of elements could be anchored to a phase (see Definition 1), a vector is used to identify each array of entities. The formalization of the different involved actors is as follows:

Objects sharing the same step INPUT in the same process: $In_i$

Objects sharing the same step WHILE in the same process: $Wh_j$

Objects sharing the same step OUTPUT in the same process: $Out_k$

The formalization of the association's criteria is expressed as follows:

$$IP(\text{Object}) = \alpha \cdot \Sigma In_i + \beta \cdot \Sigma Wh_j + \gamma \cdot \Sigma Out_k$$

IP (Object) is the association function containing all the elements and devices related to the same process depending on their relationship to the different phases of the process.

4.5.3. Objects' Association in a Same View's Processes

Figure 17:
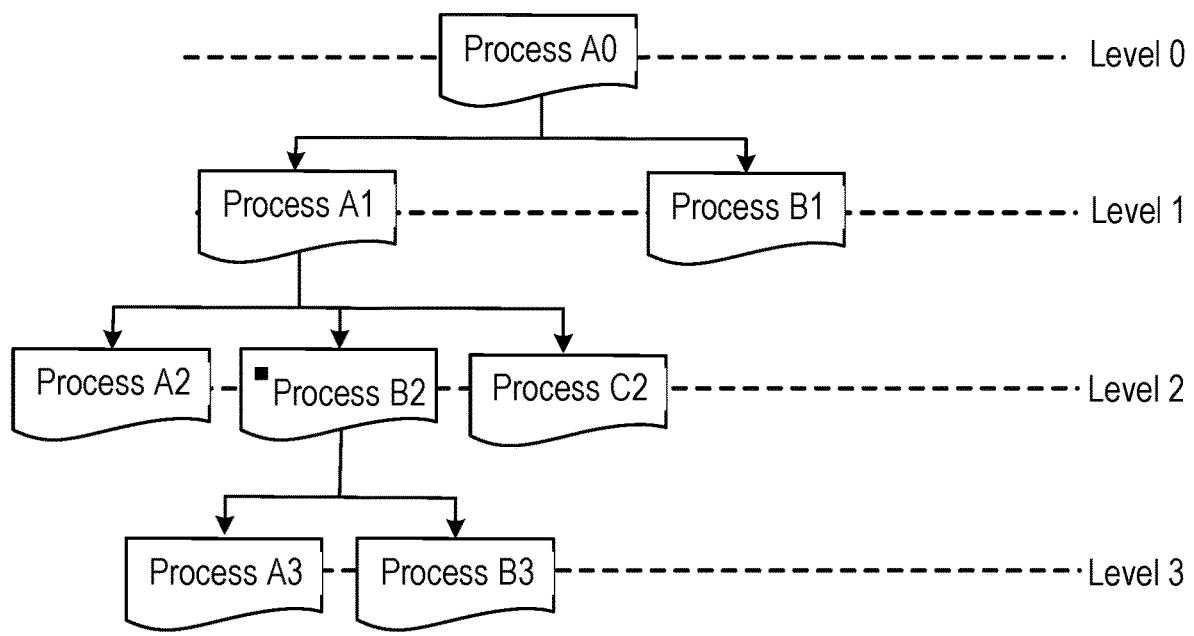
FIG. 17 is a block diagram illustrating an example of a hierarchical representation for a process association.

It is based on the search of the elements that share the association's criteria defined by the user in the environment of a view. Therefore the scope of the search objects extends to all the processes of a view. The relationships of the processes in a view are structurally hierarchical. In a hierarchical relationship there are different levels of clustering for a given object: parents, siblings and children. This definition in the clustering, is also repeated throughout the various levels contained in the hierarchy. FIG. 17 represents this situation.

Given an N level in which is the process that contains the data source or entity on which we want to get information for known objects' association, the set of all ancestors, descendants and objects that share the same level (ancestors, descendants and siblings respectively) are identified as:

Ancestor processes for all the upper levels: $P^L$

Descendants processes for all the lower levels: $Ch^L$

Siblings processes, obviously at the same level: S

The identification of an ancestor or descendant for a given level i or j respectively is a component of the vectors $P^L$ or $Ch^L$. Every component is formalized with the following expressions:

Ancestors processes on the specific upper level i: $P^{Li}_i$

Descendants processes on the specific down level j: $Ch^{Lj}_j$

It is important to emphasize that the level's position is always relative to the process on which the request of information is based.

From the identification of the processes involved in the search definition hierarchically related each other, the formalization of the association criteria can be expressed as follows:

$$IV(Object) = \alpha \cdot \Sigma P^{Li}_i + \beta \cdot \Sigma Ch^{Lj}_j + \gamma \cdot \Sigma S_k$$

IV(Object) is the association function containing all related processes through hierarchical associations with the process that contains the specified object.

4.5.4. Association of Objects in Different Views

When cross information requests along different views where an object can be present (embedded within the processes) are needed, this association is required. In this case, the user's association's criterion is limited to the views to be included in the filter. The formalization of the views is as follows:

Views with processes where requested object should be checked: $W_i$

So that the formalization of the association's criteria is expressed as follows:

$$PV(Object) = \alpha \cdot \Sigma W_i$$

PV(Object) is the association function that contains all the processes views, related to each other, in order to include involved the requested object about it is needed to get information.

4.5.5. Algorithm to Find Overall Associations for a Known Object

Based on the three previous expressions, for a known data source, the algorithm that allows to find all the associations for the specified object is expressed as follows:

$$S_n(Object) = IP(Object) + IV(Object) + PV(Object)$$

Where $S_n$ is the set of entities (data sources, processes, views) that are related with a given object by means the view process association. Thus the algorithm is able to get information about all the elements that are related with a given one, and that are sharing a space of entities based on processes and views.

Considering that an object is a potential data source of electronic records and the system is able to identify the source of each electronic record, the vector $V_k$ represents the set of values that has been produced by an object. Regarding the data sources and their generated values, the dependency of both concepts can be formalized in this way:

$$V_k = f(S)$$

Where S is an entity that issues data and that matches with each entity found by the concept $S_n$(Object). This sentence reflects that values generated by any source have a direct and functional dependency with their origin. For any system closed under the defined constrictions as defined for the RDE, it must exist the inverse of the function f(S) that leads to the following equality:

$$S = f^{-1}(V_k) = g(V_k)$$

Or equivalently, for any individual value, it is possible to find its source. Then, it is feasible to infer that for any view process association, there is a list of sources related between them by means the contour of conditions in this way:

$$S_n(Object) = g_n(Object, V_k) = IP(Object) + IV(Object) + PV(Object)$$

Thus, it is defined the association of entities $(S_n)$ and their values $(V_k)$ that constitute the source of values in a given system that are related between them by means the view process association.

4.5.6. Dimensionless Process Characterization

The process definition as has been described in this specification is characterized for a distribution of entities across the three different phases INPUT, WHILE and OUTPUT. The model associated to the structure entity-phase provides two different metrics: static and dynamic. For each type of metric, a dimensionless vector can be used to generate an objective representation of the process that allows other processes to be described using the same terminology.

4.5.6.1. Static Metrics

This metric provides information about the ecosystem of entities distributed along the different phases in a process. This measure allows for the creation of a vector where the vector components enumerate the similarity between the different types of entities, number of entities in phases and also among the number of parents for the set of entities. The dimensionless vector associated to the static metric is based on the following counts:

Number of total, input, while and output entities. Represented by $E1_i$, where the index i can be total, input, while or output.

Number of distinct and repeated entities across the process. Represented by $E2_j$, where the index j takes the value distinct or repeated.

Number of entities belonging to each entity type (device, element, user) in total and for each phase. Represented by $E3_{mp}$, where the index m takes the value device, element or user. The index p can take input, while or output values.

Number of views where the process is involved. Represented by V.

Number of associations where the process is involved. Represented by A.

Number of ascendants, siblings and descendants of the entities located in the process. Represented by $F_r$, where the index r can take ascendants, siblings or descendants value.

In order to achieve a dimensionless metric, the percentage of each concept is performed. Therefore the following percentage measures are obtained:

Percentage of input, while and output entities for each phase and across the entire process (represented by $PE1_i$).

Percentage of distinct and repeated entities across the process (represented by $PE2_j$).

Percentage of entities belonging to each entity type (device, element, user) in total and for each phase (represented by $PE3_{mp}$).

These measures can be classified in absolute and relative metrics and both lead to two concepts that explain the behavior of the entities associated in a process: measures that provides information about the entity distribution and about the process definition. To obtain a normalized expression independent of the unit of measure of the concept that represents, the normalization calculation is applied:

$$N_X = \frac{\Sigma X_i}{\sqrt{\Sigma X_i^2}}$$

Where $X_i$ is each variable that applies to the entity distribution and process definition concept. Variables that provides information about the entity distribution are $E1_i$, $E2_j$, $E3_{mp}$, $F_r$, $PE1_i$, $PE2_j$ and $PE3_{mp}$. In the other side, variables that provides information about the process definition are $E1_i$, $E3_{mp}$, V, A, $PE1_i$ and $PE3_{mp}$ (notice that $E1_i$, $E3_{mp}$, $PE1_i$ and $PE3_{mp}$ belong to the intersection). Considering this differentiation, a normalized vector with two components can be defined as:

$$Cs=(N_E,N_P)$$

Where $N_E$ is the normalization of the set of measures involved in the entity distribution and $N_P$ is the equivalent to the measures related with the process definition. Cs is the dimensionless vector that characterize a process from a static point of view. Each component of the vector has two measures: absolute and relative, and each component is calculated as follows:

$$N_{E-absolute} = \frac{\Sigma E1_i + \Sigma E2_j + \Sigma E3_{mp} + \Sigma F_y}{\sqrt{\Sigma E1_i^2 + \Sigma E2_j^2 + \Sigma E3_{mp}^2 + \Sigma F_y^2}}$$

$$N_{E-relative} = \frac{\Sigma PE1_i + \Sigma EP2_j + \Sigma PE3_{mp}}{\sqrt{\Sigma PE1_i^2 + \Sigma PE2_j^2 + \Sigma PE3_{mp}^2}}$$

$$N_E = \frac{N_{E-absolute} + N_{E-relative}}{\sqrt{N_{E-absolute}^2 + N_{E-relative}^2}}$$

$$N_{P-absolute} = \frac{\Sigma E1_i + \Sigma E3_{mp} + A + V}{\sqrt{\Sigma E1_i^2 + \Sigma E3_{mp}^2 + A^2 + V^2}}$$

$$N_{P-relative} = \frac{\Sigma PE1_i + \Sigma PE3_{mp}}{\sqrt{\Sigma PE1_i^2 + \Sigma PE3_{mp}^2}}$$

$$N_P = \frac{N_{P-absolute} + N_{P-relative}}{\sqrt{N_{P-absolute}^2 + N_{P-relative}^2}}$$

The normalized dimensionless component for entity metric. The dimensionless calculation is managed through the percentage of each of the previous concepts.

4.5.6.2. Dynamic Metrics

Each entity linked to the phases of the process is a potential producer of data. The information generated for the set of entities are time dependent and for this reason, they are affected by variability. Independently of this variation, a metric based on the set of values generated by the process (associated entities) can expose a measure about its activity. The activity is measured in the number of generated records and the spent time during this data production. In a similar way as the vector Cs represents a dimensionless vector for the static characteristics of a process, the vector named Cd provides the indicator that characterize the variability associated to a process that is induced by the execution of this process along the time. The measures are coming through the values produced by the entities linked to the process, as by the required time spent by each entity as well. The dynamic information is coming through the following dynamic concepts.

Number of produced records by phase in a given time range. Represented by $R1_i$, where the index i can be total, input, while or output.

Number of produced records by entity and total amount of records produced in a given time range for all the entities and type of entity across all phases. Represented by $R^2_{mp}$, where the index m takes the value device, element or user. The index p can take input, while or output values.

Duration of the spent time of each entity type across all phases. Represented by $D1_{nq}$, where the index n takes the value device, element or user. The index q can take input, while or output values.

Duration of each phase and total spent time execution for the entire process. Represented by $D2_i$, where the index i can be total, input, while or output.

In order to achieve a dimensionless metric, the percentage of each concept is performed. Therefore the following percentage measures are obtained:

Percentage of produced records by phase in a given time range (represented by $PR1_i$).

Percentage of produced records by entity in a given time range for all the entities and type of entity across all phases (represented by $PR2_{mp}$).

Percentage of the duration of the spent time of each entity type across all phases (represented by $PD1_{nq}$).

Percentage of the duration of each phase for the entire process (represented by $PD2_i$).

Following the same reasoning than described for the dimensionless vector Cs (to characterize a process from a static point of view), the Cd (vector to characterize process from a dynamic perspective) is composed of absolute and relative variables. Inside both types of variables, two different sets of information arise related with the dynamic behavior of the process: measures that provides information about the number of records produced by of the entities during the process and information related with the duration of the process and its phases. Variables that provides information about the amount of records issued by the entities are $R1_i$, $R^2_{mp}$, $PR1_i$ and $PR2_{mp}$. In the other side, variables that provides information about the time spent during the process execution are $D1_{nq}$, $D2_i$, $PD1_{ng}$ and $PD2_i$. Considering this differentiation, a normalized vector with two components can be defined as:

$$Cd=(M_R,M_D)$$

Where $M_R$ is the normalization of the set of measures related with the records produced by the entities in the process. $M_D$ is the normalization of the concepts related with the time spent during the process execution. Cd is the dimensionless vector that characterize a process from a dynamic point of view. Each component of the vector is calculated as follows:

$$M_{R-absolute} = \frac{\Sigma R1_i + \Sigma R2_{mp}}{\sqrt{\Sigma R1_i^2 + \Sigma R2_{mp}^2}}$$

$$M_{R-relative} = \frac{\Sigma PR1_i + \Sigma PR2_{mp}}{\sqrt{\Sigma PR1_i^2 + \Sigma PR2_{mp}^2}}$$

$$M_R = \frac{M_{R-absolute} + M_{R-relative}}{\sqrt{M_{R-absolute}^2 + M_{R-relative}^2}}$$

$$M_{D-absolute} = \frac{\Sigma D1_{nq} + \Sigma D2_i}{\sqrt{\Sigma D1_{nq}^2 + \Sigma D2_i^2}}$$

$$M_{D-relative} = \frac{\Sigma PD1_{nq} + \Sigma PD2_i}{\sqrt{\Sigma PD1_{nq}^2 + \Sigma PD2_i^2}}$$

$$M_D = \frac{M_{D-absolute} + M_{D-relative}}{\sqrt{M_{D-absolute}^2 + M_{D-relative}^2}}$$

The dimensionless vectors Cs and Cd provide static and dynamic representation of a process as defined in this document. Both vectors can be used to compare different processes between themselves under a normalized perspective. When the same process is compared at different points in time, the Cs is always the same, but the Cd can change depending on the duration and the amount of the produced records.

Both numbers can be used to identify processes that are similar under the entities, distribution across the process phases, generated values and the spent time, because the normalization establishes an objective way to make comparisons.

4.6. Object Association

The content of this section is described with respect to FIG. 6.

There is an additional way to create links besides the natural association and view definition. Objects that could be potential transmitter or that they are real data sources could be related between themselves, establishing a customized association.

The object association is managed by the table BF_AS-SOCIATION.

006A. An object association is a predefined relationship between data sources (users, elements and devices) with different purposes.

Figure 18:
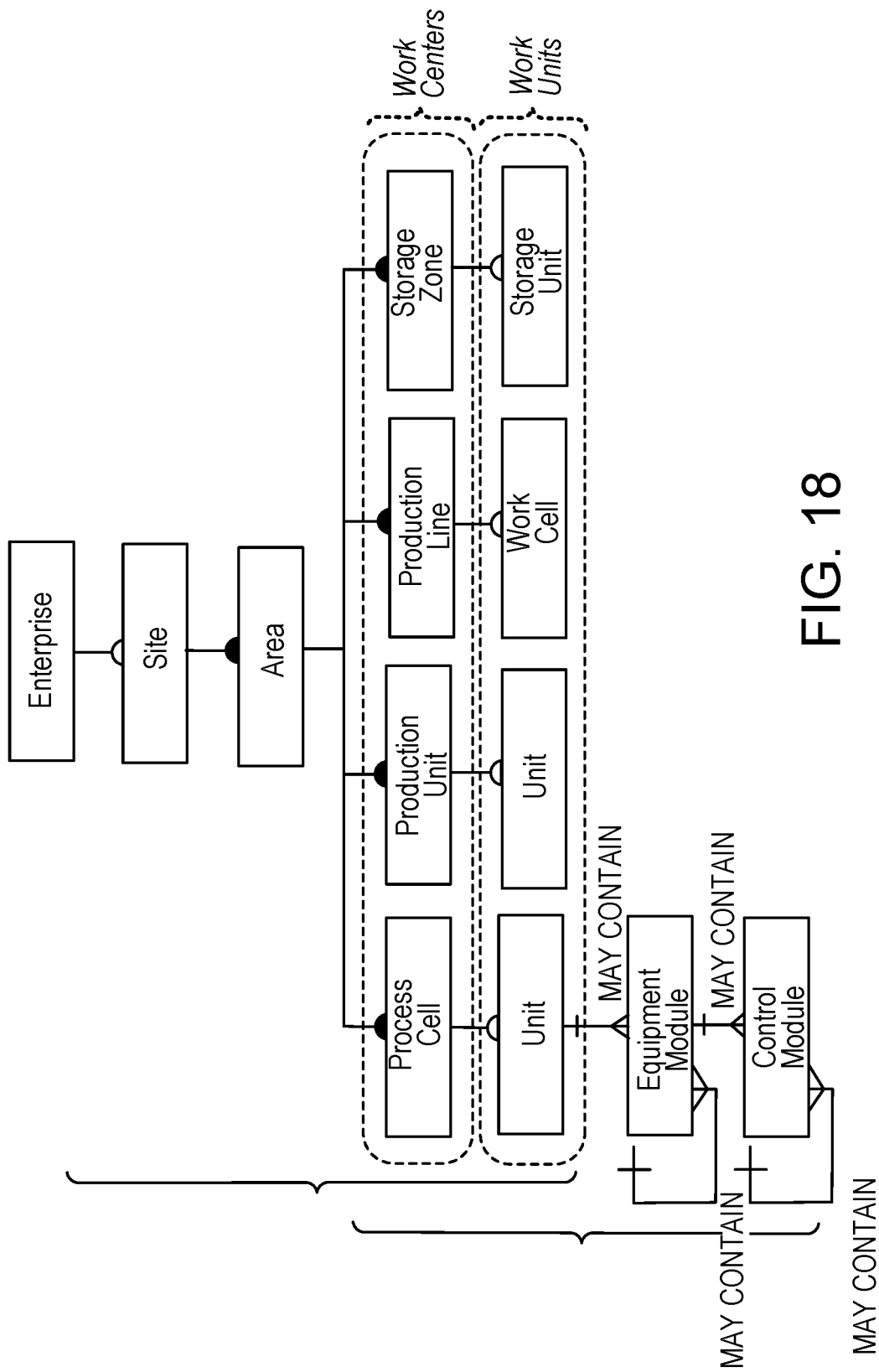
FIG. 18 is a block diagram illustrating an example of an equipment hierarchy model.

Examples about purposes that could be applied for object associations could be:

Hierarchy of objects. When it is necessary to establish a hierarchy between objects (e.g., ISA 95/88 structure) it is a good practice to create relational structures between objects. Abstract conceptualizations could be another way to implement hierarchies between objects (e.g., Equipment/Scales/Pallet Scale/Specific balance). The FIG. 18 shows an example about this kind of relationship.

Figure 19:
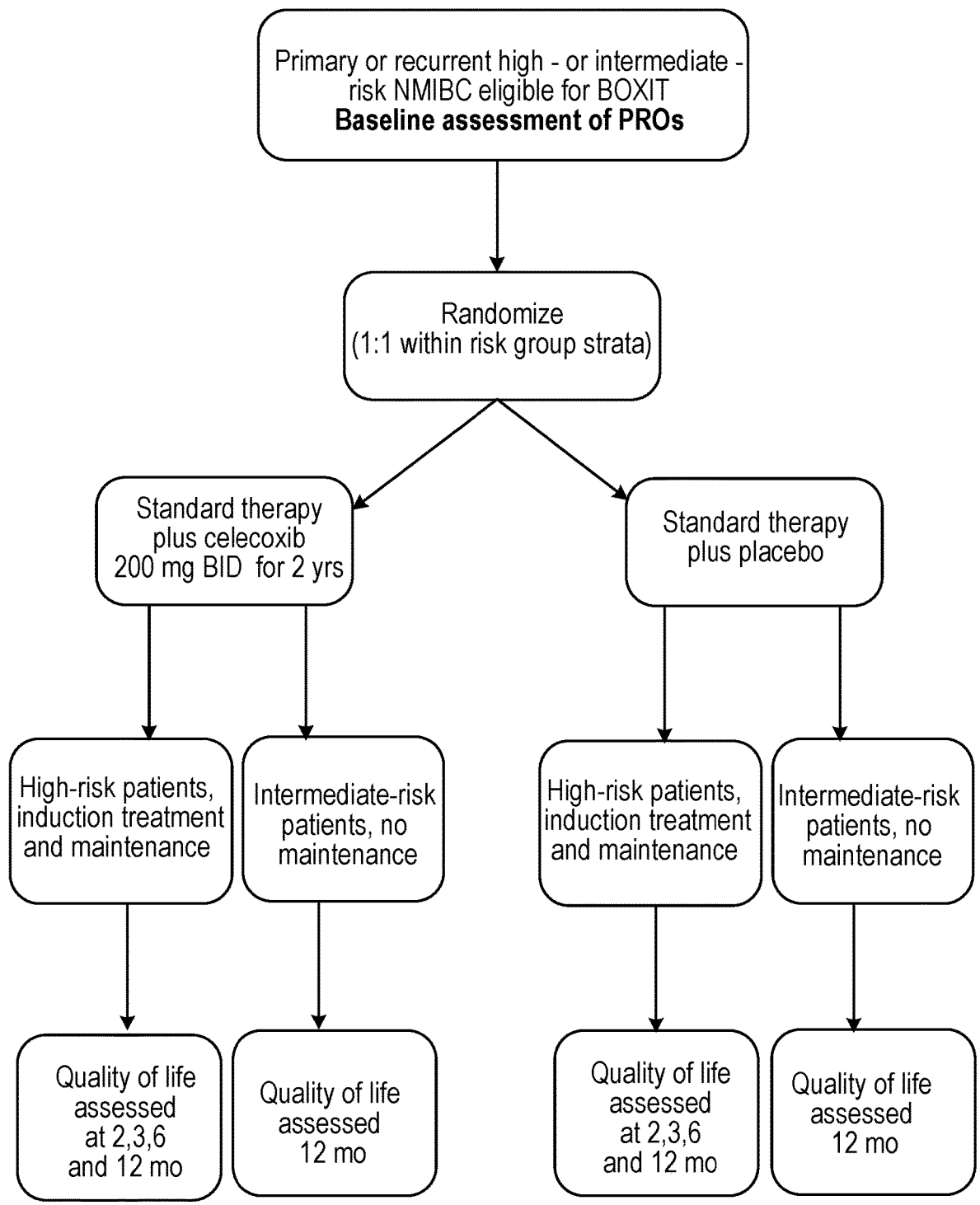
FIG. 19 is a block diagram illustrating an example of relationships between elements involved in a clinical trial.

Containing relations. Considering elements as physical objects in the manufacturing site that could include other elements, devices or users. In this case relations of containment should be established between objects to keep the real structure on the site. The FIG. 19 shows an example about this kind of relationship.

Functional relations. Objects could be linked under a functional point of view when there are dependencies of cause-effect type. A study of clinical trials is an example of how elements (therapy, risks, success results) can be associated with users (doctors and patients) and devices (software and electronic devices) to share information in the system. The results of the primary information analyzed from the repository also could be uploaded to the RDE; thereby different solutions could be achieved as post-product-acceptance data for further research, variants of medicines, counter indications or use for specific patient groups. The FIG. 19 shows an example about this kind of relationship.

Origin and target associations. This kind of relations are thought for objects that are produced by other objects in the broadest sense. Examples about this links could be working order that generate a final batch, pallets break down that produce different boxes (e.g., distribution process), drug transport, etc.

Associations can be managed in the RDE through the following structure:

| Definition 11: Assocation definition |
|---|
| Association:<br>{<br>  beID, Name, Description, ISA 95/88 tag, customized tag, geolocation, status, crc<br>  Security:<br>  {<br>    ID Profile, ID user approval, expiration, effective date<br>  }<br>  Objects:<br>  {<br>    [beID Object:[beID Object]]<br>  }<br>} |

An object association requires a lifecycle (edition—verified—certified—archive) to ensure that his association can be used for regulatory purposes.

4.7. Issuing Information with Required User Authentication

The content of this section is described with respect to FIG. 7.

It is necessary to ensure the source of the data as the data itself once it reaches the system. The life of data is not only related with the insertion process, but also with its possible modification and archive process. This figure shows graphically how data must be ensured when user authentication is required (e.g., critical processes, life cycle of objects, user confirmations, etc.).

This section is directly driven by the detailed information written in the Regulatory Layer section.

007A. The usual way to send information is using an object (element or device) that has been properly identified in the RDE. In this case, the object from which the data has been submitted can on cannot accept a PGP key that has been previously registered in the system. If the process requires the user authentication (this is the topic of this section), the user's PGP key will be used. When the user has been properly identified, its information is associated to the raw data, but the object that generated the raw data (element or device) is sent in the raw data envelope. Further detail can be found in the API access from devices and elements and Signatures at API level sections in the Regulatory Layer section.

007B. When the object is not recognized in the RDE (e.g., when the calls to the API are performed from a web app on a non-identified computer), a first authentication is required (e.g., the user's one that interacts with the web application). It may happen that a new user, different than the logged one, could confirm the associated data with its profile. In this case, a second authentication, for this second user, should be performed. Under this scenario, the first user, authenticated as the one to be associated with the data sent by the computer, will be included in the envelope. The reason for that is the meaning of the data source associated to the first that logged in the computer. The second authenticated user is included in the raw data. More detail can be found in sections Authorization at API level, Signatures at API level and User expiration at API level in the Regulatory Layer section.

4.8. Data Association Through Customized Relationships

The content of this section is described with respect to FIG. 8.

This section is directly related to the section "Automatic data relation" above. On top of the data that asynchronously reaches the system users can create relationships between the objects generated by these data. These customized associations are completely independent from the records that these objects originate, providing the system, this way, with different connection networks between the existing data sources.

The various connectivity networks offered by RDE to associate elements with each other are: object association (e.g., Object association section above), process links (e.g., View Process Management section above) and data structure (e.g., DatamAcquisition 003C above). Besides these customized connections, also the automatic relations are always executed (relations described in Automatic data-relation.) A detailed formal description of the associations that can be made through the different relational networks between RDE objects will follow. For all the described cases, the associated terminology to the coefficients $\alpha$, $\beta$, $\gamma$, $\varphi$, $\eta$ (regarding 008G in FIG. 8) indicates whether the association that precedes is or is not considered. For this reason their values are 1 (if the association applies) or 0 (otherwise). The applicability of the association depends on the criteria used by the user performing the search for elements that may be related in some way with the required criteria.

Figure 20:
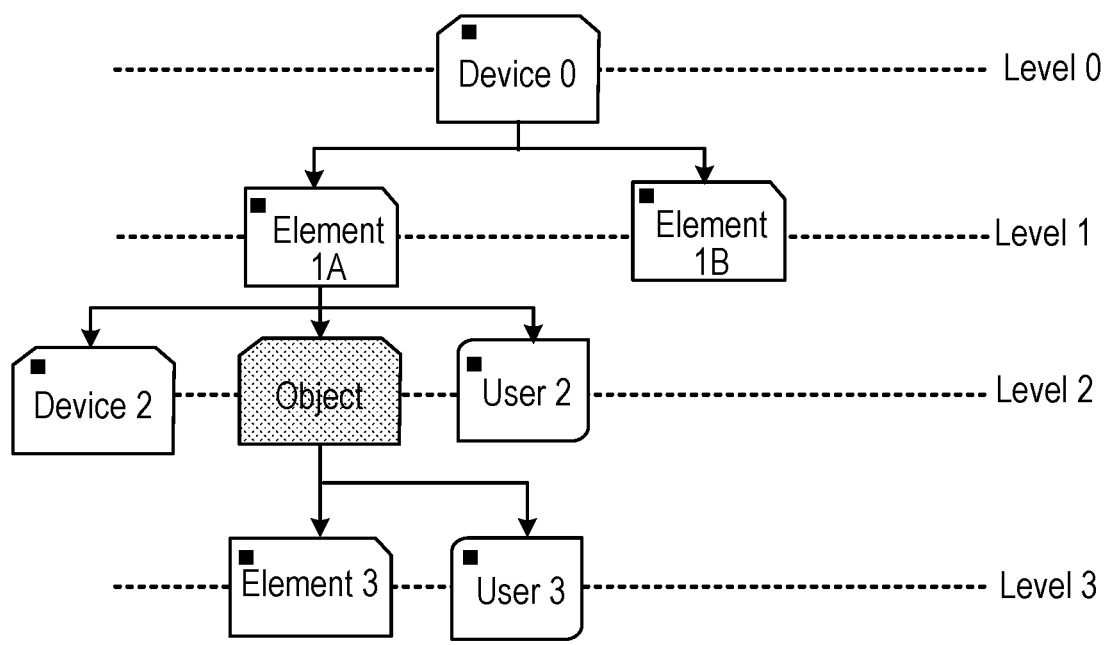
FIG. 20 is a block diagram illustrating an example of a hierarchical representation for object association.

008A. The relationships that users set through the objects associations creation (e.g, as described in the Object association section above) are structurally hierarchical (though that may be designed by functional objectives, of content, . . . ). In a hierarchical relationship there are different levels of clustering for a given object: parents, siblings and children. This definition in the clustering, is also repeated throughout the various levels contained in the hierarchy as shown in FIG. 20.

Given a level N in which the data source is (element or device) on which we want to search for information for a given object association, the set of all ancestors, descendants and other objects that share the same level (ancestors, descendants and siblings respectively) are identified as:
  Ancestors for all the upper levels: $P^L$
  Descendants for all the lower levels: $Ch^L$
  Siblings, obviously at the same level: S
  The identification of an ancestor or descendant for a given level i or j respectively is a component of the vectors $P^L$ o $Ch^L$. Each component is formalized with the following expressions:
  Ancestors on the specific upper level i: $P^L{}_i$
  Descendants on the specific down level j: $Ch^{Lj}{}_j$
  Note that the level position is always relative to the object on which the search is based.

After identifying the involved elements in the search definition hierarchically related to each other, the formalization of the association criteria is expressed as follows:

$$H(\text{Object}) = \alpha \cdot \Sigma P^{Li}{}_i + \beta \cdot \Sigma Ch^{Lj}{}_j + \gamma \cdot \Sigma S_k$$

H (Object) is the search function that contains all the elements and related devices through hierarchical associations with the concerned object.

008B. The processes' views are a fundamental tool for sequentially articulating the interaction between elements, devices and users. The overview of the interaction of the components involved can be summarized as follows:
  A view contains a temporal and logical sequence of processes.
  Objects could be associated to any of the three phases on the process execution: INPUT, WHILE and OUTPUT.
  Objects can repeat either in a process or in several processes of the view. In fact, it is common that the output elements of a process are the input elements of the following process.
The objects' association in the different phases of a view can be done as follows:

008C. Intrinsic association of the process's objects. It is based on the elements' search that share the association's criteria defined by the user in the process's private environment. Therefore the scope of the search objects are limited to the elements and devices linked to the INPUT, WHILE and OUTPUT of a process's phases. The formalization of the different involved actors is as follows:
  Objects sharing the same step INPUT in the same process: $In_i$
  Objects sharing the same step WHILE in the same process: $Wh_{kj}$
  Objects sharing the same step OUTPUT in the same process: Out
  The formalization of the association's criteria is expressed as follows:

$$IP(\text{Object}) = \alpha \cdot \Sigma In_i + \beta \cdot \Sigma Out_j + \gamma \cdot \Sigma Wh_k$$

IP (Object) is the search function containing all the elements and devices related to the same process depending on their relationship to the different stages of the process.

008D. Objects' association in a same view's processes. It is based on the search of the elements that share the association's criteria defined by the user in the environment of a view. Therefore the scope of the search objects extends to all the processes of a view. Given that a view determines the processes' sequencing by establishing a hierarchy among them, the associations are done in a similar way to that described for the management of objects' associations. Applying the same analogy, given an N level in which is the process that contains the item or device on which we want to search for information for known objects' association, the set of all ancestors, descendants and objects that share the same level (ancestors, descendants and siblings respectively) are identified as:
  Ancestor processes for all the upper levels: $P^L$
  Descendants processes for all the lower levels: $Ch^L$
  Siblings processes, obviously at the same level: S
  The identification of an ancestor or descendant for a given level i or j respectively is a component of the vectors $P^L$ or $Ch^L$. Every component is formalized with the following expressions:
  Ancestors processes on the specific upper level i: $P^{Li}{}_i$
  Descendants processes on the specific down level j: $Ch^{Li}{}_j$
  It is important to emphasize that the level's position is always relative to the process on which the search is based.

From the identification of the processes involved in the search definition hierarchically related each other, the association criteria's formalization is expressed as follows:

$$IV(\text{Object}) = \alpha \cdot EP^{Li}{}_i + \beta \cdot \Sigma Ch^{Lj}{}_j + \gamma \cdot \Sigma S_k$$

IV(Object) is the search function containing all related processes through hierarchical associations with the process that contains the specified object.

008E. Association of objects in different views. When cross searches along different views where an object can be present (embedded within the processes) are needed, this association is required. In this case, the user's association's criterion is limited to the views to be included in the filter. The formalization of the views is as follows:
  Views with processes where a searched object should be checked: $W_i$ So that the formalization of the association's criteria is expressed as follows:

$$PV(Object) = \alpha \cdot \Sigma W_i$$

PV(Object) is the search function that contains all the processes views, related to each other, in order to include involve the search object.

008F. Association through objects' attributes. All elements, devices, users, processes and views have attributes that allow characterizing them properly. These features may vary from one object to another (e.g., a device can have the manufacturer attribute that the user does not have). Additionally the user can add his own tags (customized tags) and standard tags (S85/S88 tags). All these properties can be part of the search criteria. The formalization of the various attributes involved in the search is:

Attributes belonging to the searched object: $a_i$

So that the association criterion's formalization is expressed as follows:

$$A(Object) = \alpha \cdot \Sigma a_i$$

A(Object) is the search function that contains all the objects related to each other, since they contain identical attributes to the ones listed in the search object.

008G. When doing searches by establishing association criteria between the different system's objects as well as of their attributes, a linear combination of the different associations made on each link (procedures, views, hierarchies and attributes) is established. A new function of objects' relation is thus obtained, represented by the following expression:

$$R(Object) = \alpha \cdot A(Object) + \beta \cdot H(Object) + \gamma \cdot IP(Object) + \varphi \cdot IV(Object) + \eta \cdot PV(Object)$$

R(Object) is the items' set (users, elements, devices, processes and views) that match any of the search terms specified by the user (only those criteria where the coefficients of the dependent functions are involved—$\alpha$, $\beta$, $\gamma$, $\varphi$, $\eta$—are nonzero).

008H. As a result of the described operation in element 008G the collection of items related to each other according to the search criteria established by the user is obtained. The final step is to get the values (value-type) associated with these related items for a certain range of dates. Determining the date range is required, as it is the way the system has to limit the search in acceptable timings.

To get the values linked to the objects' set resulting of the R(Object) function, the following operations are executed (always by the timestamp range previously defined and represented by $\Delta t$):

Get all value-types that contains in the attribute Who of their envelopes ($e^{Who}$), the object $R_i$ belonging to the collection R(Object): $\Phi(\Sigma_{\Delta t}(e^{Who}_i = R_i))$ Get all value-types that contains in the attribute Where of their envelopes ($e^{Where}$), the object $R_i$ belonging to the collection R(Object): $\Phi(\Sigma_{\Delta t}(e^{Where}_i = R_i))$ If standard (ISA 95/88) tags or custom tags have been defined (then $\alpha \neq 0$ in the R(Object) definition), get all value-types that contains these tags in the attribute What of their envelopes ($e^{What}$): $\Phi(\Sigma_{\Delta t} e^{What})$ Finally, the set of value-types that match with the search criteria is a linear combination of all the value-types gotten for each individual collection:

$$V_K = (\Sigma_{\Delta t}(e^{Who}_i = R_i)) + \Phi(\Sigma_{\Delta t}(e^{Where}_i = R_i)) + \Phi(\Sigma_{\Delta t} e^{What})$$

Where $V_K$ is the vector containing all value-types resulting from the search.

4.9. Scenarios

Figure 9:
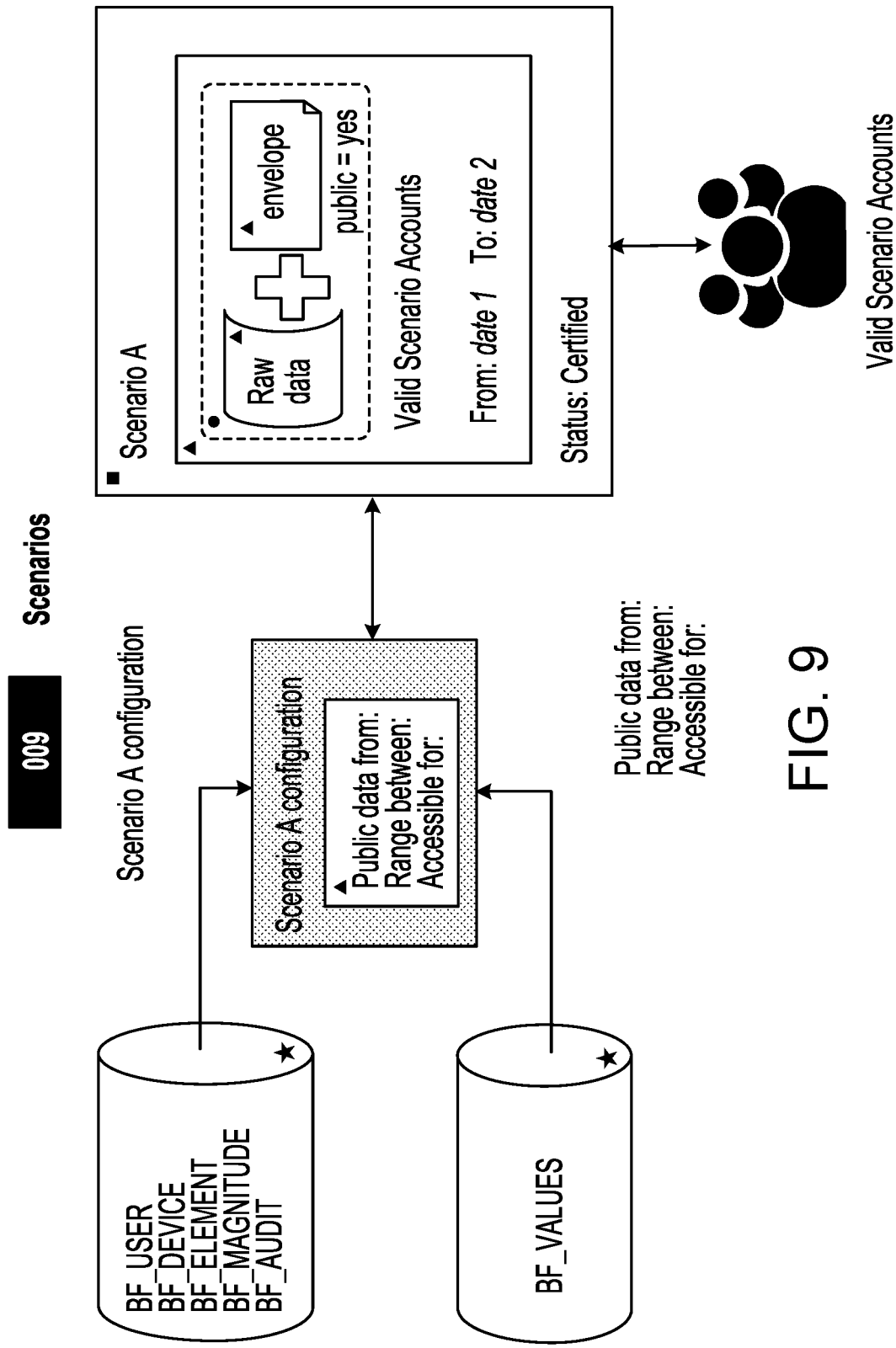
FIG. 9 is a block diagram illustrating an example of scenarios.

The content of this section is described with respect to FIG. 9.

All objects that have a direct connection with a data source (user, device or element) have the property public in its definition. A scenario can integrate information from a selection of objects that have been classified as public=yes. Thus, the users of the system (supposing they have the appropriate permission) can create groups of sources of information that can be accessed by other users in order to query results from this scenarios. These actors that work only with the data configured for specific scenarios are named users of scenarios.

These users require a scenarios account within the owner environment, but can only access those scenarios that have been associated. This framework of data in turn, only make visible those sources of information previously defined and characterized as public=yes.

This dynamic system to display information allows to establish collaborative frameworks between different owner environments. The following examples show some use cases related to the use of scenarios:

Clinical studies of different entities that can be shared to expand the study sample.

Pharmaceutical products developed by third parties.

Companies that sell drugs of manufacturers.

Governments that require verification of known quality parameters.

Data control from the manufacturer for the final consumption to combat the counterfeiting.

Following the current regulation guidelines, where is it's mandatory to satisfy the end user needs, this counterfeiting feature provides a unique tool to assure the product reliability.

Full traceability for distributors.

Monitoring of prescriptions for different health professionals linked to common medical records.

Real-time monitoring of variables (e.g., OEE, Key Performance Indicator (KPI) definition).

The main features of using the RDE's scenarios are:

The accounts of scenarios associated to individual users can only access the information designed by the RDE's users and just through the frame that has been created.

Users associated to the RDE are also potential users to access to scenarios. Previously they must have been associated to the scenario.

Data shown in scenarios can never be modified. Scenarios are just used for read, never for write action.

The activity on scenarios (user logins, actions) is also traced in the system.

The range of dates of the data to be displayed is a required configuration parameter to define a scenario.

Scenarios can be managed in the RDE by the following object structure:

---

Definition 12: Scenario definition

Scenario:
{
  beID, Name, Description, customized tag[ ], status
  Security:
  {
    [beID User]
  }
  Users:
  {
    [beID User]
  }

-continued

Definition 12: Scenario definition

Elements:
{
    [beID Element]
}
Devices:
{
    [beID Device]
}
}

4.10. Agents

Figure 10:
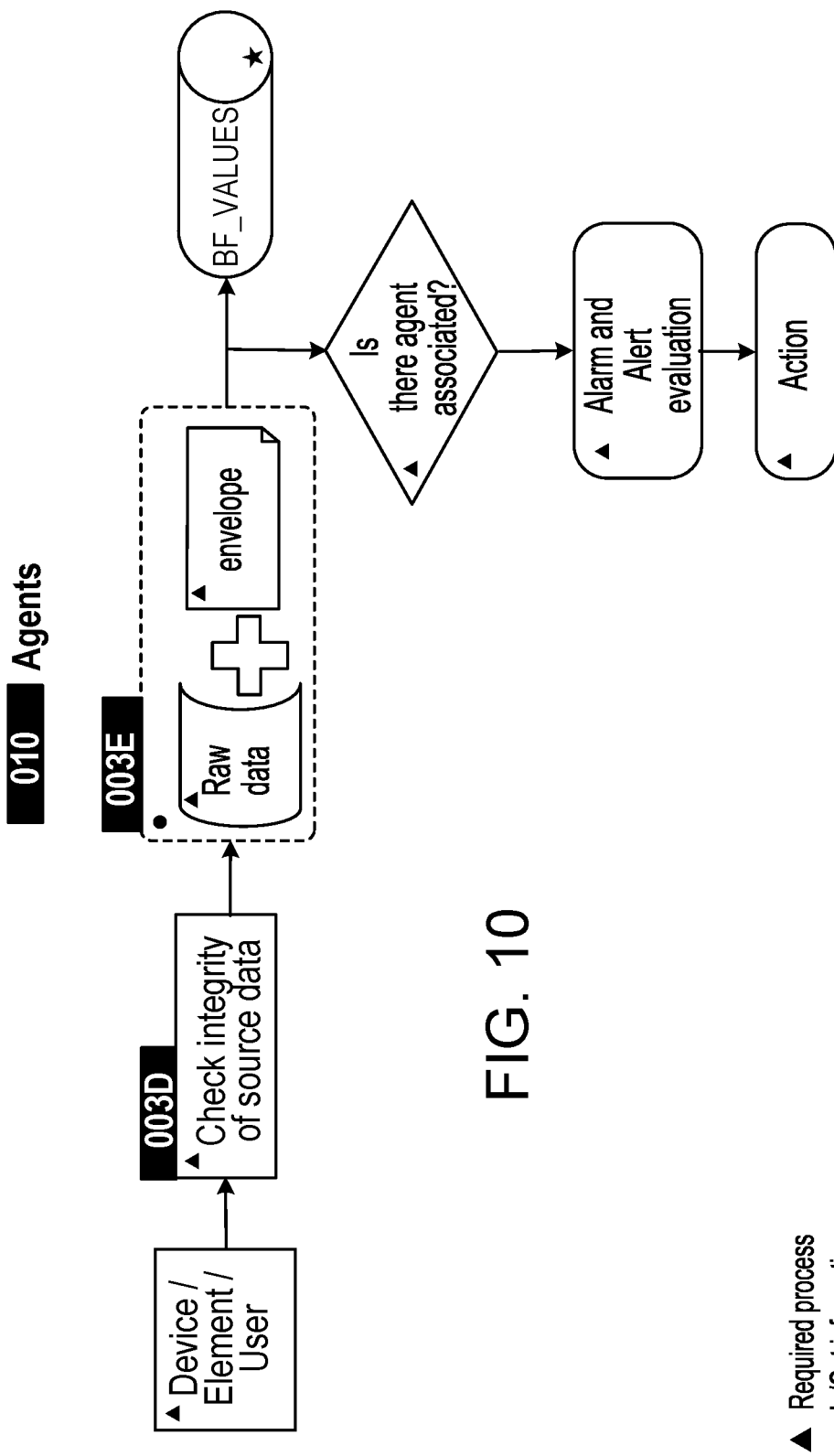
FIG. 10 is a block diagram illustrating an example of agents.

The content of this section is described with respect to FIG. 10.

The agent concept is based on a configurable listener that performs customized actions depending on the values obtained from different data sources. An agent can evaluate the values that reach RDE according to two types of associations:

- All values coming from a particular user, element or device can be verified in real time, applying to all of them the same alerts policies.
- Only values coming from a single value-type are checked (specific magnitude of an element or device or, in case of users, the associated type).

To set and/or deploy an agent two concepts must be determined:

- Alarm levels against which the obtained results will be assessed.
- Actions to perform when the values are out of range for each configured alarm.

Agents can be managed in the RDE by the following object structure:

Definition 13: Agent definition

Agent:
{
    beID, Name, Description, customized tag [ ], status, [OnObjects], [OnValueTypes]
    Alarms:
    {
        [Alarm:
        {
            beID, Name, Description, condition, limitExpression, ellapsedTimeForNextAction
            Action:
            {
                beID, Name, Description, condition, type, [configurationParameters]
            }
        }]
    }
}

4.10.1. Alarm Definition

For each agent different alarms can be created. In turn, for each alarm an action must be associated. This action will be executed when the incoming value from users, elements or devices, configured to be inspected in the alarm, are out of specs. To define an alarm three concepts must be declared: comparison term, condition and limit expression.

Comparison term: It's the term to be verified when a new value is incoming from an object that has an agent associated. This is the first concept in a comparison statement. The syntax of the sentences that could be written in this field is listed in the Table 4 (Symbol definitions for alarm comparison).

If nothing is indicated, it is assumed that the current value (the newest) must be evaluated. The omission of this concept is equivalent to indicate [VALUE].

Condition: It's the criteria to compare the incoming value with the limit expression. A comparison can only take one of the following symbols:

TABLE 2

Symbol definitions for alarm conditions

| Condition description | Related symbol |
|---|---|
| Equals | = |
| Different than | <> |
| Greater than | > |
| Greater or equals than | >= |
| Less than | < |
| Less or equals than | <= |
| Starts with | ¿ |
| Ends with | ? |
| Contains | % |
| Value has changed | * |
| Call REST | REST |

When simple condition evaluation (=, <, >, < >, etc.) are not enough to define a valid criteria to acquire a boolean result that decides the agent triggering, more complex decision evaluation can be made calling a REST service. In this case, any customized condition can be implemented outside the system. The expected result from the REST call to trigger the action is to receive the value "1". Any other result will be considered as non-triggering action.

Limit expression: It's the definition of the statement that will be evaluated when incoming data is associated to an agent. When the value is received in the RDE, it is compared with the limit obtained as result of the statement and the associated comparison expression. The limit expression accepts mathematical definitions as described in the following table:

TABLE 3

Mathematical terminology accepted in the limit expression

| Mathematical terminology for operations | Related expression |
|---|---|
| Addition | + |
| Subtraction | − |
| Multiplication | * |
| Division | / |
| Exponentiation | ^ |
| Modulus | % |
| Absolute value | abs |
| arc cosine | acos |
| arc sine | asin |
| arc tangent | atan |
| average of arguments | average |
| nearest upper integer | ceil |
| Cosine | cos |
| hyperbolic cosine | cosh |
| nearest lower integer | floor |
| natural logarithm (base e) | ln |
| base 10 logarithm | log |
| maximum of arguments | max |
| minimum of arguments | min |
| nearest integer | round |
| Sine | sin |
| hyperbolic sine | sinh |
| sum of arguments | sum |
| tangent | tan |
| hyperbolic tangent | tanh |

TABLE 3-continued

Mathematical terminology accepted in the limit expression

| Mathematical terminology for operations | Related expression |
|---|---|
| pseudo-random number (between 0 and 1) | random |
| Base of natural algorithms | e |
| Ratio of the circumference of a circle to its diameter | pi |

The alarms associated to the agents may take different values in time (e.g., the limits of acceptance of a weight may depend on the kind of product to weight). For this reason, the comparison values against which the agents do the comparison in real time on the received values, can be referenced against dynamic values of predefined value-types. In some implementations, the Limit expressions cannot be based in static statements (e.g., numeric values or string constants).

The system can infer in the statements definition references to dynamic values from value-types. The nomenclatures to be used to reference a dynamic value is:

[beID].[ATTRIBUTE]

Where [beID] is the single and unique identifier that the RDE assigns to each object. Valid beIDs are users, elements, devices and specific value-types identifiers. If the [beID] is omitted, it will reference to the agent's controlled object (declared in the OnObject field of the agent object).

The property [ATTRIBUTE] can take one of the following values:

TABLE 4

Symbol definitions for alarm comparison

| Attribute description | Attribute |
|---|---|
| String value inherent in the beID | ID |
| Object's name associated to the beID that provides the value | NAME |
| Object's description associated to the beID that provides the value | DETAIL |
| Data type for value-type (0 = string, 1 = number, 2 = date, 3 = binary) | TYPE |
| Magnitude associated to this value-type | MAGNITUDE |
| Unit of measure for this value-type | UOM |
| List of customized tags associated to this value-type | TAGS |
| List of standard tags (ISA 95/88) associated to this value-type | STAGS |
| Latest recorded value in the system for this value-type | VALUE |
| Last time record when latest value was saved (timestamp) | LAST_TIME |
| Last time record when latest value was saved measured in milliseconds | LAST_MSEC |
| Current time record when this value is being saved (timestamp) | CURRENT_TIME |
| Current time record when this value is being saved measured in milliseconds | CURRENT_MSEC |
| Get the calculation of the trend of this value based on latest values. | TREND |

4.10.2. Action Definition

In response to an alarm, an action is triggered. The system checks a minimum time (configurable for each alarm) to launch the next action if the alarm is triggered repeatedly, to avoid undesired effects or iterative activity without areal meaning (managed by the ellapsedTimeForNextAction field). For each alarm one of the following actions could be performed:

TABLE 5

Available actions to be associated in alarms

| Action description | Action name |
|---|---|
| Sends an email with configurable subject, content and recipient. | EMAIL |
| Saves a customized record in a configurable file (in overwrite or append mode) | LOG |
| Executes an SQL query in a DB. It must be specified the connection and driver configuration for this action, that will be a static value. | SQL_DB |
| Creates a file with configurable content and saves it using FTP protocol. FTP address and filename must be configured. | FTP |
| Saves a value-type being the origin of this value, an element that is the own agent (identified by its beID). | NEW_VALUE |
| Calls a REST service by configuration. Used parameters to execute the action can be managed through the attribute definition. | REST |

The actions structure allows to dynamically build the content of the message. To build this body the same rules that were used when the Limit expression was written must be used. The following example shows how to use the syntax: Assuming a message is sent by email when the value issued by a temperature sensor exceeds the maximum accepted in the alarm:

Device's technical card to be watched over and alarm and action definition
Device Properties
beID: 413415512_01_13409013
Name: Temperature Sensor 893
Description: Temperature sensor for white room
Serial number: TLK-143408055
UOM: ° C.
Magnitude: Temperature
ISA 95/88 tags: sensor, control module
Custom tags: temperature, white room
[The device properties can also include a QR code that stores suitable information about the device]
Agent Definition
beID: 4130813422_09_508145
Name: Environment Temperature
Description: Check for standard conditions of temperature in white rooms
Object to watch over: Temperature Sensor 893 (beID=413415512_01_13409013)
Custom tags: Control of temperature, monitorization Alarms and Actions Associated to the Agent Alarm 1
beID: 4130813422_19_54598713
Name: Upper Temperature Check
Description: Check absolute upper value for ambience
Custom tags: Alarm of temperature, upper limit
Condition: >
Limit expression: 25
    Action
    beID: 4130813422_21_62476224
    Name: Send email with alarm
    Description: Sends an email with the alarm
    Custom tags: Control of temperature, upper limit
    Type: EMAIL
    Configuration
    To: QADepartment@customerA.com
    Cc: MaintenanceDepartment@customerA.com Subject: Warning. Temperature exceeded for [NAME]
Content: The sensor identified by [NAME] has recorded the value [VALUE] [UOM] at [LAST_TIME]. That is an alert defined by the system. Please contact with the administrator.
Alarm 2
beID: 4130813422_19_54598715
Name: Trend Temperature Check
Description: Check trend of temperature for white rooms
Custom tags: Alarm of temperature, trend control
Comparison Term: abs([TREND])
Condition: >=
Limit expression: 0.10
  Action
  beID: 4130813422_21_62476224
  Name: Send email with alarm
  Description: Sends an email with the alarm
  Custom tags: Control of temperature, upper limit
  Type: EMAIL
  Configuration
  To: QADepartment@customerA.com
  Cc: MaintenanceDepartment@customerA.com
  Subject: Warning. Unexpected trending of temperature for [NAME]
  Content: The sensor identified by [NAME] has recorded an unexpected trend (with latest value [VALUE] [UOM] at [LAST_TIME]). That is an alert defined by the system. Please contact with the administrator.

4.11. Special Reference to the Privacy Data

Regarding encryption property described above in 003G with respect to FIG. 3, it's worth noting that in response to activating this feature, all the information embedded in the beJSON is saved into big data using encryption, protecting thus the data inside the repository. This behavior is important for keeping private the data related with sensitive information.

Additionally to these aspects, the RDE ensures that only results not considered as private are accessible by queries using natural associations (content in Data.Value, Data.When, Data.What, Data.Why tags). The information saved in the sections Data.Who and Data.Where are never returned by default. It is necessary to force this return with an special profile that allows to display these sensitive information.

From the same point of view, the management of data published through scenarios (see Scenarios above) can only display the non-private data. The sensitive information included in the beJSON is not available by default and actors (with the appropriate profile) need to declare visible this information explicitly.

4.12. bePedigree: The Dynamic Pedigree Based on Processes

There are evident advantages when all the information across the product life is centralized in just one place: data can be accessed in a simple way, there is not interfaces, a transversal knowledge could be extracted in a natural way, etc. When this information is scattered in the RDE repository and the user performs a query, the connection of the singular records via a search criteria builds a path that links all data associated by this criteria. This path is based on the criteria that the user has introduced but, mainly managed by the natural associations (described in FIG. 4) and customized associations (described in FIG. 8). As the data recorded in the system is persistent and inviolable (the override action always keeps the previous value), the path that links the related elements can be set and identified by a special ID: the bePedigree.

Thus the bePedigree is defined as the automatic dynamic self-constructed ID through the trace of all events associated to a subset of records that exist in the RDE. When a query is saved (as a predefined query using for example the Query Builder described in the section Analytical management and trending study), the result can be saved, but also all the elements that have been involved in the final result. An example about how bePedigree could be implemented is described below.

One of the direct applications that could be applied in the pharma industry is the assurance of the authenticity of drugs. A predefined query can be established accepting as input parameter the identification of a given medicine (e.g., when the patient acquires the product in the pharmacy and the 2D code is read with a device and submitted to a web service of the brand (provided by the RDE)). A designed query could gather all the information associated to this request for the read code, adding furthermore the information coming from the requester (location, timestamp, pharmacy, etc.). All the elements that will be involved in this query are linked by a unique path ID that gathers the full trace of the product life.

5. Regulatory Layer

The RDE, by design, complies with pharmaceutical regulatory requirements for electronic data-repositories—namely FDA 21 CFR Part 11—so the application is enabled for usage in GxP environments. This section describes how the RDE builds a layer 21 CFR Part 11 compliance over the pgp concept used to authenticate users and elements and to encrypt the hashes used in the REST calls.

The system works at two different levels where the authentication must be ensured to guarantee the data source: API and graphical user interface (GUI) level.

5.1. Regulatory Layer on RDE's API Level

A public API defined in the RDE can be accessed by attended or unattended subsystems (basic connection, configured connection or smart connections). The RDE's APIs can be accessed either from the GUI as by the running background processes. Thus, the REST functions that are called by whatever mean must ensure the right behavior on the different available actions.

5.1.1. Authentication at API Level

All API calls—except the InsertValue method, which can be issued by user-less devices—require a valid user, in this case an existing user in the RDE database having associated a valid PGP public key.

The API call's content must be hashed/signed, and the user and the hash are passed together with the content so RDE is able to authenticate the user (see section Regulatory layer on RDE's GUI level). The references in the 21CFR11 that support to this authentication are:

11.10(d): Procedures and controls should include: limiting system access to authorized individuals 11.10(g): Use of authority checks to ensure that only authorized individuals can use the system.

5.1.2. Authorization at API Level

Users of the RDE are granted access to data at different levels through profiles: Data management and access to data values.

Management/configuration data: three possible levels of access per type of configuration element (i.e., users, devices, . . . ):
  No access View Manage Data values access is defined per value-type (data of a specific type obtained from a given device):

No access

View

Modify

Notice that insertValue is of public access, just based on authorized "devices" (see API access from devices).

The references in the 21CFR11 that support this are the same as the ones listed in the previous section (21CFR11 11.10(d) and 11.10(g)).

5.1.3. API Access from Devices and Elements

Devices must be registered into the RDE in order to accept data—InsertValue—from them (see detail description above with respect to FIG. 1 and FIG. 2).

The term devices and elements includes, not only physical devices, but applications, . . . in which case the actual physical source (e.g., personal computer, radio frequency terminal, smart-phone, tablets, etc.) may be irrelevant, and all values may be considered as coming from the same device or element (i.e., same value-type).

Notice that, on the other hand, the most simple physical devices will need to access the RDE through a listener implementing the smart connection that issues API calls (see detail in 002E of FIGS. 2 and 003C of FIG. 3, above).

For a given data source (device or element) plus value-type, user may optionally configure:

PGP public key: The API message content must include the hash/signature of the content, to be validated by the RDE. This PGP key may be set to expire, and may need to be periodically renewed by any of the users responsible for the device. The data sent by devices with expired PGP is stored by the RDE with the "pgp expired" status (see 003E and 003F of FIG. 3 above). User may later change this status, recognizing these received data as valid.

Require user: The API message content must include the hash/signature of the content using the logged user's private PGP key. The user PGP must be valid—must exist and not be expired—for the value to be accepted. Notice that a message may contain both the user and the device-associated hash/signature, if both have been configured for the device.

Require user with given resource/permission: on top of the above, the user must have been granted permission to enter data for this value-type—i.e., this creates an additional "insert" value-type access level, different than "modify" one described above (see Authorization at API level section).

Require user signature: The API call content must include meaning. This is configured on top of "user with given resource/permission". Notice, though, that the caller GUI is responsible for implementing the signature procedure, before issuing the pertinent API-call.

Otherwise, if no PGP signature is used, the API message must include a standard CRC to guarantee its integrity.

The references in the 21CFR11 that support this declaration are:

11.10(h): Use of device (e.g., terminal) checks to determine, as appropriate, the validity of the source of data input or operational instruction.

5.1.4. Audit Trail of API-Level Modifications

Audit trails are kept for all modifications—both management/configuration and data value—authorized above: timestamp, user and, optional (API call content), the reasons of the change are kept, on top of the original and the modified values.

The reference in the 21CFR11 that support these audit trails is:

11.10(e): Use of secure, computer generated timestamped audit trails to independently record the date and time of operator entries and actions that create, modify, or delete electronic records. Record changes shall not obscure previously recorded information.

5.1.5. Signatures at API Level

The data modifications—both management/configuration and data value—can be configured to require signature: at the API level, this is implemented requiring the API content to include a meaning, on top of the optional reason of change (described in Audit trail of API-level modifications), in the audit trail.

Additionally, an API is provided in order for the GUI to determine if a given API call requires signature, and implement it properly (see Session inactivity period in this section). Note that this meaning is part of the API content, and therefore included in the signature hash.

The references in the 21CFR11 that support the signatures are:

11.10(j): The establishment of, and adherence to, written policies that hold individuals accountable and responsible for actions initiated under their electronic signatures in order to deter record and signature falsification.

11.70: Electronic signatures and handwritten signatures executed to electronic records shall be linked to their respective electronic records to ensure that the signatures cannot be excised, copied or otherwise transferred to falsify an electronic record by ordinary means.

5.1.6. User Expiration at API Level

Validity time periods are defined for user's associated PGP public key. Once this period has expired, no API call is accepted for this user, except the one that uploads a new PGP public key (see Signatures at GUI level in this section).

The reference in the 21CFR11 that support the user expiration is:

11.300(b): Ensuring that identification code and password issuances are periodically checked, recalled, or revised (e.g., to cover such events as password aging).

5.1.7. Database Integrity is Guaranteed

CRC based on content is added to values stored in database that guarantees they cannot be altered. A periodical process runs on database to determine faked/altered value records.

The reference in the 21CFR11 that support to this database integrity is:

11.10(c): Procedures and controls shall include: Protection of records to enable their accurate and ready retrieval throughout the records retention period.

11.10(a) Software must implement the ability to discern invalid or altered records.

5.1.8. Database Query API

Values stored into the database may be retrieved at any time, and eventually exporting into files in the beJSON format using the query API set: the most basic query is by data source (device or element) plus a value-type and a time range, and it may include changed value's audit records.

The reference in the 21CFR11 that support this database query is:

11.10(b): Procedures and controls shall include: the ability to generate accurate and complete copies of records in both human readable and electronic format suitable for inspection, review and copying by the agency.

5.2. Regulatory Layer on RDE's GUI Level

The RDE implements a Management/Configuration Web-GUI, which issues API calls to the RDE itself. Notice that the users are free to build their own GUI applications using the RDE API, and they are not forced to follow the "guidelines" below, provided they fulfil the API requirements described above. In this section is described how the GUI ensures the regulatory constraints with specific dependency on the graphical interface.

5.2.1. GUI Session

Users can start the session on the GUI logging with their username and password. The password component displays a random number (typically one through three) of wildcards for each typed keys.

The Web-GUI interacts with the local PGP-safe repository application to retrieve the PGP private key for that user, using the given password.

The GUI code builds the API call content and hashes it using the PGP private key; it includes this hash, along with the user code and the call content.

An initial API is available to check if the user is valid in the RDE. The GUI caches the PGP private key and uses it for all the API calls issued from the standing session, until the user eventually logs off, when the cached PGP is trashed.

5.2.2. Session Inactivity Period

The RDE GUI implements a session inactivity period (configured in the RDE, and made available to the GUI via an specific API). Once this time has elapsed without user activity detected, the GUI flushes the cached PGP, and the user is required to re-enter the code and the password to retrieve it again from the safe-repository and continue the session.

5.2.3. Signatures at GUI Level

The API to determine whether a signature is required for a given data modification call is available, so the GUI can implement it properly (i.e., requesting a user/password along with the associated data, and properly build an API call content including meaning).

The RDE GUI follows this implementation.

5.2.4. Password/PGP Change from the GUI

A user can trigger a password and/or PGP public key change at any time. The user is obviously forced to do so when the PGP is expired in RDE: The API calls are rejected. The RDE allows configuring a required password strength: this configuration is made available to the GUI apps via an API-downloaded script. Thus when this script is called passing the old and new (entered twice) passwords, it determines:

The new password is different than old password
The new password has the required strength: length and characters of 2-4 different sets (lower-case, upper-case, numbers and symbols)
Both entries of the new password match The GUI then uses this new password on the local PGP-safe repository to create a PGP key pair, and builds an API content for the call to update the RDE user PGP public key: this API content is hashed via the previous PGP private key.

The RDE GUI uses this script to validate the password change. However, other GUI-apps are not required to do so, in order to create a new PGP key pair.

Additionally, the RDE can be developed under a GAMP 5 based quality system, so it fulfils 21CFR11: 11.10(a): Procedures and controls shall include validation of systems to ensure accuracy, reliability and consistent intended performance. GAMP is the acronym of Good Automated Manufacturing Practice. Under this concept there is a set of guidelines for manufacturers and users of automated systems in the pharmaceutical industry (more information in the book "GAMP 5 Guide: A Risk-Based Approach to Compliant GxP Computerized Systems" (2008), which can be found at, http://www.ispe.org/gamp-5, and which is incorporated here by reference).

6. GUI Elements to Manage the RDE

This section shows different screen's structures that are intended to provide an approximate idea about how the GUI looks for the main functionalities with an added value on the system. The GUI that are not giving an added value are only described but not drawn (e.g., screens used to manage maintenance elements) unless they show a special feature to be considered under the patent framework. The proposed screen's structures are grouped by the different features that are covered.

6.1. Master Data Maintenance

Maintenance for owners and related audit.

This maintenance is accessible by the user that generates the owner account. The owner is the entity (pharmaceutical, biotech, regulated industry) who pays for the service. The associated objects (users, elements, equipment, processes and views) can be accessed from this screen, but that is not the usual way. The purpose of this screen is maintenance and is related to the commercial transaction associated to the owner (payments, accounting, consumptions, etc).

The associated audit to the owner activity is also accessible from this screen.

Maintenance for users

Screen that displays main data to define users.

The beID generated by the system that guarantees the uniqueness in the RDE is shown in a Quick Response Code (QR) code format to facilitate its access. Also a print action is available for this QR code associated to the beID.

Additional tabs in the form visualize the position of this object in the different associations where it is involved (object associations, view processes).

Audit related to the activity of the object and the issued information is accessible from the audit tab.

Figure 21:
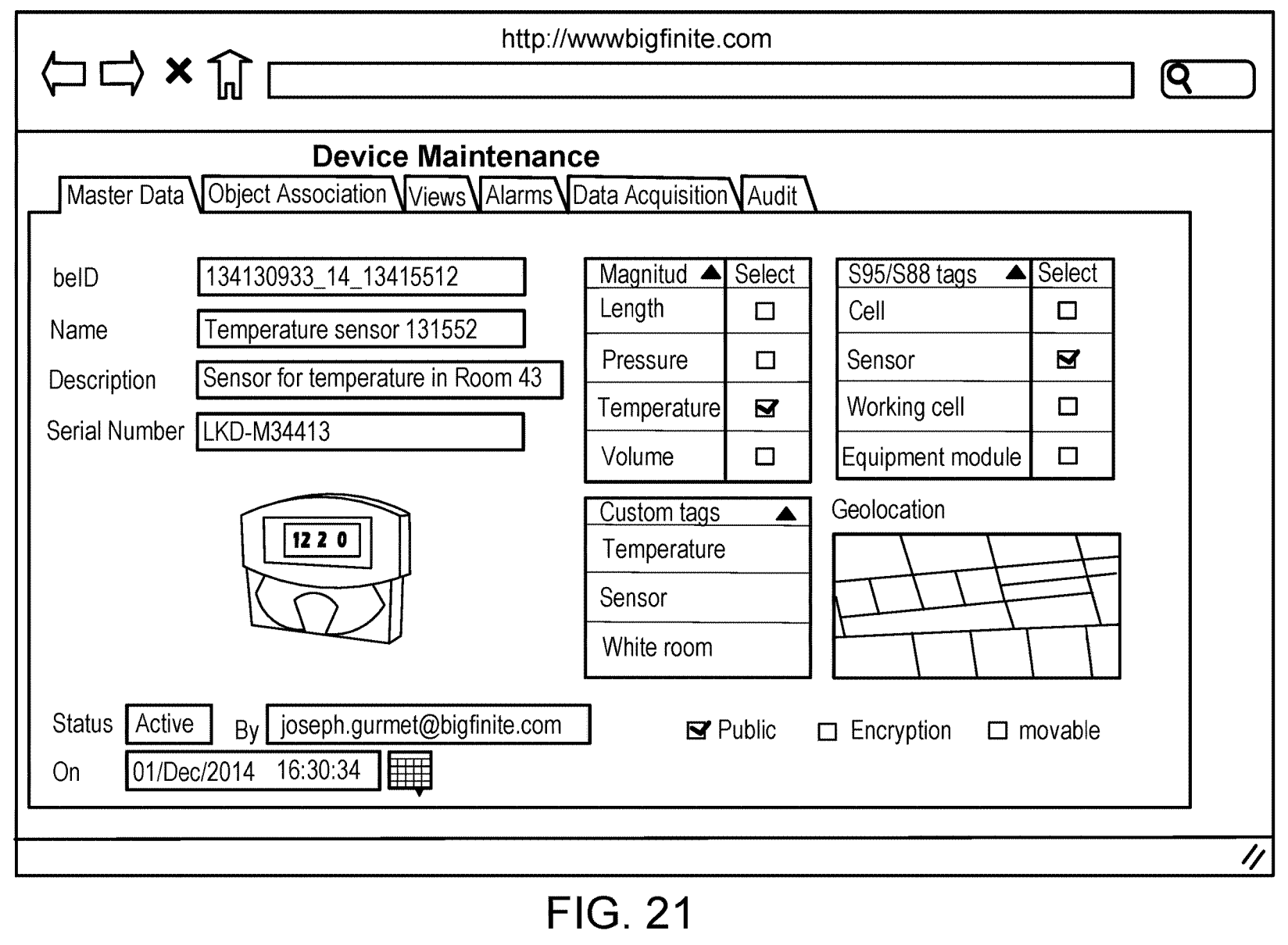
Figure 22:
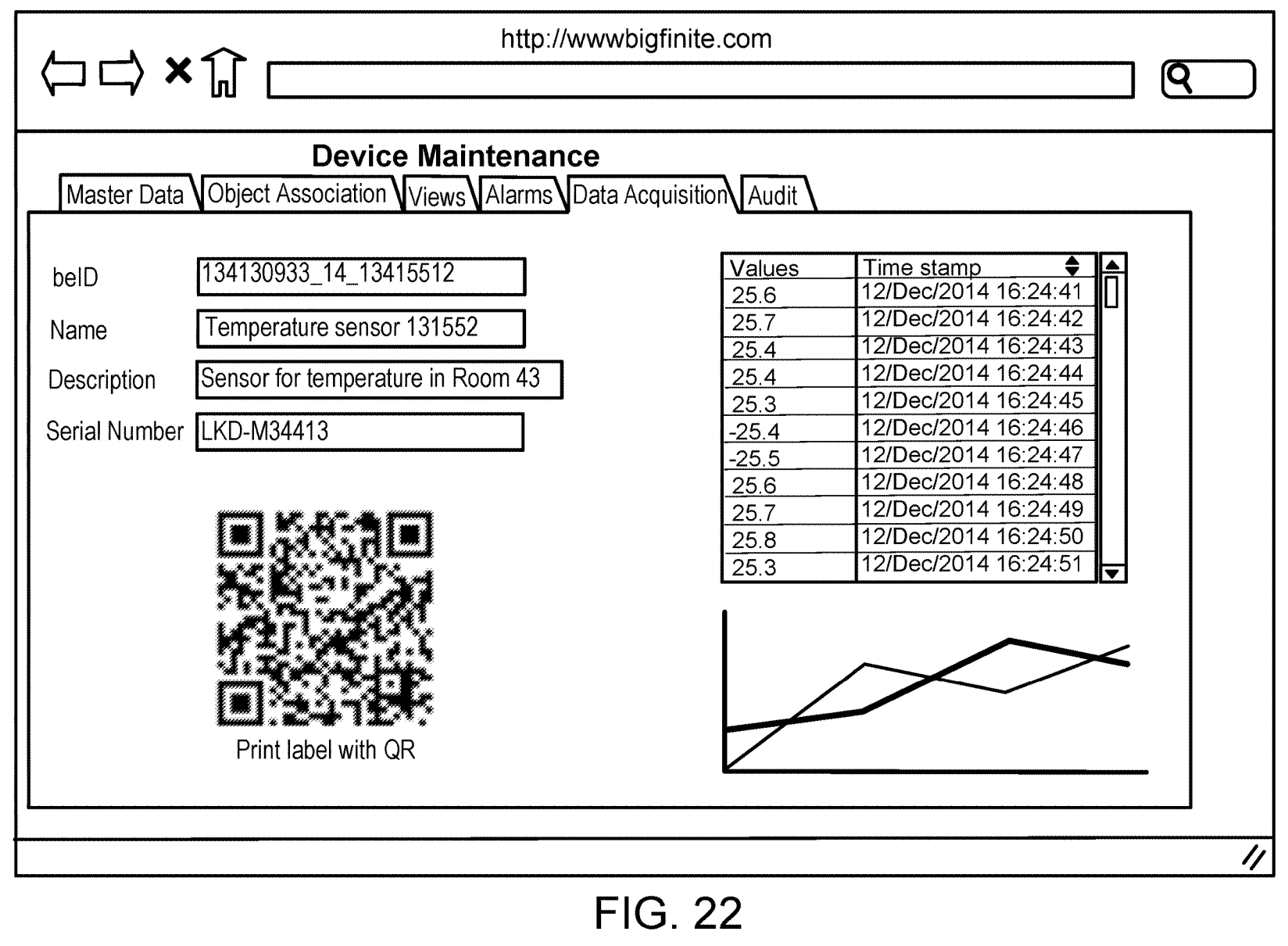

Maintenance for sources of raw data (elements and devices). The user interfaces represented in FIG. 21 and FIG. 22 show a possible way to manage this information in a graphical way.

Screen that displays the main data to define elements and devices. An example interface is shown in FIG. 21. In the same screen is displayed the associated magnitudes, standard and customized tags, status and the rest of relevant information.

The beID generated by the system that guarantees the uniqueness in the RDE is shown in a QR format to facilitate its access. Also a print action is available for this QR associated to the beID. An example interface is shown in FIG. 22.

Additional tabs in the form allow to visualize the position of this object in the different associations where it is involved (object associations, view processes).

An extra tab informs about the alarms and actions associated to the different value-types issued by this object.

The audit related to the activity of the object and the issued information is accessible from the audit tab.

Profile and access rights maintenance SA profile is a group of resources about what a user can do.

From this screen a user can establish the association of profiles to users.

The audit related to the activity is available also from this screen.

Object association management. Objects belonging to an owner environment (items of a plant, devices and users) are interrelated in different ways.

The screen where the objects associations are managed enables to establish customized relations between the objects that are in some way related each other.

These relationships can be configured recursively: an object can contain other elements. Thus an equipment (e.g., an oven) may contain other equipment (e.g., temperature and humidity sensors).

This GUI presents a tree structure type that allows drag & drop objects keeping the required structure. From this screen there is a utility that allows to see all the relationships in a flat way for a specific node.

Process and views creation. Management of objects associated to the processes at the different phases INPUT, WHILE and OUTPUT.

Figure 23:
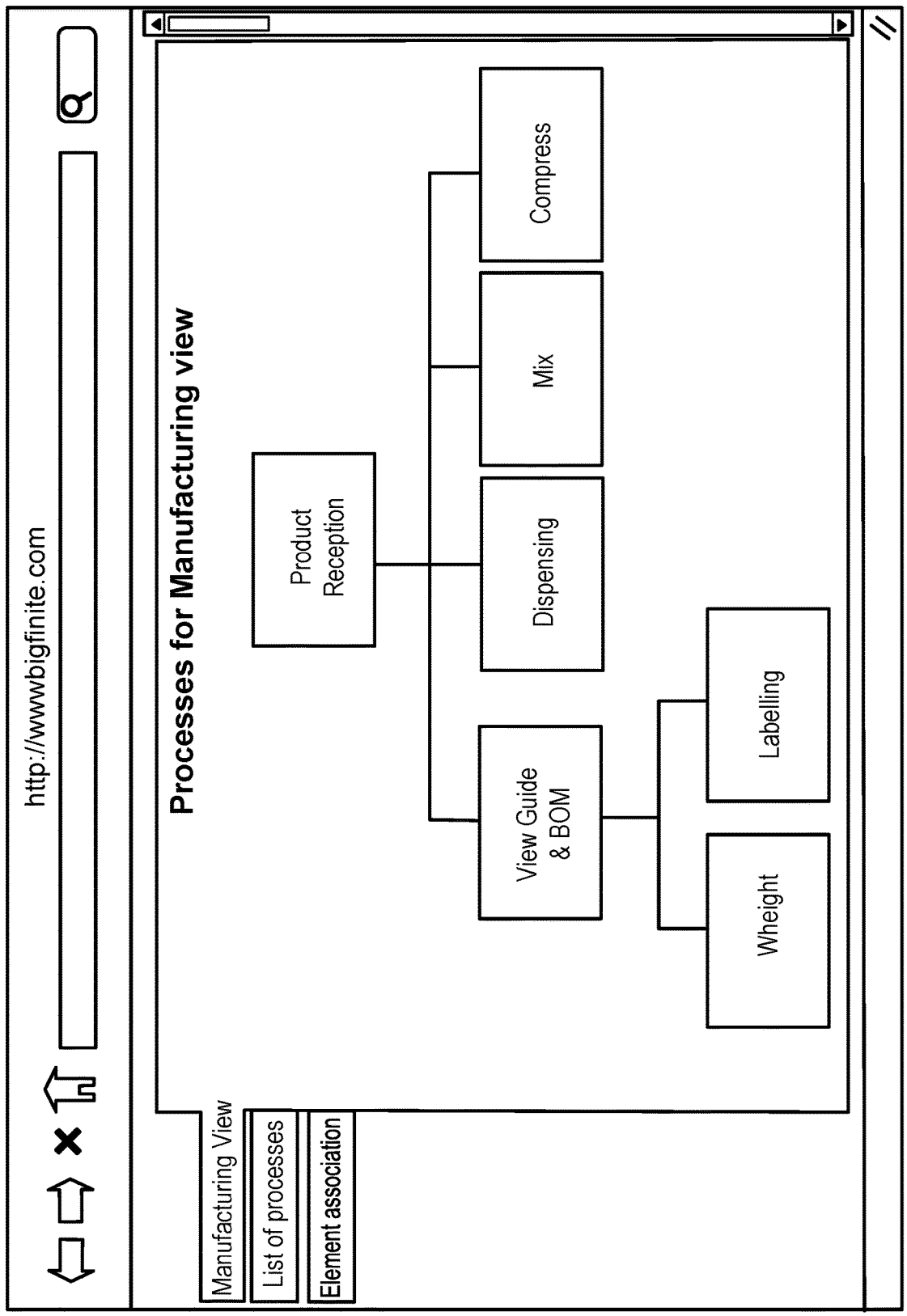
FIG. 23 is an example user interface showing processes and views maintenance activity.

A first tab allows to create the concept of views as a set of processes. For example solid manufacturing for solids, packaging, maintenance, etc. An example interface is shown in FIG. 23.

A second tab allows to create processes (only the definition and types). For example, product reception, bulk review, labelling, mixing, drying, etc. An example interface is shown in FIG. 24.

A third tab allows to associate objects to processes and processes with each other (like a PERT chart). In this tab, the user is be able to associate for each process the devices, users and elements that have been defined. The association can be done in three different phases for each process: INPUT, WHILE, OUTPUT. An example interface is shown in FIG. 25.

Scenario management. A set of different objects previously defined as public can be linked to a scenario that groups their values for a given time range. This screen allows the following actions:

The screen shows a screen similar to the user creation. Special actors with only read permission can access to a new scenario.

This GUI presents a tree structure type that allows drag & drop public objects to the scenario. The data issued from associated objects will be available only to published actors (users of scenarios).

6.2. Graphical Activity for Regulatory Topics

Figure 26:
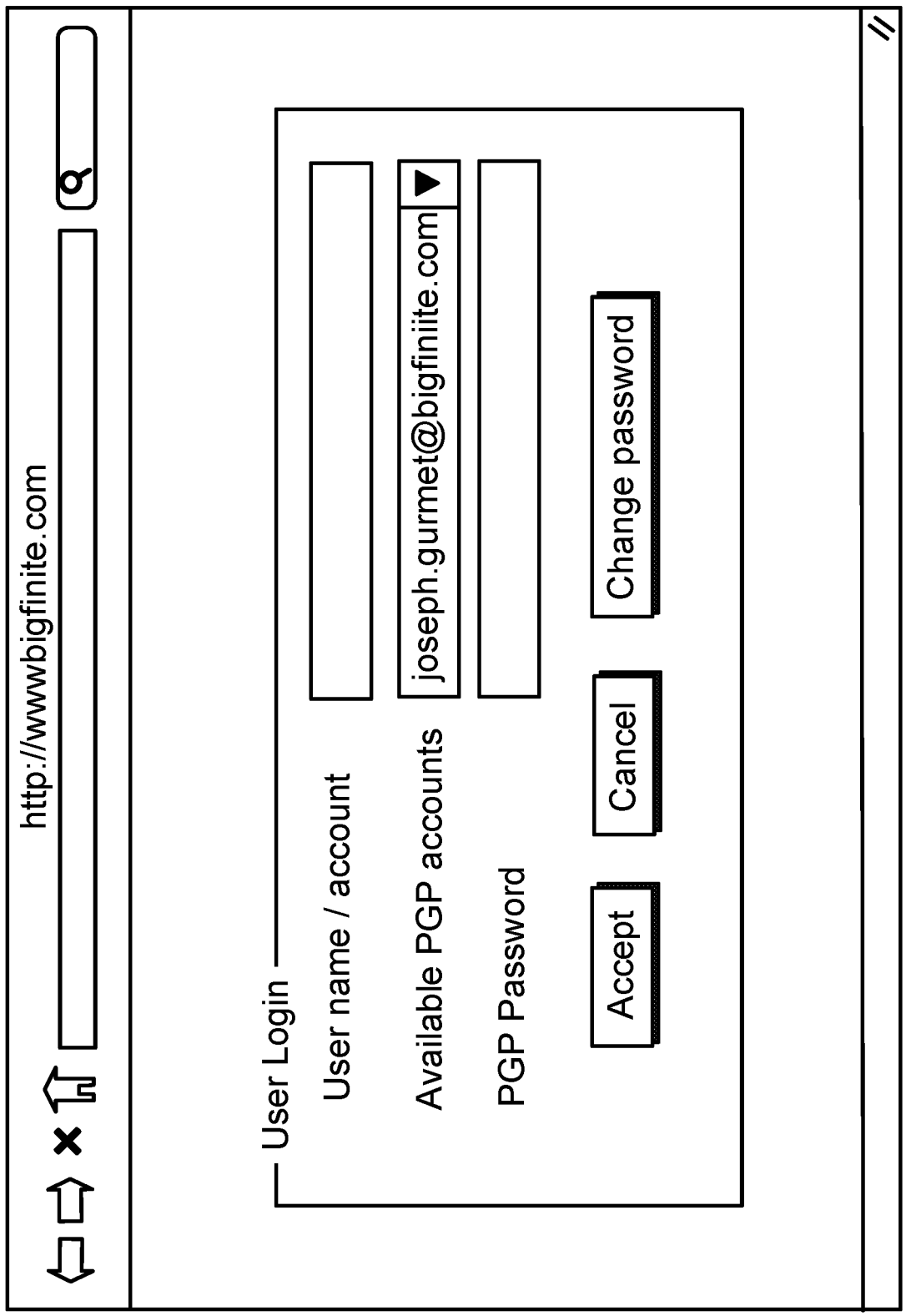
FIG. 26 is an example user interface showing login activity.

Regarding user authentication (e.g., electronic signatures), login, PGP association and expiration the following GUIs are considered:

User's login window (user/password). An example interface is shown in FIG. 26.

Simple management of user profiles to allocate and assign a PGP key

Set the password expiration and/or public key

To display the user, element and device activity it is proposed screens showing this content:

View the actions performed on any object of the system (which have been recorded by direct activity of the user): login failures, valid access, IP from which they entered, geolocation (smart phones), used browser, etc.

View the connections and disconnections caused by elements and devices (login, end of session, missing data as information sent without geolocation, records with unexpected IP, etc.)

Traceability module

View for trace system (API calls, actions taken, stored changes, triggered alarms and actions)

Change of status, log of user, element or device activity.

Module to override a value that has been recorded in the RDE (see Regulatory Layer section). An example interface is shown in FIG. 27.

6.3. Analytical Management and Trending Study

Figure 28:
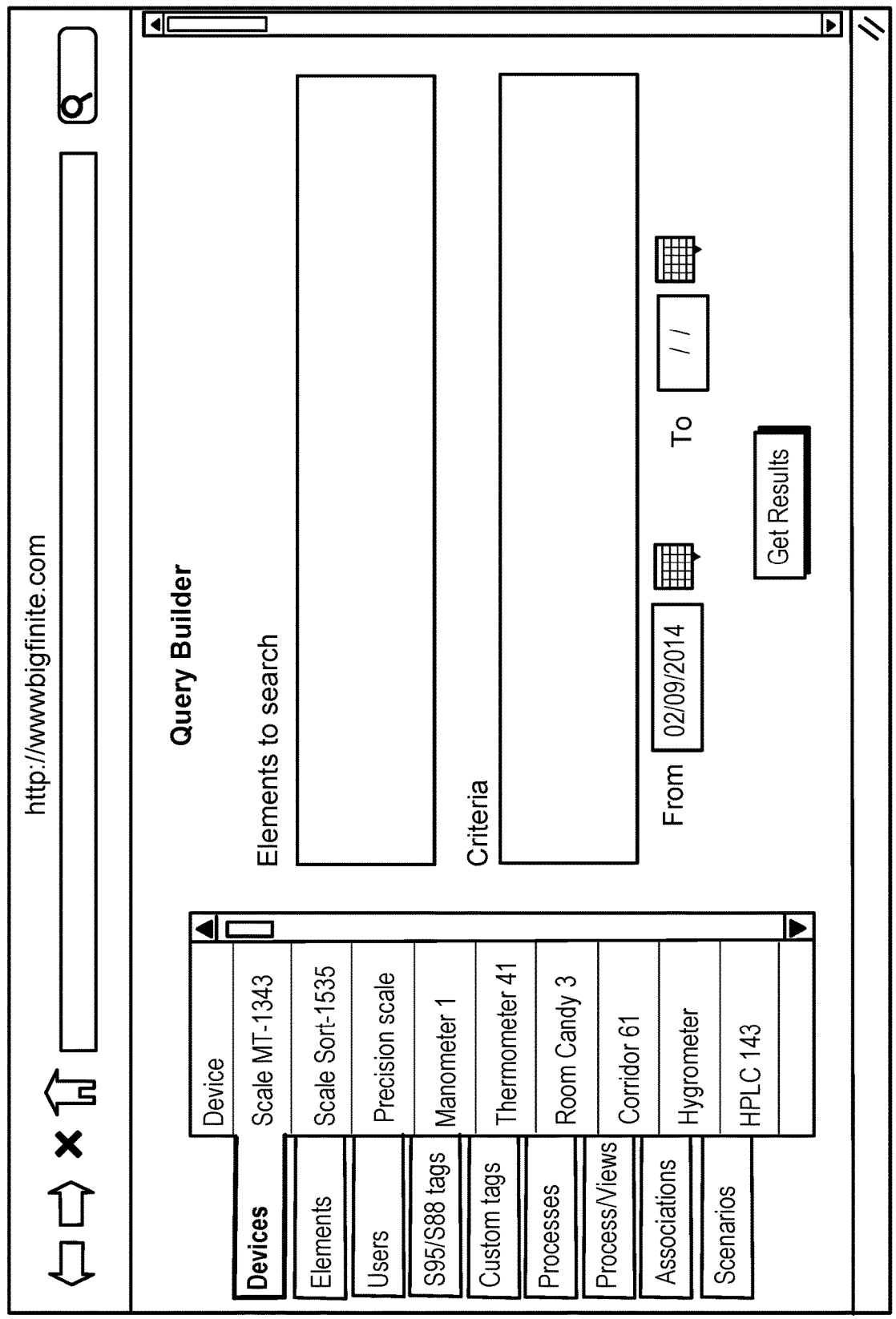
FIG. 28 is an example user interface showing a query builder.

To elaborate analytical and trending studies it is required in first place to prepare the elements that will composite the body of the query to be performed. The builder of the query should be managed by a form with the following features. An example interface is shown in FIG. 28:

The frame will save the queries and certify them for later use. It also displays the associated workflow audit of the queries. It has different graphical objects that can be drag & dropped and that compose the query.

Shows a palette with different components within the system (devices, elements, users, profiles, object associations, views, processes, timestamp, etc.). Making a comparison with SQL queries, these elements constitute the SELECT and WHERE concepts of the traditional query.

The form contains a canvas with the selected objects and configured conditions and filters. The values of the elements in this canvas will be dragged and shown as a result of the query. The Users are able to refine the search criteria making successive approaches with the available objects.

A dragged bean based on a timestamp component will appear. This calendar allows to specify the start and end of the period in which the search must be limited.

Finally a button executes the designed query. By clicking out in the results tab, the information will be displayed.

A query could be managed following a workflow based on an edition/verification/certification/archive life cycle.

Figure 29:
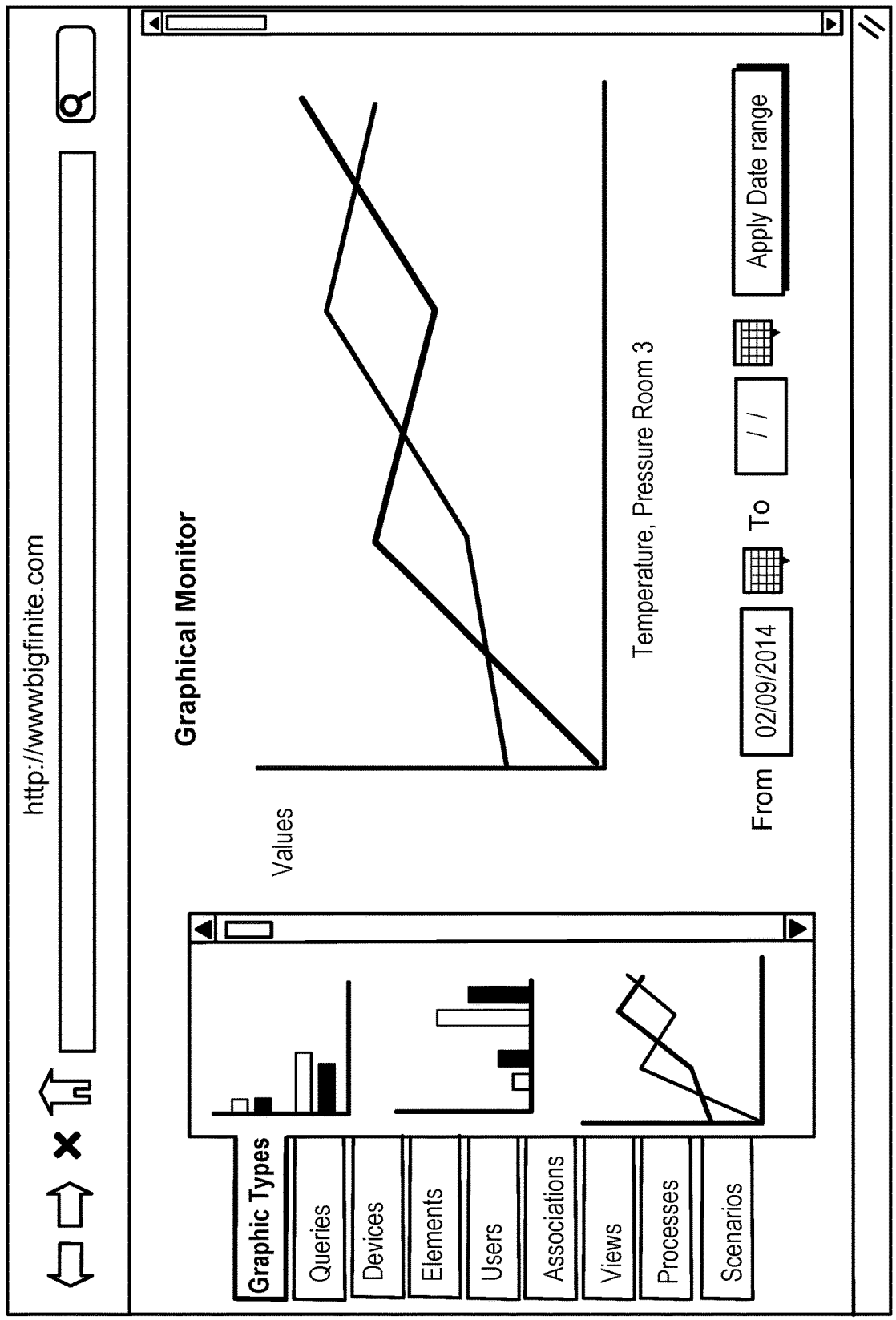
FIG. 29 is an example user interface showing a query graph.

Graphical tool to display query results. This feature is located in a frame that allows to associate the result of a query inside a graph for different purposes as could be monitoring, stabilities, trendings, etc. An example interface is shown in FIG. 29.

This form shows a palette with different graphics (bars, lines, distribution, correlations, etc.). User can associate a pre-defined query to a given selected component. The graph shows real-time query results (e.g., temperature vs. time stamp). If allowed to include series, the last field always will be the X axis, for example, show humidity, temperature and pressure vs. time stamp.

A graph could be managed (similar to the pre-designed queries) following a workflow based on an edition/verification/certification/archive life cycle.

Information about the displayed data appears in a text area or a status bar. Status, label permissions, public attribute, encryption, computation time and additional information will be associated automatically to the query's execution.

The graph can be saved in order to be shown later.

Figure 30:
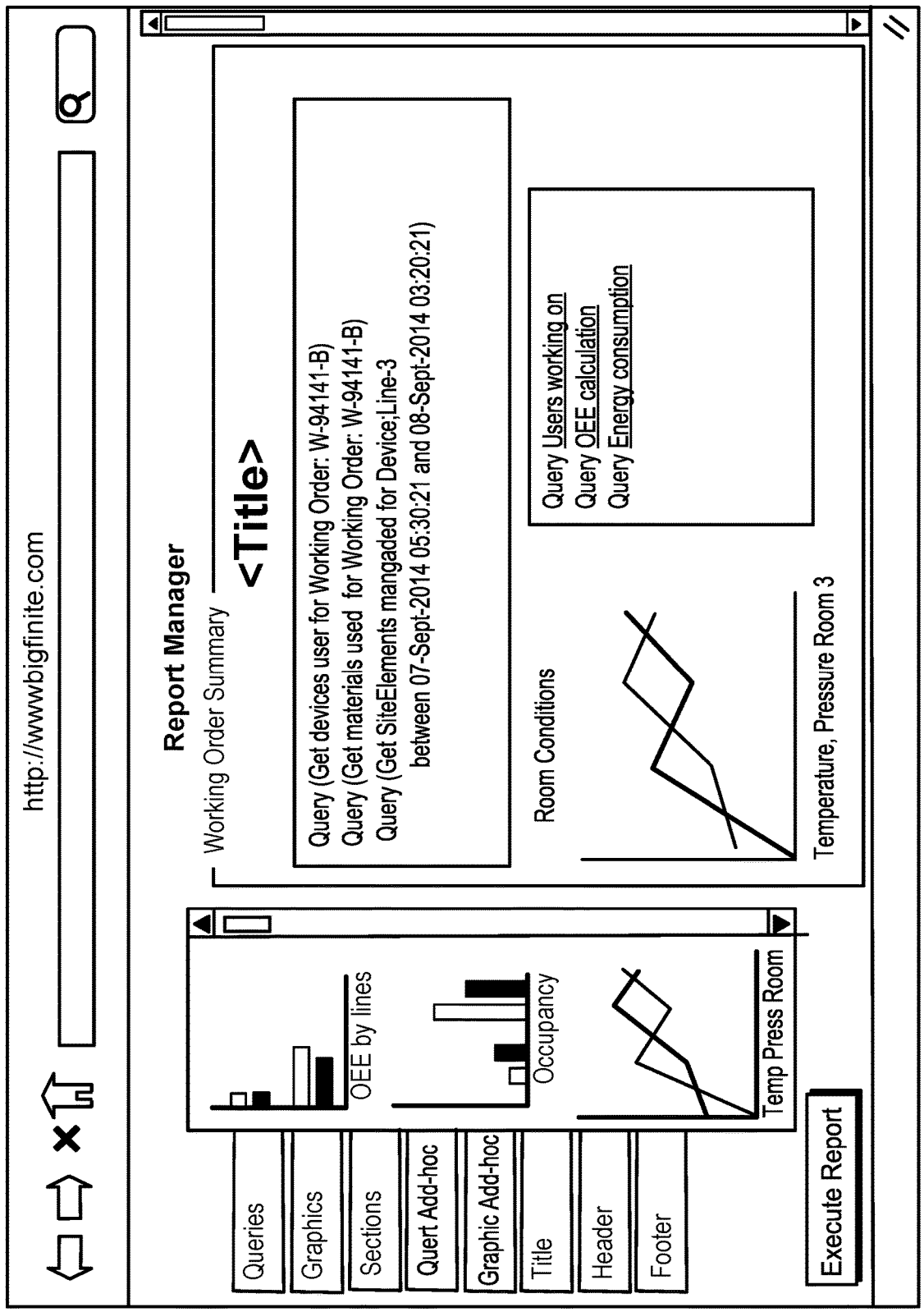
FIG. 30 is an example user interface showing a report manager.

Report manager (based on query builder). Frame that allows to associate the result of different queries and graphics in one document. An example interface is shown in FIG. 30.

A palette shows the available graphics that previously have been created and defined.

From this frame a user can go to the same graphic's palette to create ad-hoc reporting as the Graphical tool does.

It is available the same palette to make queries that the Query Builder provides.

Bands can be incorporated into a document as used in dynamic designers of websites or blogs.

The forms include a button to execute the document and pre-visualize the data. If a document is properly designed, its content should be parameterized. Thus, a document can be used to manufacture different orders, products, equipment, users. With simply changing the setting data, it will show different information but with the same layout.

A report can be saved (similar to the pre-designed queries) following a workflow based on an edition/verification/certification/archive life cycle.

Information about the displayed data appears in a text area or the status bar. Status, label permissions, public attribute, encryption, computation time and additional information will be associated automatically to the query's execution.

The graph can be saved in order to be shown later.

6.4. Checking Information Associated to an Object in Real Time

Each object in the RDE is univocally identified by its beID. Reading the QR associated to an object (hyperlink with the beID), the information of this object is shown in this form.

The frame shows the master data related with current object.

Pushed information in real time is available for all the magnitudes.

Alarms and related actions are accessible from this form.

From this screen should is also possible to navigate to the related object through process and object associations.

Trends for the current object is another feature available from this screen.

Figure 31:
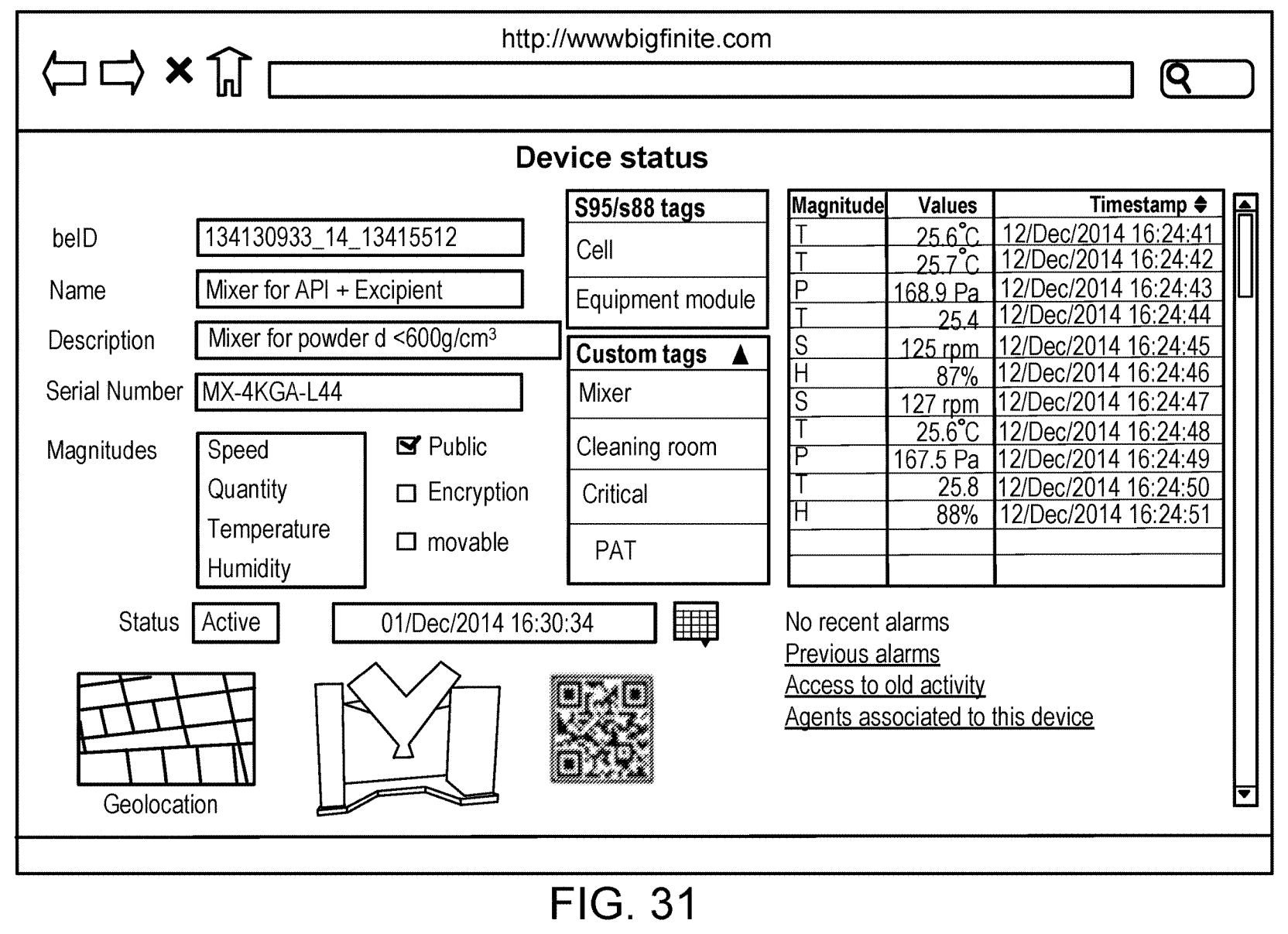

An example interface representing how the information could be presented in real time is shown in FIG. 31.

7. Data Workflow

Figure 32:
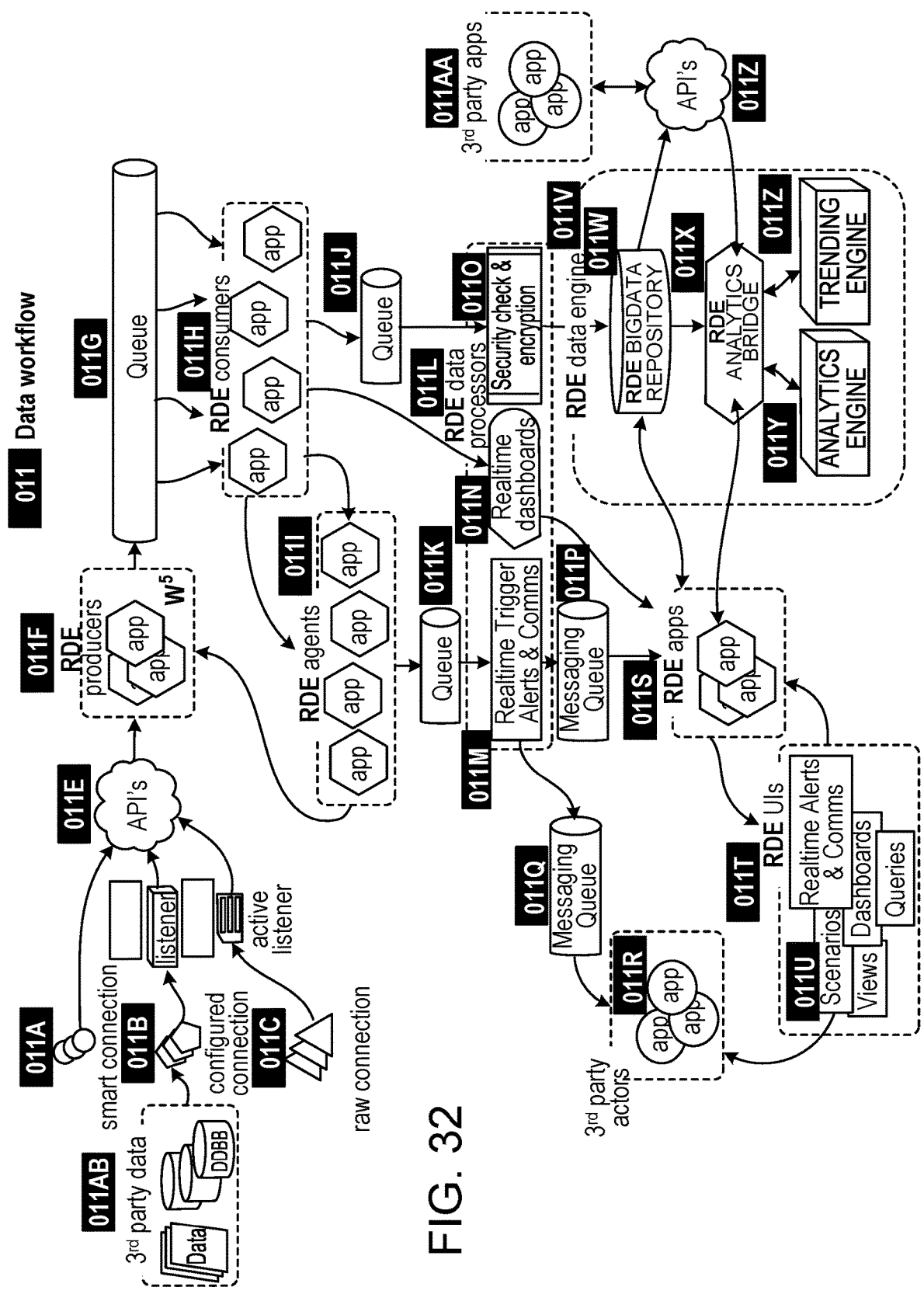
FIG. 32 is a diagram illustrating an example data workflow and components involved in data management.

A global vision of this workflow and its architecture is represented in FIG. 32.

Figure 33:
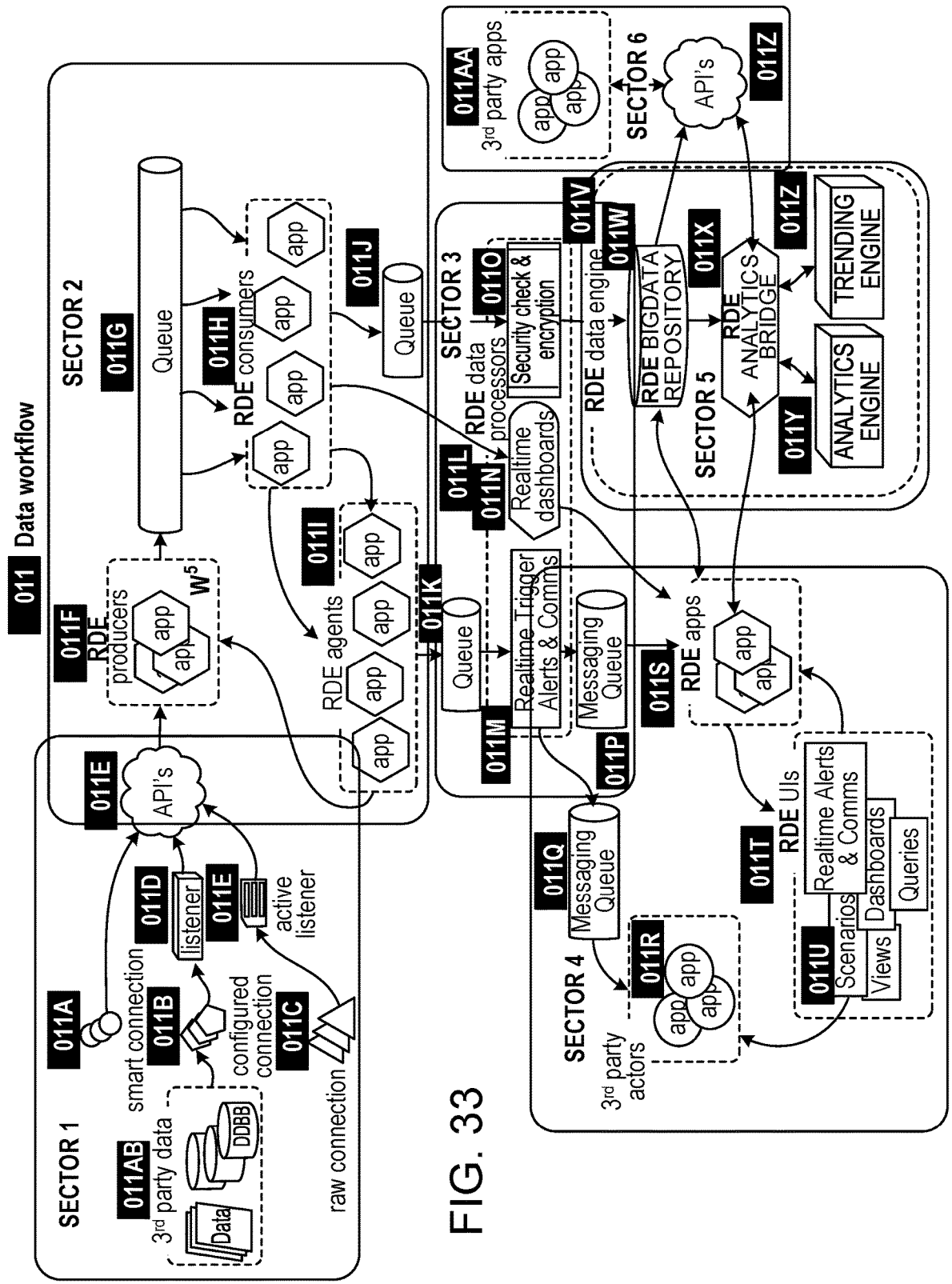
FIG. 33 is a diagram illustrating an example sectors subdivision of the data workflow of FIG. 32.

For this purpose the graph will be subdivided into sectors, in aim to give a more detailed explanation of its components. The graphic shown in the FIG. 33 shows the sectors dividing the data workflow. All labels referenced in this section are identified in FIG. 32.

7.1. Sector 1—Raw Data Feeding

Figure 11:
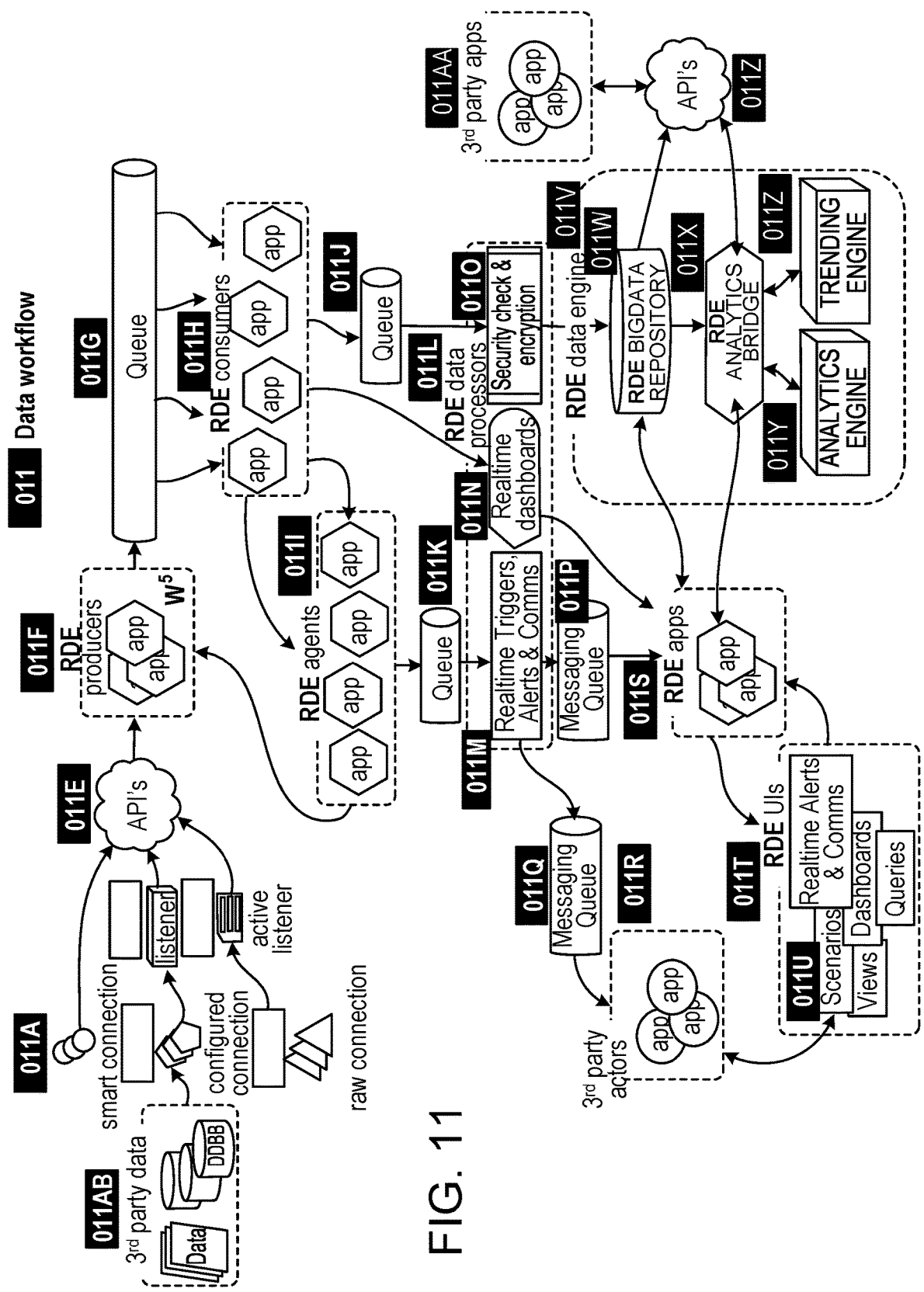
FIG. 11 is a diagram illustrating an example data workflow.
Figure 34:
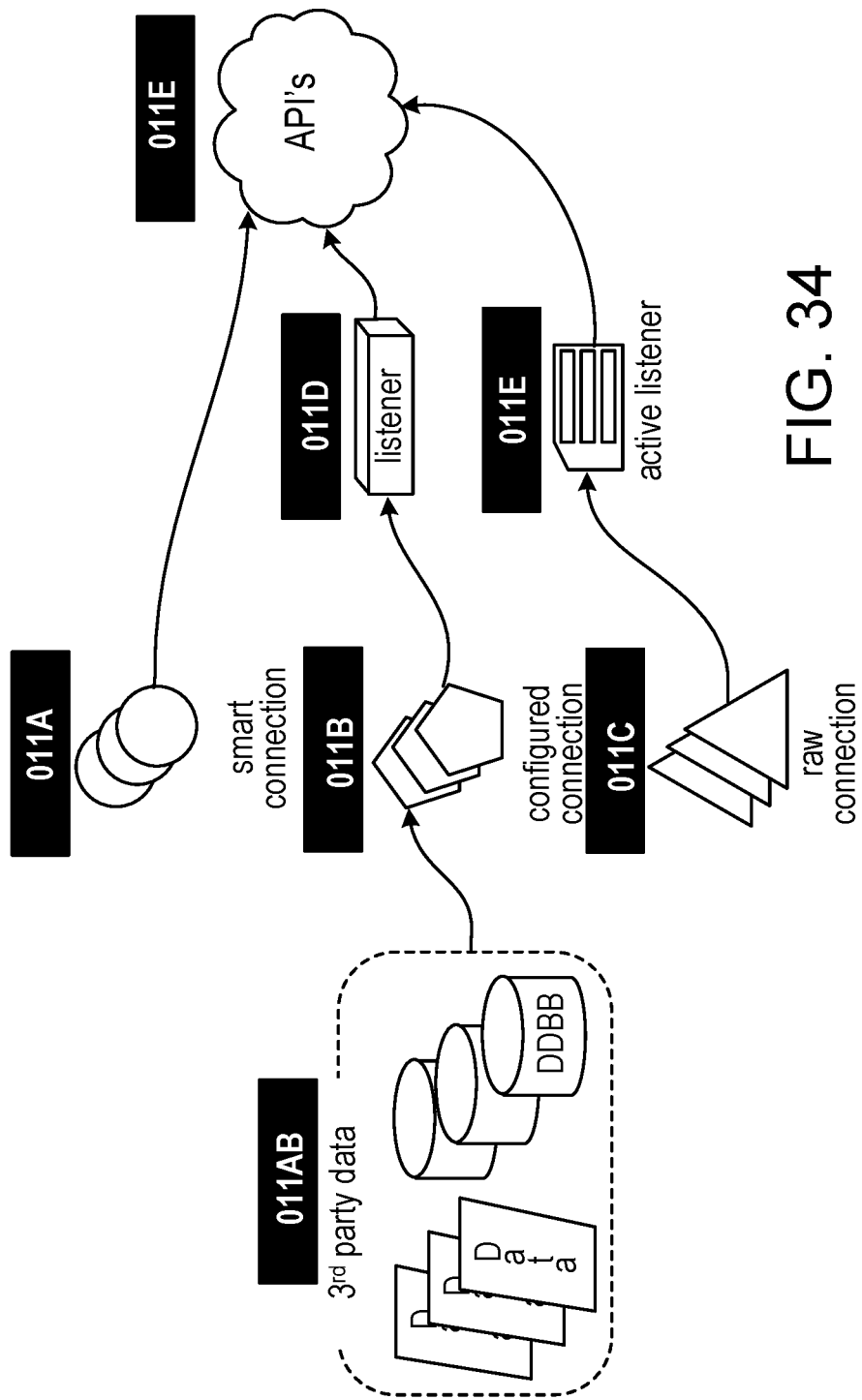
FIG. 34 is a diagram illustrating an example of a first sector of the data workflow of FIG. 33.

The workflow associated to this sector is described with respect to FIGS. 11 and 34.

This sector of the workflow depicts the raw data ingestion (prior to its processing). This ingestion process consists in the data gathering from different types of devices, as explained in section 4.3 of this document, "Data acquisition".

Three main type of acquisition devices are depicted (represented in FIG. 34):
011A: Smart connection
011B: Configured connection
011C: Raw connection Configured connections are able to import third party data (as shown in 011AB) consisting in any type of data in electronic format.

Configured connections also require of a listener (011D), a hardware data feeder with an embedded middleware able to connect to the configured connection devices (011B) and send the data to the RDE through REST calls to the RDE's API.

In a similar way, raw connections devices (011C) require also of a data feeder (shown in the figure as active listener 011E); in this case the data feeder requires of physical connections with the raw connection devices through a standard port (RS232, USB, etc.).

All data feeders, as well as the smart connections, are able to connect to the RDE's API, perform an authentication, get an authorization and send the data to the RDE system to perform all the data processing as explained in section 5—"Regulatory layer".

Prior to the data sending, data feeders and smart connections should perform a device and element identifications (Section 4.2) and proceed to the data sending for the RDE system be able to execute the data acquisition (section 4.3).

7.2. Sector 2—Raw Data Wrapping: RDE Producers, Consumers and Agents

Figure 35:
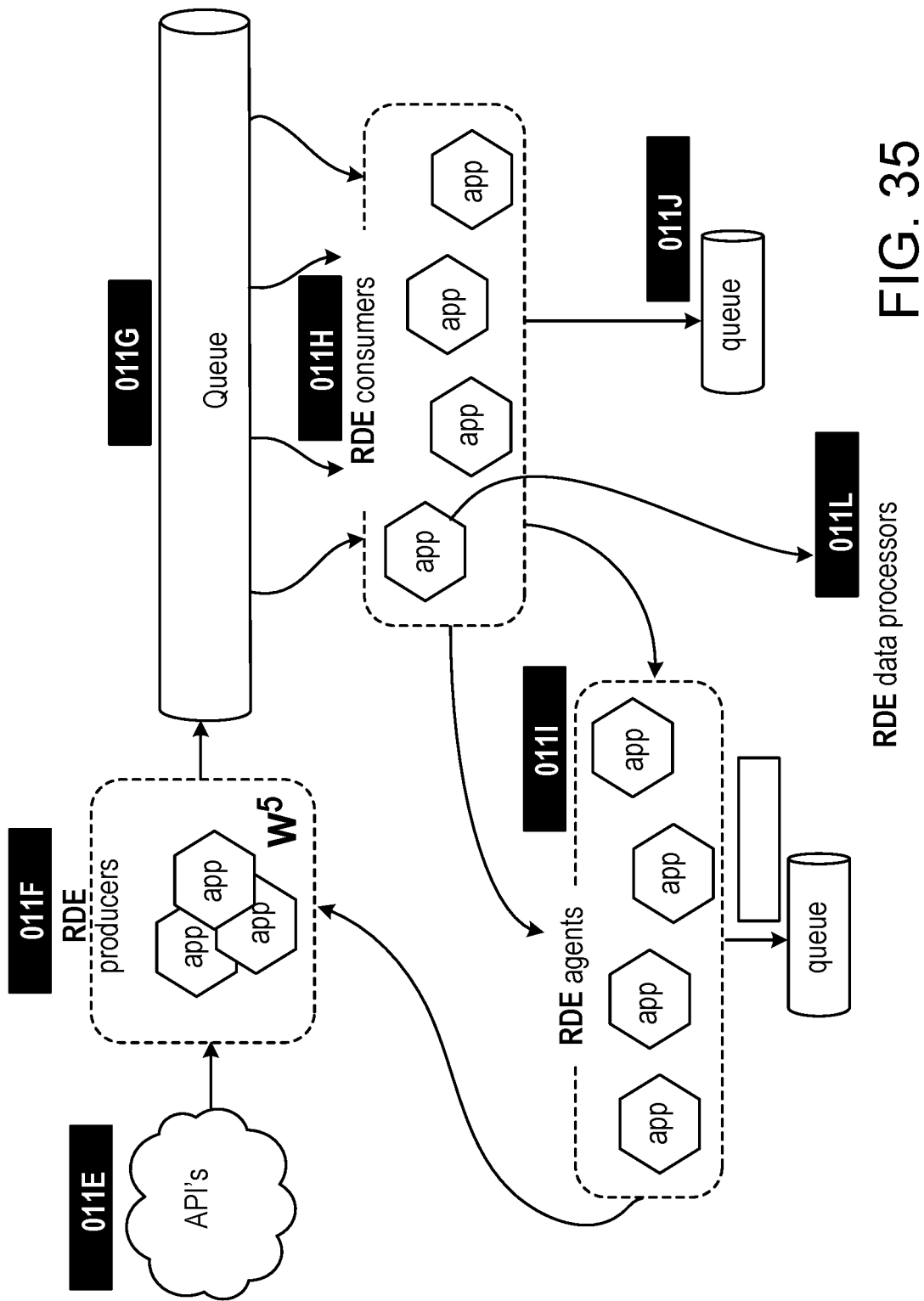
FIG. 35 is a diagram illustrating an example of a second sector of the data workflow of FIG. 33.

The workflow associated to this sector is described with respect to FIGS. 11 and 35.

Sector 2 comprises the data wrapping process (for ensuring data compliance) and its processing and agents actions on this compliant data.

Once the data reaches the RDE system through the API (011E) by means of the data feeding process (sector 1), data is gathered by the RDE producers (011F), this producers perform the data wrapping as described in Sections 4, 5 and 6 of this document.

Once data is wrapped with the $W^5$ protocol it is send to a queue (011G) where it is made available to the RDE consumers (011H) who analyze this data.

The RDE consumers (011H) can take different actions on the data received:

A. If the device who produced the data, or the data itself, has an associated agent, it is sent to the RDE agents (011I).

B. If the device who produced the data, or the data itself, does not have an associated agent, it will be sent to the RDE Data Processors queue (011J). In parallel, if it's required, it can also be sent to the RDE Data Processors in charge of the Real Time Dashboards Queue (011L).

The RDE Agents (011), in turn, can also perform several tasks:

A. Perform the needed transformations they are in charge of (as described in Section 4.10.—"010-Agents" of this document), and then submit them again to the RDE Producers (011F).

B. Submit data to the Real Time Triggers, Alerts and Communications Queue (011K).

Both tasks A and B can be performed in parallel.

7.3. Sector 3—Data Processing: RDE Data Processors

Figure 36:
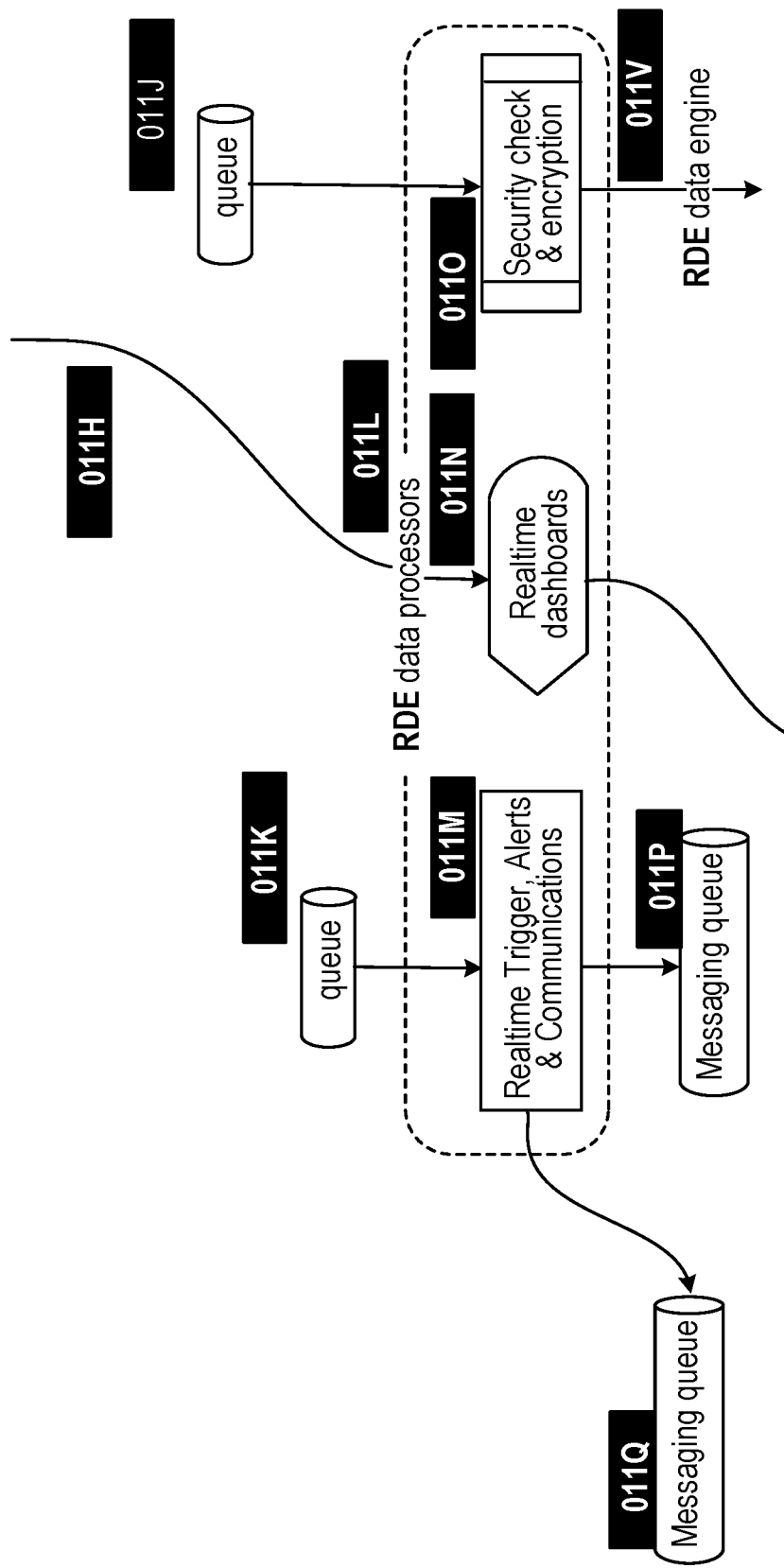
FIG. 36 is a diagram illustrating an example of a third sector of the data workflow of FIG. 33.

The workflow associated to this sector is described with respect to FIGS. 11 and 36.

The RDE Data Processors (011L) are the ones in charge of performing operations on the data once it is compliant, after processes in Sector 2 transformed the Raw data (coming from Sector 1) to Compliant Data. This transformation is described in the 003D, 003E and 003F blocks in the FIG. 3.

The RDE processors can perform several actions:

A. Security checks and encryption (0110), if needed, to the data portions that are marked to be encrypted (for security and/or privacy reasons) and hand it to the RDE Data Engine (011V). Detailed in 003G block of FIG. 3.

B. The RDE processors can also expose the data to the real time dashboards (011N) to be later consumed by the RDE Apps.

C. Submit data to the Real Time Triggers, Alerts & communications processor (011M), who will submit this data to the appropriate queue for messaging (011Q and 011P).

Two or more of this actions can be taken for every individual data received by the RDE Data Processors (011L).

7.4. Sector 4—Data Storage, Analytics and Prediction: RDE Data Engine

Figure 37:
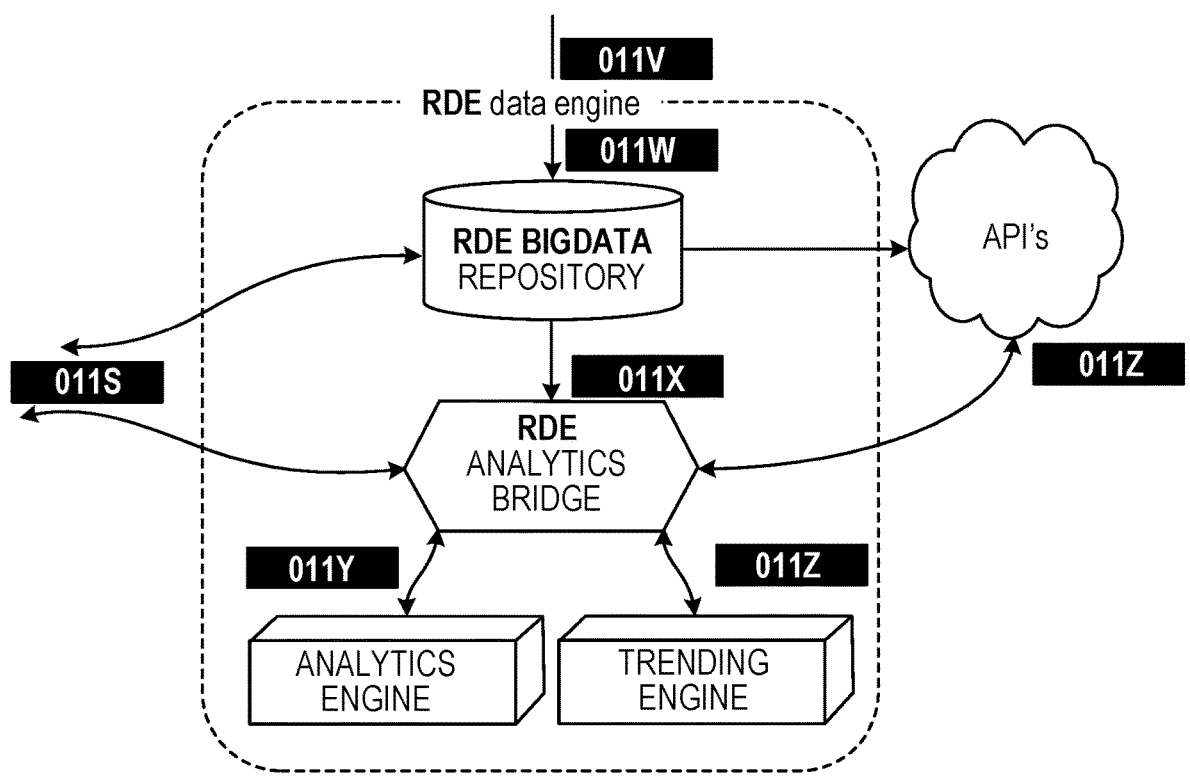
FIG. 37 is a diagram illustrating an example of a fourth sector of the data workflow of FIG. 33.

The workflow associated to this sector is described with respect to FIGS. 11 and 37.

The RDE data engine is where data is stored, in a Big Data unstructured data Repository (011W), and it is analyzed: analytics (011Y) and prediction analysis (011Z) is performed, through the analytics bridge (011X).

To note that Big Data Repository (011W) is a Compliant Repository and can, therefore, store and manage Regulatory Data. Also, by means of the Analytics Bridge (011X) this Regulatory Data it can be analyzed by the Analytics Engine (011Y) preserving compliance and also obtain Tending and Prediction information in the Trending Engine (011Z) always in a Regulated way and preserving and ensuring the compliance of the data.

The RDE data engine is also able to expose the data to the RDE Apps (011S) who consume and present it to the users and the API (011Z) that offers this data and associated knowledge to third party actors or apps. The expected API to manage this functionalities are described in the API methods to get values for trend purposes section. The associated GUI is proposed in the Analytical management and trending study section.

7.5. Sector 5—Data Consumption: RDE Apps and Uis

Figure 38:
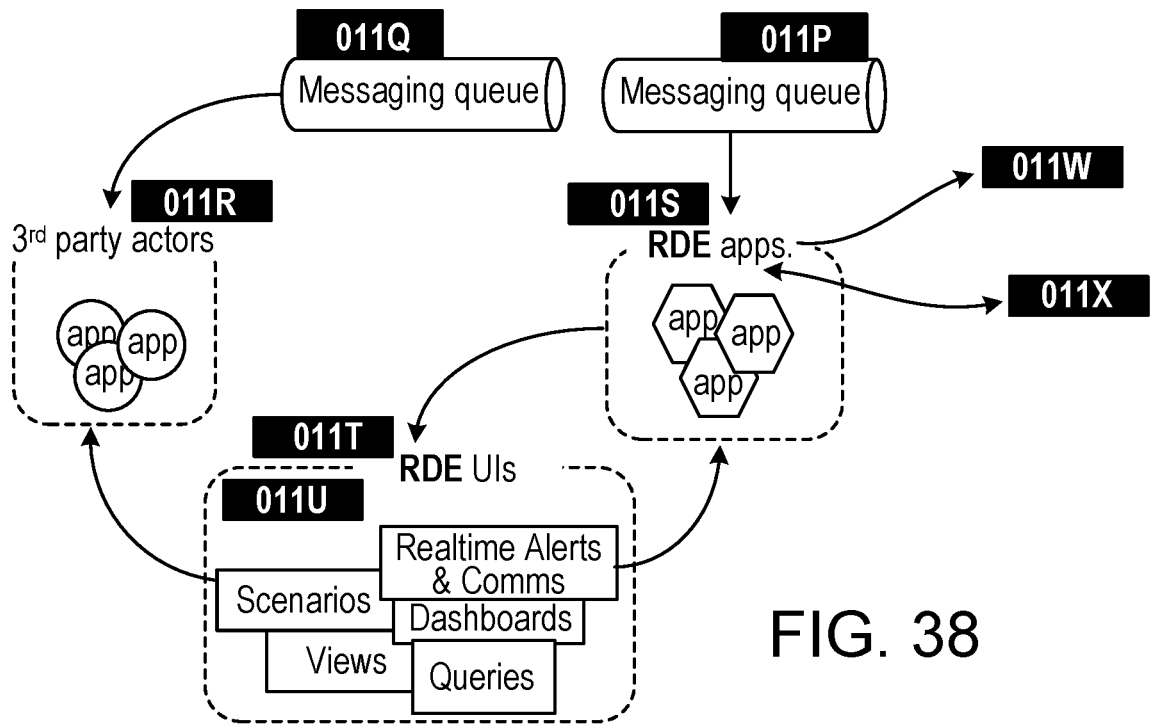
FIG. 38 is a diagram illustrating an example of a fifth sector of the data workflow of FIG. 33.

The workflow associated to this sector is described with respect to FIGS. 11 and 38.

RDE Apps (011S) and RDI UIs (011T) are the ones in charge of the "consumption" of the data by the users of the RDE.

RDE Apps (011S) bring to the users all the data and data knowledge of the RDE through REST calls both to the RDE Big Data Repository (011W) and the RDE Analytics Bridge (011K). They also show to the users all their relevant real time data through the Real Time Triggers, Alerts and Communications Queue (011P).

RDE UIs (011T) are the ones in charge of visualizing all the RDE Apps (011S) information by means of Views, Dashboards, Real time data boards, Queries and Scenarios.

Scenarios (011U) are particularly relevant for exchanging data with Third Party Actors (011R), as explained in Section where Scenarios are explained in this document.

Third Party Actors (011R) then, can obtain information from the RDE UIs (011T) as well from the Real Time Triggers, Alerts and Communications RDE Data Processors through its dedicated Messaging Queue (011R).

7.6. Sector 6—Data API for 3RD Services

Figure 39:
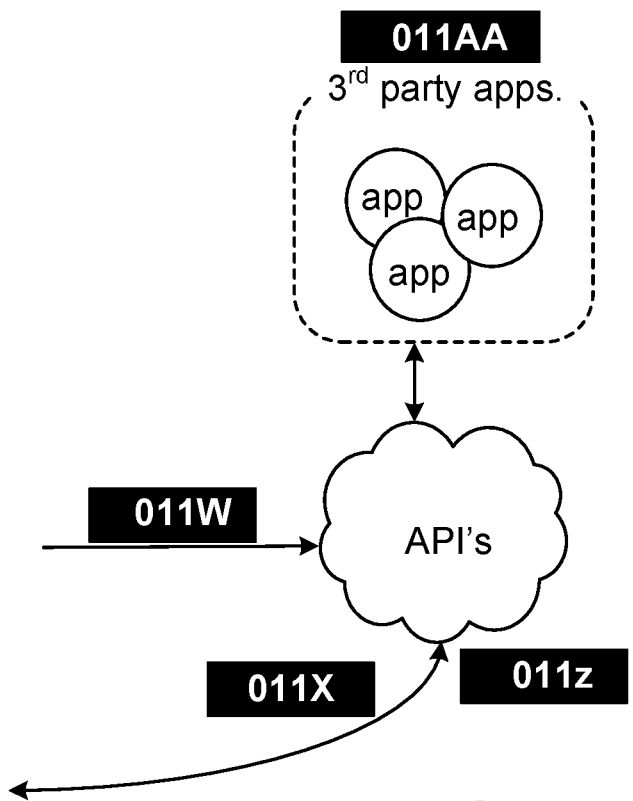
FIG. 39 is a diagram illustrating an example of a sixth sector of the data workflow of FIG. 33.

The workflow associated with this sector is described with respect to FIGS. 11 and 39.

In Sector 6, the RDE Data Engine API's (011Z) can provide REST services to 3rd Party Apps, services or platforms (011AA) to obtain informations from the RDE Data Engine, both Regulated Data from the RDE Big Data Repository, as well perform queries and obtain knowledge from the RDE Analytics Engine (011Y) and the RDE Trending Engine (011Z) through the RDE Analytics Engine (011X) exposure to the RDE Data Engine API's (011Z).

8. Summary of Features

Throughout this specification there have been described different elements linked among themselves by a functional thread, trying to provide a global vision of product. Nevertheless there are concepts that can be identified as individual elements that are innovative features when taken alone. These features include the following:

beID: This concept is not only the unique identification for any data source across the universe of elements in the RDE. The beID is the direct path (that can be fit for example by a hyperlink, a QR code or through a REST call) to any element existing in the system. From this access the end users can go in to the master information, records associated to this object, activities, agents and analytics and trends that are calculated for this element. References in sections: Owner account creation, 003C, 003E, 003F (beJSON definition) of FIG. 3, Agents and GUI elements to manage RDE system sections.

Envelope based on the $w^5$: For each received raw data, the RDE wraps the original message with an envelope that provides the regulatory layer needed to ensure the traceability and the validation of this primary information. The provided content included in this envelope answers to the following questions: who?, where?, when?, what? and why?. Described with respect to 002H of FIG. 2, Data acquisition (beSONdefinition), Automatic data relation. Natural association, Issuing information with required authenticated user sections and 008H of FIG. 8.

beJSON: This is the standard proposed by the RDE to establish a plain connection between objects that need to save massive information under regulated conditions. It is a structure based on JSON syntax, providing a contract with specific fields that grant the regulatory perspective to the incoming raw data. Described with respect to 003C, 003E, 003F (beJSON definition) of FIG. 3.

21 CFR Part 11 over PGP: The FDA proposed the 21 CFR Part 11 normative as the rule to be followed to guarantee the electronic information in pharma industries. Since the RDE manages electronic information that must be under regulatory control, the system must be compliant with this normative. This platform goes beyond the strict regulation, proposing a special model build on PGP encryption and authentication system. Reference in Regulatory Layer and Issuing information with required authenticated user sections.

bePedigree: The definition of this concept can be summarized as the automatic and dynamic self-constructed ID through the product life trace. This ID represents the path that links all the elements involved in a given query that has used the natural and the customized associations. The detail of this object is explained in the section bePedigree: the dynamic pedigree based on processes.

Natural association: When users do queries searching values and all the related information to a given object, but users do not do the action to add conditions in the criteria to search, RDE applies the natural association. This kind of association applies a specific algorithm to find relationships among all the objects that could be related with the focused element based on the information contained in the envelope ($w^5$). Main references in Automatic data relation section.

Views, processes and phases: A view is a set of processes related between themselves. The process conception from the RDE point of view is not anymore considered as a black box. From this perspective a process is a transparent box where objects can be associated at the input phase, at the output but also during the process execution. That can be considered as an enabler for PAT implementation, because all objects that are uploading data and that are associated to a "while" phase, are providing information for the monitoring in real time. Additionally, a dimensionless vector has been defined in order to compare heterogeneous processes and also characterizing the process activity with a numerical representation.

Agents: Are small pieces of code that decide which action to perform depending on the value associated to the incoming beJSON. Once primary data has been inserted into the system (graphically described in the IT Architecture section), if there is an agent associated to the data source (device, element or user), it takes an action after evaluating the configured acceptance criteria. There is a pseudo code that allows to configure the acceptance criteria as the action to do as well. Main references in Agents and IT Architecture sections.

Scenarios: They work like a view with special restrictions and base their special contribution in the different concepts that have been introduced previously. Only the information provided by public data sources (devices, elements or users) can be shared in scenarios. Besides, only the users that have been identified by their specific scenarios (using the authentication method explained in the Regulatory layer section) can access to this information. Main references in Scenarios section.

Customized association: This is the relational algorithm used by the RDE to associate existing records in the repository with other values and objects that are linked in some way. As far as the linking possibilities are extended to object association (Object association section above), process links (View Process Management section above), data structure (element 003C of FIG. 3) and automatic relations as well (relations described in Automatic data-relation section), the customized association is a systematic method that allows to find relations among records. References above in in Data association through customized relationships section.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method comprising:
    collecting data from a plurality of sources, wherein collecting data comprises receiving raw data records from a plurality of devices, systems, or users, the raw data records each having a plurality of parameters;
    for each raw data record:
        wrapping the raw data record with a corresponding envelope added to the data record, the envelope transforming the raw data to compliant data, wherein the envelope includes fields for attributes associated with the raw data record, wherein the fields of the envelope specify each of a plurality of who, where, when, what, and why attributes, wherein the attributes thereby remain attached to the raw data to provide traceability, and wherein the fields of the envelope include a validation field that includes a value calculated based on the raw data record that is used to determine whether the raw data record has been modified;
    analyzing the data including determining what accesses to provide to the collected data and assigning one or more alarm levels; and
    providing one or more outputs based on the analysis.

2. The method of claim 1, wherein, after wrapping each data record, the data record is sent to a data processor queue that process the data record including exposing parameters of the data record to one or more dashboards and processing any alert communications.

3. The method of claim 1, wherein, after wrapping a particular data record, the data record is provided to an agent, wherein the agent is a configurable listener that performs customized actions depending on the parameter values of the data record.

4. The method of claim 3, wherein the agent evaluates the parameter values of the data record based on the data source or data value-type, and wherein the agent is deployed based on defines alarm levels and actions to perform in response to each alarm.

5. The method of claim 1, wherein the envelope includes the unique identifier of the data source for the raw data, and wherein the unique identifier provides a tracing of the origin for all data records associated with the source.

6. The method of claim 1, wherein analyzing the data include generating one or more natural associations including applying one or more comparison criteria to the raw data records and the corresponding envelope information to automatically generate associations such that a search for particular values of raw or envelope data returns a set of values that are related between themselves through the one or more comparison criteria.

7. A system for managing regulated data comprising:
    one or more computers configured to perform operations comprising:

collecting data from a plurality of sources, wherein collecting data comprises receiving raw data records from a plurality of devices, systems, or users, the raw data records each having a plurality of parameters;

for each raw data record:

wrapping the raw data record with a corresponding envelope added to the data record, the envelope transforming the raw data to compliant data, wherein the envelope includes fields for attributes associated with the raw data record, wherein the fields of the envelope specify each of a plurality of who, where, when, what, and why attributes, wherein the attributes thereby remain attached to the raw data to provide traceability, and wherein the fields of the envelope include a validation field that includes a value calculated based on the raw data record that is used to determine whether the raw data record has been modified;

analyzing the data including determining what accesses to provide to the collected data and assigning one or more alarm levels; and providing one or more outputs based on the analysis.

8. The system of claim 7, wherein, after wrapping each data record, the data record is sent to a data processor queue that process the data record including exposing parameters of the data record to one or more dashboards and processing any alert communications.

9. The system of claim 7, wherein, after wrapping a particular data record, the data record is provided to an agent, wherein the agent is a configurable listener that performs customized actions depending on the parameter values of the data record.

10. The system of claim 9, wherein the agent evaluates the parameter values of the data record based on the data source or data value-type, and wherein the agent is deployed based on defines alarm levels and actions to perform in response to each alarm.

11. The system of claim 7, wherein the envelope includes the unique identifier of the data source for the raw data, and wherein the unique identifier provides a tracing of the origin for all data records associated with the source.

12. The system of claim 7, wherein analyzing the data include generating one or more natural associations including applying one or more comparison criteria to the raw data records and the corresponding envelope information to automatically generate associations such that a search for particular values of raw or envelope data returns a set of values that are related between themselves through the one or more comparison criteria.

13. One or more non-transitory computer-readable storage media encoded with instructions that, when executed by one or more computers, cause the one or more computers to perform operations comprising:

collecting data from a plurality of sources, wherein collecting data comprises receiving raw data records from a plurality of devices, systems, or users, the raw data records each having a plurality of parameters;

for each raw data record:

wrapping the raw data record with a corresponding envelope added to the data record, the envelope transforming the raw data to compliant data, wherein the envelope includes fields for attributes associated with the raw data record, wherein the fields of the envelope specify each of a plurality of who, where, when, what, and why attributes, wherein the attributes thereby remain attached to the raw data to provide traceability, and wherein the fields of the envelope include a validation field that includes a value calculated based on the raw data record that is used to determine whether the raw data record has been modified;

analyzing the data including determining what accesses to provide to the collected data and assigning one or more alarm levels; and providing one or more outputs based on the analysis.

14. The one or more non-transitory computer-readable storage media of claim 13, wherein, after wrapping each data record, the data record is sent to a data processor queue that process the data record including exposing parameters of the data record to one or more dashboards and processing any alert communications.

15. The one or more non-transitory computer-readable storage media of claim 13, wherein, after wrapping a particular data record, the data record is provided to an agent, wherein the agent is a configurable listener that performs customized actions depending on the parameter values of the data record.

16. The one or more non-transitory computer-readable storage media of claim 15, wherein the agent evaluates the parameter values of the data record based on the data source or data value-type, and wherein the agent is deployed based on defines alarm levels and actions to perform in response to each alarm.

17. The one or more non-transitory computer-readable storage media of claim 13, wherein the envelope includes the unique identifier of the data source for the raw data, and wherein the unique identifier provides a tracing of the origin for all data records associated with the source.

18. The one or more non-transitory computer-readable storage media of claim 13, wherein analyzing the data include generating one or more natural associations including applying one or more comparison criteria to the raw data records and the corresponding envelope information to automatically generate associations such that a search for particular values of raw or envelope data returns a set of values that are related between themselves through the one or more comparison criteria.

\* \* \* \* \*